US009271940B2

(12) United States Patent
Danagher et al.

(10) Patent No.: US 9,271,940 B2
(45) Date of Patent: Mar. 1, 2016

(54) IMMEDIATE RELEASE PHARMACEUTICAL COMPOSITIONS COMPRISING OXYCODONE AND NALOXONE

(75) Inventors: Helen Kathleen Danagher, Cambridge (GB); Geoffrey Gerard Hayes, Cambridge (GB); Gerhard Josef Heun, Limburg (DE); Hassan Mohammad, Cambridge (GB); Malcolm Walden, Cambridge (GB); Jonathon Oliver Whitehouse, Cambridge (GB)

(73) Assignee: Purdue Pharma L.P., Stamford, CT (US)

( * ) Notice: Subject to any disclaimer, the term of this patent is extended or adjusted under 35 U.S.C. 154(b) by 1104 days.

(21) Appl. No.: 13/255,504

(22) PCT Filed: Mar. 10, 2010

(86) PCT No.: PCT/EP2010/053028
§ 371 (c)(1),
(2), (4) Date: Dec. 19, 2011

(87) PCT Pub. No.: WO2010/103039
PCT Pub. Date: Sep. 16, 2010

(65) Prior Publication Data
US 2012/0088786 A1 Apr. 12, 2012

(30) Foreign Application Priority Data
Mar. 10, 2009 (EP) ..................... 09154805

(51) Int. Cl.
*A61K 31/439* (2006.01)
*A61P 29/02* (2006.01)
*A61K 9/20* (2006.01)
*A61K 31/485* (2006.01)

(52) U.S. Cl.
CPC ............ *A61K 9/2059* (2013.01); *A61K 9/2018* (2013.01); *A61K 31/485* (2013.01)

(58) Field of Classification Search
CPC . A61K 9/2018; A61K 9/2059; A61K 31/485; A61K 2300/00
See application file for complete search history.

(56) References Cited

U.S. PATENT DOCUMENTS

| | | |
|---|---|---|
| 2,770,569 A | 11/1956 | Fromherz et al. |
| 3,133,132 A | 5/1964 | Loeb et al. |
| 3,173,876 A | 3/1965 | Zobrist |
| 3,173,877 A | 3/1965 | Jackson et al. |
| 3,276,586 A | 10/1966 | Rosaen |
| 3,332,950 A | 7/1967 | Blumberg et al. |
| 3,493,657 A | 2/1970 | Lewenstein et al. |
| 3,541,005 A | 11/1970 | Strathmann et al. |
| 3,541,006 A | 11/1970 | Bixler et al. |
| 3,546,876 A | 12/1970 | Fokker et al. |
| 3,676,557 A | 7/1972 | Lachman et al. |
| 3,773,955 A | 11/1973 | Patcher et al. |
| 3,845,770 A | 11/1974 | Theeuwes et al. |
| 3,879,555 A | 4/1975 | Pachter et al. |
| 3,916,889 A | 11/1975 | Russell |
| 3,916,899 A | 11/1975 | Theeuwes et al. |
| 3,950,508 A | 4/1976 | Mony et al. |
| 3,965,256 A | 6/1976 | Leslie |
| 3,966,940 A | 6/1976 | Patcher et al. |
| 4,063,064 A | 12/1977 | Saunders et al. |
| 4,088,864 A | 5/1978 | Theeuwes et al. |
| 4,126,684 A | 11/1978 | Robson et al. |
| 4,160,020 A | 7/1979 | Ayer et al. |
| 4,176,186 A | 11/1979 | Goldberg |
| 4,200,098 A | 4/1980 | Ayer et al. |
| 4,216,314 A | 8/1980 | Raabe et al. |
| 4,237,140 A | 12/1980 | Dudzinski |
| 4,285,987 A | 8/1981 | Ayer et al. |
| 4,293,539 A | 10/1981 | Ludwig et al. |
| 4,366,310 A | 12/1982 | Leslie |
| 4,401,672 A | 8/1983 | Portoghese et al. |
| 4,443,428 A | 4/1984 | Oshlack et al. |
| 4,451,470 A | 5/1984 | Ganti |
| 4,457,933 A | 7/1984 | Gordon et al. |
| 4,464,378 A | 8/1984 | Hussain et al. |
| 4,573,995 A | 3/1986 | Chen et al. |
| 4,582,835 A | 4/1986 | Lewis et al. |
| 4,608,376 A | 8/1986 | Pasternak |
| 4,661,492 A | 4/1987 | Lewis et al. |
| 4,668,685 A | 5/1987 | Shami |
| 4,719,215 A | 1/1988 | Goldberg |
| 4,722,928 A | 2/1988 | Boswell et al. |
| 4,730,048 A | 3/1988 | Portoghese et al. |
| 4,760,069 A | 7/1988 | Rzeszotarski et al. |

(Continued)

FOREIGN PATENT DOCUMENTS

| | | |
|---|---|---|
| AU | 200205559 | 11/2002 |
| CA | 2382648 | 3/2001 |

(Continued)

OTHER PUBLICATIONS

Abdulla et al., "Axotomy reduces the effect of analgesic opioids yet increases the effect of nociceptin on dorsal root ganglion neurons"; J of Neuro Sci (1998) vol. 18, pp. 9685-9694.
Abernethy et al., Randomised, double blind, placebo controlled crossover trial of sustained release morphine for the management of refractory dyspnoea, BMJ, vol. 327, 6 pages. (2003).
Alvarez-Fuentes et al. "Effectiveness of Repeated Administration of a New Oral Naltrexone Controlled-Release System in Morphine Analgesia"; J. Pharm Pharmacol (2001), 53:1201-1205.
Alvarez-Fuentes, et al., "Preclinical Study of an Oral Controlled Release Naltrexone Complex in Mice"; J. Pharm Pharmacol (2000), 52:659-663.
Amass et al., "Efficacy of daily and alternate-day dosing regimens with the combibation buprenorphine-naloxone tablet"; Drug and Alcohol Dependence (2000) vol. 58, pp. 143-152.

(Continued)

Primary Examiner — Ali Soroush
Assistant Examiner — Genevieve S Alley
(74) Attorney, Agent, or Firm — Dechert LLP

(57) ABSTRACT

The present invention pertains to oral immediate release pharmaceutical compositions suitable for treating patients suffering from pain comprising oxycodone and naloxone or their pharmaceutically acceptable salts.

31 Claims, 9 Drawing Sheets

(56) References Cited

U.S. PATENT DOCUMENTS

| | | |
|---|---|---|
| 4,769,372 A | 9/1988 | Kreek |
| 4,785,000 A | 11/1988 | Kreek et al. |
| 4,803,208 A | 2/1989 | Pasternak |
| 4,806,341 A | 2/1989 | Chien et al. |
| 4,806,543 A | 2/1989 | Choi |
| 4,806,558 A | 2/1989 | Wuest et al. |
| 4,828,836 A | 5/1989 | Elger et al. |
| 4,834,965 A | 5/1989 | Martani et al. |
| 4,834,984 A | 5/1989 | Goldie et al. |
| 4,834,985 A | 5/1989 | Elger et al. |
| 4,844,907 A | 7/1989 | Elger et al. |
| 4,844,909 A | 7/1989 | Goldie et al. |
| 4,844,910 A | 7/1989 | Leslie et al. |
| 4,861,598 A | 8/1989 | Oshlack |
| 4,861,781 A | 8/1989 | Goldberg |
| 4,867,985 A | 9/1989 | Heafield et al. |
| 4,873,076 A | 10/1989 | Fishman et al. |
| 4,882,335 A | 11/1989 | Sinclair |
| 4,889,860 A | 12/1989 | Rzeszotarski et al. |
| 4,935,428 A | 6/1990 | Lewis |
| 4,940,587 A | 7/1990 | Jenkins et al. |
| 4,957,681 A | 9/1990 | Klimesch et al. |
| 4,970,075 A | 11/1990 | Oshlack |
| 4,987,136 A | 1/1991 | Kreek et al. |
| 4,990,341 A | 2/1991 | Goldie et al. |
| 5,071,646 A | 12/1991 | Malkowska et al. |
| 5,075,341 A | 12/1991 | Mendelson et al. |
| 5,086,058 A | 2/1992 | Sinclair et al. |
| 5,091,189 A | 2/1992 | Heafield et al. |
| 5,096,715 A | 3/1992 | Sinclair |
| 5,102,887 A | 4/1992 | Goldberg |
| 5,130,311 A | 7/1992 | Guillaumet et al. |
| 5,149,538 A | 9/1992 | Granger et al. |
| 5,215,758 A | 6/1993 | Krishnamurthy |
| 5,225,440 A | 7/1993 | London et al. |
| 5,236,714 A | 8/1993 | Lee et al. |
| 5,256,669 A | 10/1993 | Askanazi et al. |
| 5,266,331 A | 11/1993 | Oshlack et al. |
| 5,273,760 A | 12/1993 | Oshlack et al. |
| 5,286,493 A | 2/1994 | Oshlack et al. |
| 5,316,759 A | 5/1994 | Rose et al. |
| 5,317,022 A | 5/1994 | Borsodi et al. |
| 5,321,012 A | 6/1994 | Mayer et al. |
| 5,324,351 A | 6/1994 | Oshlack et al. |
| 5,336,691 A | 8/1994 | Raffa et al. |
| 5,352,680 A | 10/1994 | Portoghese et al. |
| 5,352,683 A | 10/1994 | Mayer et al. |
| 5,356,467 A | 10/1994 | Oshlack et al. |
| 5,356,900 A | 10/1994 | Bihari et al. |
| 5,376,662 A | 12/1994 | Ockert |
| 5,409,944 A | 4/1995 | Black et al. |
| 5,411,745 A | 5/1995 | Oshlack et al. |
| 5,426,112 A | 6/1995 | Zagon et al. |
| 5,436,265 A | 7/1995 | Black et al. |
| 5,457,208 A | 10/1995 | Portoghese et al. |
| 5,460,826 A | 10/1995 | Merrill et al. |
| 5,472,712 A | 12/1995 | Oshlack et al. |
| 5,472,943 A | 12/1995 | Crain et al. |
| 5,474,995 A | 12/1995 | Ducharme et al. |
| 5,478,577 A | 12/1995 | Sackler et al. |
| 5,486,362 A | 1/1996 | Kitchell et al. |
| 5,500,227 A | 3/1996 | Oshlack et al. |
| 5,502,058 A | 3/1996 | Mayer et al. |
| 5,508,042 A | 4/1996 | Oshlack et al. |
| 5,508,043 A | 4/1996 | Krishnamurthy |
| 5,510,368 A | 4/1996 | Lau et al. |
| 5,512,578 A | 4/1996 | Crain et al. |
| 5,514,680 A | 5/1996 | Weber et al. |
| 5,521,213 A | 5/1996 | Prasit et al. |
| 5,534,492 A | 7/1996 | Aston et al. |
| 5,536,752 A | 7/1996 | Ducharme et al. |
| 5,549,912 A | 8/1996 | Oshlack et al. |
| 5,550,142 A | 8/1996 | Ducharme et al. |
| 5,552,422 A | 9/1996 | Gauthier et al. |
| 5,556,838 A | 9/1996 | Mayer et al. |
| 5,574,052 A | 11/1996 | Rose et al. |
| 5,578,725 A | 11/1996 | Portoghese et al. |
| 5,580,578 A | 12/1996 | Oshlack et al. |
| 5,580,876 A | 12/1996 | Crain et al. |
| 5,585,348 A | 12/1996 | Crain et al. |
| 5,591,452 A | 1/1997 | Miller et al. |
| 5,592,310 A | 1/1997 | Sugiura et al. |
| 5,593,994 A | 1/1997 | Batt et al. |
| 5,601,845 A | 2/1997 | Buxton et al. |
| 5,604,253 A | 2/1997 | Lau et al. |
| 5,604,260 A | 2/1997 | Guay et al. |
| 5,616,601 A | 4/1997 | Khanna et al. |
| 5,622,722 A | 4/1997 | Knott et al. |
| 5,624,932 A | 4/1997 | Qin et al. |
| 5,633,259 A | 5/1997 | Qin et al. |
| 5,639,476 A | 6/1997 | Oshlack et al. |
| 5,639,780 A | 6/1997 | Lau et al. |
| 5,656,295 A | 8/1997 | Oshlack et al. |
| 5,670,172 A | 9/1997 | Buxton et al. |
| 5,672,360 A | 9/1997 | Sackler et al. |
| 5,681,585 A | 10/1997 | Oshlack et al. |
| 5,692,500 A | 12/1997 | Gaston-Johansson |
| 5,763,452 A | 6/1998 | Miller et al. |
| 5,767,125 A | 6/1998 | Crain et al. |
| 5,780,479 A | 7/1998 | Kim |
| 5,811,126 A | 9/1998 | Krishnamurthy |
| 5,834,477 A | 11/1998 | Mioduszewski |
| 5,843,480 A | 12/1998 | Miller et al. |
| 5,849,240 A | 12/1998 | Miller et al. |
| 5,858,017 A | 1/1999 | Demopulos et al. |
| 5,860,950 A | 1/1999 | Demopulos et al. |
| 5,866,154 A | 2/1999 | Bahal et al. |
| 5,866,164 A | 2/1999 | Kuczynski et al. |
| 5,869,097 A | 2/1999 | Wong et al. |
| 5,879,705 A | 3/1999 | Heafield et al. |
| 5,880,132 A | 3/1999 | Hill |
| 5,891,471 A | 4/1999 | Miller et al. |
| 5,908,848 A | 6/1999 | Miller et al. |
| 5,942,241 A | 8/1999 | Chasin et al. |
| 5,958,452 A | 9/1999 | Oshlack et al. |
| 5,958,459 A | 9/1999 | Chasin et al. |
| 5,965,161 A | 10/1999 | Oshlack et al. |
| 5,965,163 A | 10/1999 | Miller et al. |
| 5,968,547 A | 10/1999 | Reder et al. |
| 5,968,551 A | 10/1999 | Oshlack et al. |
| 5,972,310 A | 10/1999 | Sachetto |
| 5,972,954 A | 10/1999 | Foss et al. |
| 5,998,434 A | 12/1999 | Mitch et al. |
| 6,024,982 A | 2/2000 | Oshlack et al. |
| 6,068,855 A | 5/2000 | Leslie et al. |
| 6,077,532 A | 6/2000 | Malkowska et al. |
| 6,077,533 A | 6/2000 | Oshlack et al. |
| 6,096,756 A | 8/2000 | Crain et al. |
| 6,103,258 A | 8/2000 | Simon |
| 6,103,261 A | 8/2000 | Chasin et al. |
| 6,114,326 A | 9/2000 | Schueler |
| 6,143,322 A | 11/2000 | Sackler et al. |
| 6,143,328 A | 11/2000 | Heafield et al. |
| 6,159,501 A | 12/2000 | Skinhoj et al. |
| 6,162,467 A | 12/2000 | Miller et al. |
| 6,194,382 B1 | 2/2001 | Crain et al. |
| 6,207,142 B1 | 3/2001 | Odds et al. |
| 6,210,714 B1 | 4/2001 | Oshlack et al. |
| 6,228,863 B1 | 5/2001 | Palermo et al. |
| 6,254,887 B1 | 7/2001 | Miller et al. |
| 6,258,042 B1 | 7/2001 | Factor et al. |
| 6,261,599 B1 | 7/2001 | Oshlack et al. |
| 6,277,384 B1 | 8/2001 | Kaiko et al. |
| 6,294,195 B1 | 9/2001 | Oshlack et al. |
| 6,306,438 B1 | 10/2001 | Oshlack et al. |
| 6,310,072 B1 | 10/2001 | Smith et al. |
| 6,326,027 B1 | 12/2001 | Miller et al. |
| 6,335,033 B2 | 1/2002 | Oshlack et al. |
| 6,362,194 B1 | 3/2002 | Crain et al. |
| 6,375,957 B1 | 4/2002 | Kaiko et al. |
| 6,387,404 B2 | 5/2002 | Oshlack et al. |
| 6,395,705 B2 | 5/2002 | Crain et al. |
| 6,399,096 B1 | 6/2002 | Miller et al. |
| 6,419,959 B1 | 7/2002 | Walter et al. |

(56) References Cited

U.S. PATENT DOCUMENTS

| | | |
|---|---|---|
| 6,451,806 B2 | 9/2002 | Farrar et al. |
| 6,475,494 B2 | 11/2002 | Kaiko et al. |
| 6,579,536 B1 | 6/2003 | Hirsch et al. |
| 6,596,900 B2 | 7/2003 | Blakemore et al. |
| 6,602,868 B2 | 8/2003 | McBrinn et al. |
| 6,627,635 B2 | 9/2003 | Palermo et al. |
| 6,696,066 B2 | 2/2004 | Kaiko et al. |
| 6,696,088 B2 | 2/2004 | Oshlack et al. |
| 6,706,281 B2 | 3/2004 | Oshlack et al. |
| 6,716,449 B2 | 4/2004 | Oshlack et al. |
| 6,743,442 B2 | 6/2004 | Oshlack et al. |
| 6,765,010 B2 | 7/2004 | Crain et al. |
| 7,172,767 B2 | 2/2007 | Kaiko et al. |
| 7,332,182 B2 | 2/2008 | Sackler |
| 7,419,686 B2 | 9/2008 | Kaiko et al. |
| 7,637,906 B2 | 12/2009 | Koop et al. |
| 7,749,542 B2 | 7/2010 | Kaiko et al. |
| 8,105,631 B2 | 1/2012 | Kaiko et al. |
| 8,673,355 B2 | 3/2014 | Kaiko et al. |
| 8,822,487 B2 | 9/2014 | Kaiko et al. |
| 8,846,090 B2 | 9/2014 | Brögmann et al. |
| 8,846,091 B2 | 9/2014 | Brögmann et al. |
| 2001/0006967 A1 | 7/2001 | Crain et al. |
| 2001/0018413 A1 | 8/2001 | Crain et al. |
| 2001/0053777 A1 | 12/2001 | Brecht |
| 2002/0006964 A1 | 1/2002 | Young et al. |
| 2002/0010127 A1 | 1/2002 | Oshlack et al. |
| 2002/0031552 A1 | 3/2002 | McTeigue et al. |
| 2003/0004177 A1 | 1/2003 | Kao et al. |
| 2003/0044458 A1 | 3/2003 | Wright, IV et al. |
| 2003/0065002 A1 | 4/2003 | Caruso et al. |
| 2003/0069263 A1 | 4/2003 | Breder et al. |
| 2003/0073714 A1 | 4/2003 | Breder et al. |
| 2003/0092759 A1 | 5/2003 | Abuzzahab, Sr. |
| 2003/0118641 A1 | 6/2003 | Maloney et al. |
| 2003/0143269 A1 | 7/2003 | Oshlack et al. |
| 2003/0178031 A1 | 9/2003 | DuPen et al. |
| 2003/0191147 A1 | 10/2003 | Sherman et al. |
| 2003/0229111 A1 | 12/2003 | Oshlack et al. |
| 2004/0052731 A1 | 3/2004 | Hirsh et al. |
| 2004/0092542 A1 | 5/2004 | Oshlack et al. |
| 2004/0186121 A1 | 9/2004 | Oshlack et al. |
| 2005/0063909 A1 | 3/2005 | Wright et al. |
| 2005/0095291 A1 | 5/2005 | Oshlack et al. |
| 2005/0163856 A1 | 7/2005 | Maloney et al. |
| 2005/0181046 A1 | 8/2005 | Oshlack et al. |
| 2005/0245483 A1 | 11/2005 | Brogmann et al. |
| 2005/0245556 A1 | 11/2005 | Brogmann et al. |
| 2005/0272776 A1 | 12/2005 | Buehler |
| 2006/0039970 A1 | 2/2006 | Oshlack et al. |
| 2006/0182801 A1 | 8/2006 | Breder et al. |
| 2007/0122348 A1 | 5/2007 | Kaiko et al. |
| 2007/0185146 A1 | 8/2007 | Fleischer et al. |
| 2008/0145429 A1 | 6/2008 | Leyendecker et al. |
| 2011/0172259 A1 | 7/2011 | Leyendecker et al. |
| 2012/0108621 A1 | 5/2012 | Brogmann et al. |
| 2012/0225901 A1 | 9/2012 | Leyendecker et al. |
| 2014/0031382 A1 | 1/2014 | Leyendecker et al. |
| 2014/0045877 A1 | 2/2014 | Brogmann et al. |
| 2014/0296277 A1 | 10/2014 | Brogmann et al. |

FOREIGN PATENT DOCUMENTS

| | | |
|---|---|---|
| CA | 2478515 | 10/2003 |
| CA | 2478523 | 10/2003 |
| CA | 2372025 | 9/2007 |
| DE | 2138593 | 3/1972 |
| DE | 4325465 | 2/1995 |
| EP | 0193355 | 9/1986 |
| EP | 0205282 | 12/1986 |
| EP | 0319243 | 6/1989 |
| EP | 0352361 | 1/1990 |
| EP | 0527638 | 2/1993 |
| EP | 0576643 | 6/1993 |
| EP | 624366 | 11/1994 |
| EP | 0631781 | 1/1995 |
| EP | 0647448 | 4/1995 |
| EP | 0699436 | 3/1996 |
| EP | 0880352 | 2/1998 |
| EP | 0913152 | 5/1999 |
| EP | 1201233 | 5/2002 |
| EP | 1348429 | 10/2003 |
| EP | 1364649 | 11/2003 |
| EP | 1604666 | 12/2005 |
| EP | 1041987 B1 | 4/2006 |
| EP | 1695700 * | 8/2006 |
| EP | 1813276 | 8/2007 |
| GB | 1353815 | 5/1974 |
| GB | 1390772 | 4/1975 |
| JP | H10-251149 | 9/1998 |
| NZ | 260408 | 5/1996 |
| NZ | 264953 | 11/1996 |
| NZ | 260883 | 6/1997 |
| NZ | 294897 | 10/1998 |
| NZ | 544181 | 12/2008 |
| RU | 98102450 | 7/1996 |
| RU | 2222260 | 1/2004 |
| WO | WO 83/03197 | 9/1983 |
| WO | WO 87/01282 | 3/1987 |
| WO | WO 90/04965 | 5/1990 |
| WO | WO 93/10765 | 6/1993 |
| WO | WO 94/06426 | 3/1994 |
| WO | WO 95/03804 | 2/1995 |
| WO | WO 96/02251 | 2/1996 |
| WO | WO 96/14058 | 5/1996 |
| WO | WO 96/14059 | 5/1996 |
| WO | WO 97/33566 | 9/1997 |
| WO | WO 97/45091 | 12/1997 |
| WO | WO 98/25613 | 6/1998 |
| WO | WO 98/35679 | 8/1998 |
| WO | WO 99/01111 | 1/1999 |
| WO | WO 99/05960 | 2/1999 |
| WO | WO 99/11250 | 3/1999 |
| WO | WO 99/22737 | 5/1999 |
| WO | WO 99/32119 | 7/1999 |
| WO | WO 99/32120 | 7/1999 |
| WO | WO 00/01377 | 1/2000 |
| WO | WO 00/25821 | 5/2000 |
| WO | WO 00/38649 | 7/2000 |
| WO | WO 00/41683 | 7/2000 |
| WO | WO 00/51592 | 9/2000 |
| WO | WO 00/67739 | 11/2000 |
| WO | WO 01/32180 | 5/2001 |
| WO | WO 01/37785 | 5/2001 |
| WO | WO 01/52851 | 7/2001 |
| WO | WO 01/58447 | 8/2001 |
| WO | WO 01/58451 | 8/2001 |
| WO | WO 01/68080 | 9/2001 |
| WO | WO 01/85150 | 11/2001 |
| WO | WO 01/85257 | 11/2001 |
| WO | WO 01/93852 | 12/2001 |
| WO | WO 02/087512 | 11/2002 |
| WO | WO 02/092059 | 11/2002 |
| WO | WO 02/092060 | 11/2002 |
| WO | WO 03/003541 | 1/2003 |
| WO | WO 03/004009 | 1/2003 |
| WO | WO 03/007802 | 1/2003 |
| WO | WO 03/013476 | 2/2003 |
| WO | WO 03/013479 | 2/2003 |
| WO | WO 03/013538 | 2/2003 |
| WO | WO 03/020124 | 3/2003 |
| WO | WO 03/024429 | 3/2003 |
| WO | WO 03/024430 | 3/2003 |
| WO | WO 03/026676 | 4/2003 |
| WO | WO 03/073937 | 9/2003 |
| WO | WO 03/084504 | 10/2003 |
| WO | WO 03/084520 | 10/2003 |
| WO | WO 2004/026262 | 4/2004 |
| WO | WO 2004/064807 | 8/2004 |
| WO | WO 2004/091623 | 10/2004 |
| WO | WO 2005/000310 | 1/2005 |
| WO | WO 2005/025621 | 3/2005 |
| WO | WO 2005/079760 | 9/2005 |

(56) References Cited

FOREIGN PATENT DOCUMENTS

| | | |
|---|---|---|
| WO | WO 2005/120506 | 12/2005 |
| WO | WO 2005/120507 | 12/2005 |
| WO | WO 2006/024881 | 3/2006 |
| WO | WO 2006/079550 | 8/2006 |
| WO | WO 2006/089970 | 8/2006 |
| WO | WO 2006/089973 | 8/2006 |
| WO | WO 2007/047935 | 4/2007 |
| WO | WO 2007/085637 | 8/2007 |
| WO | WO 2007/088489 | 8/2007 |
| WO | WO 2007/111945 | 10/2007 |
| WO | WO 2007/123865 | 11/2007 |
| WO | WO 2008/025790 | 3/2008 |
| WO | WO 2008/030567 | 3/2008 |
| WO | WO 2009/040394 | 4/2009 |
| WO | WO 2010/003963 | 1/2010 |
| WO | WO 2010/103039 | 9/2010 |
| WO | WO 2012/020097 | 2/2012 |

OTHER PUBLICATIONS

Amati et al., "In vitro effects of naloxone on T-lymphocyte-dependent antibacterial activity in hepatitis C virus (HCV) infected patients and in inflammatory bowel disease (IBD) patient," Immunopharmacology and Immonotoxicology, vol. 23, No. 1 (2001), pp. 1-11 (2001).

Archer Sydney; "Historical Perspective on the Chemistry and Development of Naltrexone"; Naltrexone Research Monograph28 (1980) p. 3-9.

Australian Search Report dated Aug. 20, 2014 relating to United Emirates Application No. UAE/P/770/2007.

Azamari et al., "Thermal treating as a tool for sustained release of indomethacin from Eudragit RS and RL matrices," International Journal of Pharmaceutics, 246, 171-177 (2002).

Barton et al., "Intranasal Administration of Naloxone by Paramedics";Prehospital Emergency Care (2002) vol. 6, No. 1, pp. 54-58.

Bashaw et al., "Relative bioavailability of controlled-release oral morphine sulfate during naltrexone blockade"; Inter J of Clin Pharm and Thea (1995) vol. 33, No. 9, 524-529.

Baum et al., "The Impact of the Addition of Naloxone on the Use and Abuse of Pentazocine"; Public Health Reports (1987) vol. 102, No. 4 p. 426-429.

Beauford et al., "Effects of Nebulized Morphine Sulfate on the Exercise Tolerance Ventilatory Limited COPD Patient," Chest, vol. 104, No. 1, pp. 175-178 (1993).

Benfey "Function of Myocardial-Adrenoceptors" ; Life Sciences (1982) vol. 31, pp. 101-112.

Benziger et al., "Differential effects of food on the bioavailability of controlled release oxycodone tablets and it oxycodone solution" J Pharm Sciences, vol. 85, No. 4, pp. 407-410 (1996).

Berkow, R. (ed.) Merck Manual of Medical Information, pp. 528-530 (1997).

Berkow, R. (ed.) The Merck Manual of Diagnosis and Therapy (1997), extract (English Translation from Russian).

Bigelow et al., "Abuse Liability and Assessment of Buprenorphine-Naloxone Combinations"; Dept of Psychiatry and Behavioral Sciences, The Johns Hopkins University School of Medicine, pp. 145-149, (1987).

Blachly Paul, H., M.D., "Naloxone in Opiate Addiction"; Current Psychiatric Therapies (1976) pp. 209-213.

Bloom et al., "Clinical Studies with Naloxone/Methadone in a Ratio of 1:20"; 5th National Conference on Methadone Treatment (1973) vol. 2, p. 1342-1349.

Brennscheidt et al., "Pharmacokinetics of Nortilidine and Naloxone after Administration of Tilidine/Naloxone Solution or Tilidine/Naloxone Sustained Release Tablets"; Arzeim-Forsch/Drug Res. (2000) vol. 50, pp. 1015-1022.

Briscoe et al., "Methoclocinnamox: Time Course of Changes in Alfetnanil-Reinforced Rhesus Monkeys"; Psychopharmacology (2000) 148:393-399.

Bromm et al., "A Sensitive Method to Evaluate Effects of Analgesics in Man"; Meth and Find Exptl Clin Pharmacol 5 (8) (1983) p. 545-551 (abstract).

Budd, Keith, "Clinical Use of Opioid Antagonists"; Bailliere's Clinical Anesthesiology (1987) vol. 1, No. 4, pp. 993-1011.

Bullingham et al., "Clinical Pharmacokinetics of Narcotic Agonist-Antagonist Drugs"; Clinical Pharm (1983) 8: 332-343.

Bunzow et al., "Molecular cloning and tissue distribution of a putative member of the rat opioid receptor gene family that is not a mu, delta or kappa opioid receptor type." FEBS Lett. Jun. 27, 1994;347(2-3):284-8.

Caldwell et al., "Treatment of Osteoarthritis Pain with Controlled Release Oxycodone or Fixed Combination Oxycodone Plus Acetaminophen Added to Nonsteroidal Antiinflammatory Drugs: A Double Blind, Randomized, Multicenter, Placebo Controlled Trial," J Rheumatol. vol. 26, No. 4, pp. 862-869 (1999).

Calimlim, et al. "Effect of Naloxone on the Analgesic Activity of Methadone in a 1:10 Oral Combination"; Clin Pharmacol and There (1974) vol. 15; No. 6 pp. 556-564.

Cappel et al., "Enhancement of Naloxone Induced Analgesia by Pretreatment with Morphine" Pharma. Bioch. & Behav. (1989), 34:425-427.

Caruso et al., "Methadone and Naloxone in Combination (Naldone®) for the Treatment of Heroin Addicts"; Bristol Laboratories, pp. 1336-1341 (1973).

Chambers Dictionary of Science and Technology, Ed. P.M.B. Walker, Chambers, 1999, p. 803.

Chen et al., "Challenges and New Technologies of Oral Controlled Release," Oral Controlled Release Formulation Design and Drug Delivery: Theory to Practice (2010) pp. 257-277.

Chen et al., "Oral naloxone reverses opioid-associated constipation," Foreign Medical Sciences: Anesthesiology and Resuscitation, vol. 21, No. 5, p. 319 (2000).

Cherny Nathan I., "Opioid Analgesics"; Drugs May 1996:51 (5) pp. 713-737.

Cherry et al., "Opioids in Pain Therapy," The Frankfurt Consensus, STK—Special Issue 2001 Article 2 (3 pages) (in German, w/ English translation).

Chiang et al. "Clinical Evaluation of a Naltrexone Sustained-Release Preparation"; Drug and Alcohol Dependence (1985) 16, pp. 1-8.

Chiang et al., "Kinetics of a Naltrexone Sustained-Release Preparation"; Clin Pharmacy Thera (1984) vol. 36 No. 5, pp. 704-708.

Chih-Cheng Chien et al., "Sigma Antagonists Potentiate Opioid Analgesia in Rats", Neuroscience Letters 190 (1995), 137-139.

Choi et al., "Opioid Antagonists: A Review of Their Role in Palliative care, Focusing on Use in Opioid-Related Constipation," J. of Pain and Symptom Management, vol. 24(1): 71-90.

Ciccocioppo et al., "Effect of Nociceptin/orphanin FQ on the Rewarding Properties of Morphine"; Eur. J Pharmacol (2000) vol. 404, pp. 153-159.

Citron et al., "Long-term administration of controlled release oxycodone tablets for the treatment of cancer pain," Cancer Investigation, vol. 16, No. 8, pp. 562-571 (1998).

Clark et al., "Symptom indexes to assess outcomes of treatment for early prostate cancer" Medical Care (2001) 39(10) 1118-1130.

Clemens et al., "Combined oral prolonged-release oxycodone and naloxone in opioid-induced bowel dysfunction: review of efficacy and safety data in the treatment of patients experiencing chronic pain," Expert Opinion on Pharmacotherapy, 11(2):297-310 (2010).

Cohen Statistical Power Analysis for the Behavioral Sciences (2nd ed.) Hillsdale, NJ: Erlbaum (1988), table of contents only.

Comer et al., "Depot Naltrexone: Long-lasting Antagonism of the Effects of Heroin un Humans"; Psychopharmacology (2002) 159, pp. 351-360.

Complaint for Declaratory Judgment filed in the United States District Court for the Western District Court of Virginia on Nov. 17, 2008, Civil Action No. 1:08CV00050.

Crabtree et al., "Review of Naltrexone, a long-acting Opiate Antagonist"; Clinical Pharmacy, vol. 3 (1984) pp. 273-280.

Crain et al. "Antagonists of excitatory opioid receptor functions enhance morphine's analgesic potency and attenuate opioid tolerance/dependence liability," Pain, vol. 84 pp. 121-131 (2000).

(56) References Cited

OTHER PUBLICATIONS

Crain et al., "Acute thermal hyperalgesia elicited by low-dose morphine in normal mice is blocked by ultra-low-dose naltrexone, unmasking potent opioid analgesia"; Brain Research (2001) vol. 888, pp. 75-82.
Crain et al., "Antagonists of Excitatory Opioid Receptor Functions Enhance Morphine's Analgesic Potency and Attenuate Opioid Tolerance/dependence liability"; Dept. of Neuroscience, Albert Einstein College of Medicine Pain 84 (2000) pp. 121-131.
Crain et al., "Ultra-Low Concentrations of Naloxone Selectively Antagonize Excitory Effects of Morphine on Sensory Neurons, Thereby Increasing Its Antinociceptive Potency and Attenuating Tolerance/Dependence During Chronic Cotreatment," Proc. Natl. Acad. Sci. USA (1995) 92:10540-10544.
Culpepper-Morgan et al., "Treatment of opioid-induced constipation with oral naloxone: A pilot study." Clinical Trials and Therapeutics, (1992) vol. 52(1): 90-95.
Davies, S., "Rising to the pain challenge," Drug News Perspect, 19(10):653-8 (2006).
Delbarre et al., Naloxone effects on blood pressure, analgesia and dieresis in spontaneous hypertensive and normotensive rats; Neuroscience Letters, vol. 30; pp. 167-172 (1982).
Deyo et al. "Reproducibility and responsiveness of health status measures. Statistics and strategies for evaluation" Cont. Clin. Trials (1991) 12:142S-158S.
Di Giannuario et al., "Orphanin FQ reduces morphine-induced dopamine release in the nucleus accumbens: a microdialysis study in rats"; Neurosci. Lett (1999) vol. 272 pp. 183-186.
Dictionary of Modern Computer Terms, S.-P.: BHV-Petersburg, p. 215 (2004).
Drossman et al. "Rome II: The Functional Gastrointestinal Disorders," 2nd ed. (2000) McLean, VA: Degon Associates, table of contents only.
Ebell et al., "The management of pain in cancer patients," Supportive Measures in Oncology, Jehn et al., eds., 1994, vol. 3 (in German, w/ English translation).
Eissenberg et al. "Buprenophine's physical dependence potential: Antagonist-precipitated withdrawal in humans," J. Pharmacol. Exp. Therapeut. vol. 276, No. 2, p. 449 (1996).
EP Application No. EP05020579.8: Communication forwarding the European Search Report dated Feb. 7, 2006.
EP Application No. EP05020580.6: Communication forwarding the European Search Report dated Feb. 8, 2006.
EP Application No. EP10176078.3: Communication forwarding the European Search Report dated Mar. 8, 2011.
EP Application No. EP10180364.1: Office Communication and European Search Report, dated Dec. 10, 2010.
EP Application No. EP10180425.0: Office Communication and European Search Report, dated Dec. 10, 2010.
EP Application No. EP10180494.6: Communication forwarding the European Search Report dated Mar. 9, 2011.
EP Application No. EP10180495.3: Communication forwarding the European Search Report dated Feb. 25, 2011.
EP Application No. EP10180496.1: Communication forwarding the European Search Report dated Mar. 9, 2011.
EP Application No. EP10180498.7: Communication forwarding the European Search Report dated Mar. 9, 2011.
EP Application No. EP11177513.6: European Search report and Search opinion dated Feb. 2, 2012.
EP Application No. EP11177516.9: European Search report and Search opinion dated Feb. 2, 2012.
EP Application No. EP11177518.5: European Search report and Search opinion dated Feb. 2, 2012.
EP Application No. EP11177520.1: European Search report and Search opinion dated Feb. 2, 2012.
European Patent No. EP1492506: Apr. 25, 2012 grounds of appeal of patentee.
European Patent No. EP1492506: Dec. 16, 2011 Minutes of Oral Proceedings and Decision of the Opposition Division.
European Patent No. EP1492506: May 10, 2010 Patentee reply to Notice of Opposition.
European Patent No. EP1492506: May 26, 2011 Summons to attend oral proceedings.
European Patent No. EP1492506: Opposition dated Sep. 30, 2009 by Hexal AG (English translation).
European Patent No. EP1492506: Sep. 9, 2011 written submissions of patentee.
Excerpt from Industrial Pharmacy, "Classification of drug delivery systems," 1996 (English translation).
Fink et al., "Naloxone in Heroin Dependence"; Clin Pharm and Thera. vol. 9, No. 5;pp. 568-577, (1968).
Fishman et al., "Disposition of Naloxone-7,8-3H in Normal & Narcotic Dependent Men"; J. Pharm. and Exper. Thera (1973)vol. 10 No. 2;pp. 575-580.
Forth et al., General and Special Pharmacology and Toxicology, 7th rev. ed., 1996, pp. 207-217 (in German w/English Translation).
Foss et al., "Dose related Antagonism of the Emetic Effect of Morphine by Methylnaltrexone in Dogs",J. Clin Pharmacol (1993), 33:747-751.
Foss J.F., et al. Abstract, "Prevention of Apomorphine- or Cisplatin-induced emesis in the dog by combination of Methylnaltrexone and Morphine",Cancer Chemother Pharmacol (1998); 42(4):287-91.
Fraser Albert D., et al., "Clinical Toxicology of Drugs Used in the Treatment of Opiate Dependency"; Clinical Toxicology I (1990) vol. 10, No. 2; pp. 375-386.
Freye et al., 'Effects of Tramadol and Tilidine/Naloxone on Oral-Caecal Transit & Pupillary light Reflex'; Arzneim-Forsch/Drug Res. 50(I)(2000)pp. 24-30.
Fudala et al., "Effects of Buprenorphine and Naloxone in Morphine-Stabilized Opioid Addicts"; Drug and Alcohol Dependence 50 (1998) pp. 1-8.
Fudala et al., "Human Pharmacology and Abuse Potential of Nalmefene"; Clin Pharm and Thera (1991) vol. 49, 3, pp. 300-306.
Gal et al., "Prolonged Blockade of Opioid Effect with Oral Nalmefene"; Clin Pharm and Thera (1986) pp. 537-542.
Gan et al., "Opioid-Sparing Effects of a Low-Dose Infusion of Naloxone in Patient-Administered Morphine Sulfate," Anesthesiology (1997), 87(5):1075-1080.
Gerra et al., "Clonidine and Opiate Receptor Antagonists in the Treatment of Heroin Addiction"; J. Substance Abuse Treatment (1995) vol. 12, 1, pp. 35-41.
Ghodse et al., "Opioid analgesics and Narcotic Antagonists"; Side Effects of Drugs (2000) Annual 23, chpt 8 pp. 96-113.
Glatt William, M.D. FACP, "A New Method for Detoxifying Opioid-Dependent Patients"; J. Substance Abuse Treatment (1999) vol. 17, No. 3,pp. 193-197.
Gold et al. "Rapid Opioid Detoxification During General Anesthesia"; Anesthesiology (1999) vol. 91, No. 6, pp. 1639-1647.
Goliber (Benchtop Evaluations of Tampering with Pharmaceutical Dosage Forms, Opioid Abuse Resistance Conference, Oct. 2005—Accessed from http://www.thci.org/opioid/oct05docs/TAB%205.8%20Gober.%20Benchtop%20Evaluations%20of%20Tampering%20with%20Pharmaceutical%20Disage%20Forms.pdf on Nov. 17, 2010.
Gonzalez et al., "Naltrexone: A Review of its Pharmacodynamic and Pharmacokinetic Properties and Therapeutic Efficacy in the Management of Opioid Dependence," Drugs (1988), 35:192-213.
Goodman and Gilman's The Pharmacological Basis of Therapeutics (Tenth Edition (2001), McGraw Hill.
Goodridge et al., "Factors associated with opioid dispensation for patients with COPD and lung cancer in the last year of life: A retrospective analysis," Int. J. of COPD, 2010, 5:99-105.
Greenwald et al., "Comparative Clinical Pharmacology of Short-Acting Opioids in Drug Abusers"; J. Pharm and Exper Thera (1996) vol. 277, No. 3, pp. 1228-1236.
Grimm, "Extension of the International Conference on Harmonization Tripartite Guideline for Stability Testing of New Drug Substances and Products to Countries of Climatic Zones III and IV," Drug Development and Industrial Pharmacy, vol. 24, No. 4, pp. 312-324 (1998).
Gupta et al., "Morphine Combined with Doxapram or Naloxone"; Anesthesia (1974) vol. 29, pp. 33-39.

(56) References Cited

OTHER PUBLICATIONS

Guyatt et al. "Measuring change over time: assessing the usefulness of evaluative instruments" J. Chron Dis. (1985) 40(2):171-178.
Guyatt et al., "Interpreting treatment effects in randomized trials," Br. Med. Jnl, (1998) 316(7132): 690-693.
Hagen, et al. "Efficacy, Safety, and Steady-State Pharmacokinetics of Once-A-Day Controlled-Release Morphine (MS Contin XL) in Cancer Pain," Journal of Pain and Symptom Management (2005) vol. 29, No. 1, pp. 80-90.
Han et al., "Muccoadhesive buccal disks for novel nalbuphine prodrug controlled delivery; effect of formulation variable on drug release and mucoadhesive performance"; International J. Pharm (1999) vol. 177, pp. 201-209.
Handal et al., "Naloxone"; Annals of Emergency Medicine (1983) vol. 12:7, pp. 438-445.
Hanson Analgesic, Antipyretic and Anti-Inflammatory Drugs in Remington's Science and Practice of Pharmacy (1995), 2:1207.
Harris et al., "Buprenorphine and Naloxone co-administration in opiate dependent patients stabilized on sublingual buprenorphine"; Drug and Alcohol Dependence (2000) vol. 61, pp. 85-94.
Hawkes et al., "Effect of enteric-release formulation of naloxone on intestinal transit in volunteers taking codeine"; Aliment Pharm Ther (2001) vol. 15, pp. 625-630.
Hays et al. "Assessing reliability and validity of measurement in clinical trials" in Staquet et al. (eds.) Quality of Life in Clinical Trials: Methods and Practice (1998) Oxford: Oxford University Press.
Hening et al., "Dyskinesias while awake and periodic movements in sleep in restless legs syndrome: Treatment with opioids," Neurology, vol. 36, pp. 1363-1366 (1986).
Hiroshi K., et al., "Pharmacology," Hirokawa Bookstore, 1992, p. 70-72.
Hogger et al., "Comparison of tilidine/naloxone, tramadol and bromfenac in experimental pain: a double-blind randomized crossover study in healthy human volunteers"; International J. Clin Pharm and Thera (1999) vol. 37, No. 8,pp. 377-385.
Holmes et al., "Inhibiting Spinal Dynorphin A Component Enhances Intrathecal Morphine Antinociception in Mice", Anesth. Analg. (1993), 77:1166-73.
Holzer et al., "Opioid-induced bowel dysfunction in cancer-related pain: causes, consequences and a novel approach for its management," Journal of Opioid Management, 5(3): 145-151 (2009).
Hopp et al., "Analgesic efficacy of oxycodone in combination with naloxone as prolonged release (PR) tablets in patients with moderate to severe chronic pain [abstract PT 226]," Presented at the 12th World Congress on Pain, International Association for the Study of Pain (IASP), Glasgow, Scotland, UK, MIS 4789879, Aug. 17-22, 2008.
Hopp et al., "Pain 2: Oral prolonged-release (PR) oxycodone/naloxone combination reduces opiod-induced bowel dysfunction (OIBD) in chronic pain patients [abstract 40]," Presented at the 5th Research Forum of the European Association for Palliative Care, Palliat. Med., 22(4):441 (2008).
Howes et al., "The Pharmacology of TR5109, a new Narcotic Agonist/Antagonist Analgesic"; NIDA Research (1979) pp. 99-105.
Hughes et al., "Buprenorphine for pain relief in a patient with drug abuse," The American Journal of Drug and Alcohol Abuse, vol. 17, No. 4, pp. 451-455 (1991).
Hussain et al., "Buccal and oral bioavailability of naloxone and naltrexone in rats";(1987) vol. 36, pp. 127-130.
Hussain M.A. "Improved buccal delivery of opioid analgesics and antagonists with bitterless prodrugs." Pharm. Res. 1988, 5(9):615-618.
Inoue, "On the Treatment of Restless Legs Syndrome," Progress in RLS Research, vol. 24, No. 3, pp. 892-897 (2004).
Jasinski D.R., "Assessment of the Abuse Potentiality of Morphine-like Drugs (Methods Used in Man)"; Drug Addiction (1977) pp. 197-258.
Jasinski et al., "The human pharmacology and abuse potential of N-allylnoroxymorphone naloxone"; J. Pharm and Exper Thera (1967) vol. 157, No. 2, pp. 420-426.

Johnson et al., "Buprenorphine and Naloxone for Heroin Dependence"; Substance Use Disorders (2000) pp. 519-526.
Jones et al., "Nalmefene:blockade of intravenous morphine challenge effects in opioid abuse in humans"; Drug and Alcohol Dependence (2000) vol. 60, pp. 29-37.
Judson et al., "The Naloxone Test for Opiate Dependence," Clin. Pharmacol. Ther., vol. 27, No. 4, pp. 492-501, (1980).
Kanof et al., "Clinical characteristics of naloxone-precipitated withdrawal in human opioid-dependent subjects," J. Pharmacol. Exp. Therapeut., vol. 260, No. 1, pp. 355-363 (1992).
Kanof et al., "Levels of Opioid Physical Dependence in Heroin Addicts," Drug and Alcohol Dependence, 27 (1991) 253-262.
Kapoor, S., "Emerging New Therapeutic Options for the Management of Opioid Induced Constipation," J. of Pain and Palliative Case Pharmacotherapy, 24(1):98-99 (2010).
Kazis et al. "Effects sizes for interpreting changes in health status," Med. Care 27(3 Suppl.):5178-5189 (1989).
King et al., "Naltrexone Biotransformation and Incidence of Subjective Side Effects: A Preliminary Study"; Alcoholism: Clin and Exper Res (1997) vol. 21, No. 5, pp. 906-909.
Kogan et al., "Estimation of the Systemic Availability and Other Pharmacokinetic Parameters of Naltrexone in Man after Acute and Chronic Oral Administration"; Res. Comm. in Chem. Path. and Pharm (1977) vol. 18, No. 1, pp. 29-34.
Kosten et al., "Opioid antagonist challenges in buprenorphine maintained patients"; Drug and Alcohol Dependence (1990) vol. 25, OO. 73-78.
Kosten Thomas R., M.D.,"Buprenorphine for Benzodiazepine-Abusing Heroin Addicts"; Amer J of Psychiatry (1994) vol. 1, p. 151.
Kreek et al., "Drug Interactions with Methadone," Ann. N.Y. Acad. Sci., 281, 350-371 (1976).
Krylov, Drug Register of Russia, Encyclopedia of Drugs, (2001) entries for "Nalbuphine," "Naloxone," and "Naltrexone" (English Translation).
Kurland et al., "Naloxone and the Narcotic Abuser: A Cont oiled Study of Partial Blockade"; Inter. J. of the Addictions (1974) vol. 9, No. 5, pp. 663-672.
Kurz et al., "Opioid-Induced Bowel Dysfunction: Pathophysiology and Potential New Therapies," Drugs, vol. 63, No. 7, pp. 649-671 (2003), abstract.
Lapierre "Acetaminophen Boosts Liver Toxicity Alone, as Combination Therapy-Jama" Health News Daily, vol. 18 Issue 128 dated Jul. 6, 2006.
Latasch et al. [Treatment of morphine-induced constipation with oral naloxone]. Anaesthesist. Mar. 1997;46(3):191-4. (German with English Abstract) (448EP opposition).
Leehey et al., Naloxone increases water and electrolyte excretion after water loading in patients with cirrhosis and ascites, J of lab and clin med; vol. 118, No. 5, pp. 484-491 (1991).
Leeling et al., "Disposition and metabolism of codorphone in the rat, dog, and man"; Drug Metabolism and Disposition (1982) vol. 10, No. 6, pp. 649-653.
Lehman et al.,"Influence of Naloxone on the Postoperative Analgesic and Respiratory effects of Buprenorphine"; Eur. J. Clin Pharm (1988) vol. 34, pp. 343-352.
Leidy et al., "Recommendations for evaluating the validity of quality of life claims for labeling and promotion," Value in Health 2(2): 113-127 (1999).
Levine et al., "Potentiation of Pentazocine Analgesia by Low-dose Naloxone"; J Clin Invest (1988) vol. 82, pp. 1574-1577, abstract only.
Levy M.H., Eur J Pain.vol. 5, Suppl. A, pp. 113-116 (2001), abstract.
Light et al., "Effects of Oral Morphine in Breathlessness and Exercise tolerance in Patients with Chronic Obstructive Pulmonary Disease," Am. Rev. Respir. Dis., (1989) vol. 139, pp. 126-133.
Liu et al., "Low dose oral naloxone reverses opioid-induced constipation and analgesia"; Journal of Pain and Symptom Management, vol. 23, No. 1, pp. 48-53 (2002).
Loimer et al., "Combined Naloxone/Methadone Preparations for Opiate Substitution Therapy"; J. of Substance Abuse Treatment (1991) vol. 8, pp. 157-160.
Lorcet, Physicians' Desk Reference 48th ed., 1994; pp. 2388-2390.
Lortab, Physicians' Desk Reference 48th ed., 1994; pp. 2498-2500.

(56) References Cited

OTHER PUBLICATIONS

Lowenstein et al., "Combined prolonged release oxycodone and naloxone improves bowel function in patients receiving opioids for moderate-to-severe non-malignant chronic pain: a randomized controlled trial," Expert Opinion on Pharmacotherapy, 10(4):531-543 (2009).
Martin et al. "Bioavailability Investigation of a New Tilidine/ Naloxone Liquid Formulation Compared to a Reference Formulation";Arzneim-Forsch./Drug Res. (1999) vol. 49, pp. 599-607.
Martin et al., "Demonstration of Tolerance to and Physical Dependence on N-allynormorphine (Nalorphine)";J. of Pharm and Exper Thera (1965) vol. 150, No. 3. pp. 437-442.
Medical News Today, "Oxycodone / Naloxone Combination Tablet 1-24 Reduces Opioid-induced Bowel Dysfunction in Patients With Chronic Severe Pain," Medical News Today (2007), Retrieved from Internet: URL:http://www.medicalnewstoday.com/ printerfriendlynews.php?newsid=83795, XP002636068.
Medzon, R, "Naltrexone and Nalmefene," Clinical Toxicology Review, vol. 19, No. 3, Dec. 1996.
Meissner et al., "A randomized controlled trial with prolonged-release oral oxycodone and naloxone to prevent and reverse opioid-induced constipation," Eur. J. Pain, vol. 13, pp. 56-64 (2009).
Meissner et al., "Oral naloxone reverses opioid-associated constipation", Pain, vol. 84, pp. 105-109 (2000).
Mendelson et al., "Buprenophine and naloxone Interactions in Methadone Maintenance Patients"; Society of Biological Psychiatry (1997) vol. 41, pp. 1095-1101.
Mendelson et al., "Buprenorphine and naloxone combinations: the effects of three dose ratios in morphine stabilized, opiate-dependent volunteers"; Psychopharmacology (1999) vol. 141, pp. 37-46.
Mendelson J., et al, "Buprenorphine and Naloxone Interactions in Opiate Dependent Volunteers," Clin. Phar. Ther. (1996), 60:105-114.
Miaskowski et al., "Inhibition of Spinal Opioid Analgesia by Supraspinal Administration of Selective Opioid Antagonists", Brain Research (1992), 596:41-45).
Mikus, G., "Combining Opioid Agonists and Antagonists as a Solution for Opioid-induced Constipation," European Gastroenterology and Hepatology Review, 4(2):71-74 (2008).
MIMS, Jan. 2005, pp. 120-125.
Mollereau et al., "ORL 1, a novel member of the opioid receptor family: Cloning, functional expression and localization"; FEBS letters 341 (1994), pp. 33-38.
Mueller-Lissner, "Fixed Combination of Oxycodone with Naloxone: a New Way to Prevent and Treat Opioid-Induced Constipation." Adv. Ther. (2010) 27(9):581-590.
Muller-Lissner et al., "Oral Prolonged release (PR) oxycodone/ naloxone combination reduced opioid-induced bowel dysfunction (OIBD) in patients with severe chronic pain (abstract 189)," Presented at the 2nd International Congress on Neuropathic Pain, Berlin, Germany, Published in Eur. J. Pain, 11(S1):582, Jun. 7-10, 2007.
Mundipharma Clinical Studies Report A2-3759, "Validation of Bowel Function Index," Jun. 15, 2005 (Rev. Jul. 12, 2005).
Mundipharma Clinical Studies Report OXN 2401, "Optimization of Naloxone-Oxycodone Ration in Pain Patients." Jun. 3, 2005.
Mundipharma Clinical Study Report for OXN PR Compared to OxyPR to Demonstrate Non-inferiority in Pain & Locomotor Function & Improvement in Symptoms of Constipation in OA Subjects, dated Apr. 19, 2010 (Updated Dec. 12, 2012).
Mundipharma's Opposition to Endo's Australian Patent Application No. AU2002305559, filed Oct. 1, 2008.
Nadstawek et al., "Patient assessment of a novel therapeutic approach for the treatment of severe, chronic pain," Int. J. Clin. Pract., vol. 62, No. 8, pp. 1159-1167 (2008), abstract only.
Nadstawek et al., "Patient assessment of the efficacy and tolerability of coadministered prolonged release oral oxycodone and naloxone in severe chronic pain (abstract SAT0375)," Presented at the 8th Annual European League Against Rheumatism (EULAR 2007), Barcelona, Spain, Published in Ann. Rheum. Dis., 66(Suppl. 2):543, Jun. 13-16, 2007.

Neuenschwander et al., Palliative Medicine at a Glance, 1999 (whole book).
Nichols et al., "Improved bowel function with a combination of oxycodone and naloxone (OXN) as prolonged-release (PR) tablets in patients with moderate to severe chronic pain (abstract PT225)," Presented at the 12th World Congress on Pain, International Association for the Study of Pain (IASP), Glasgow, Scotland, UK, Aug. 17-22, 2008, abstract only.
Nolte, T., "Prolonged-release oxycodone/naloxone is effective and safe in clinical use (abstract 275)," Encore presentation at the 5th Research Forum of the European Association for Palliative Care, Published in Palliative Medicine, 22(4):484-5 (2008).
Nolte, T., "Prolonged-release oxycodone/naloxone is effective and safe in cancer pain (abstract 66)," Encore presentation at the 12th World Congress on Pain, International Association for the Study of Pain (IASP), Glasgow, Scotland, UK, Aug. 17-22, 2008.
Nolte, T., "Prolonged-release oxycodone/naloxone is effective and safe in clinical use (abstract PO325)," Presented at the 28th German Congress on Cancer, Published in Onkologie, Berlin, Germany, 31(Suppl. 1):165-6, Feb. 20-23, 2008.
Norman et al., "Interpretation of changes in health-related quality of life: The remarkable universality of half a standard deviation." Med. Care 41:582-592 (2003).
Nunnally et al. Psychometric Theory (3rd Edition) NY: McGraw-Hill (1994).
Nutt et al., "Methadone-naloxone mixture for use in methadone maintenance programs"; Clin Pharm and Ther. vol. 15, No. 2., pp. 156-166 (1974).
Olesen et al., "Improvement of opioid-induced bowel dysfunction (OIBD)with oxycodone/naloxone prolonged release(OXN PR) tablets, as measured by the PAC-SYM scale," Presentation Abstract, Montreal 2010, 13th World Congress on Pain No. PH3882 Sep. 2010.
Oppermann M., "Neue Arzneimittel zur Behandlung der Opioid-induzierten Obstipation: der Mechanismus-basierte Ansatz von Methylnaltrexon, Naloxon and Alvimopan," Fortbildungstelegramm Pharmazie; May 1, 2009; pp. 117-131.
Oxygesic® Product Information, 1997-2001 (in German, w/ English translation).
Package Insert for OxyContin®, Purdue Pharma L.P. (Mar. 18, 2004).
Paille et al., "An open six-month study of the safety of Transipeg for treating constipation in community medicine," J. Clin. Res., vol. 2, pp. 65-76 (1999).
Pamuk et al., "Revalidation of description of constipation in terms of recall bias and visual scale analog questionnaire," Journal of Gastroenterology and Hepatology (2003), 18, 1417-1422.
Pappagallo, M., "Incidence, prevalence, and management of opioid bowel dysfunction," Am. J. Surg. (2001) 182 suppl. 11S-18S.
Paronis et al., "Increased Analgesic Potency of Mu Agonists after Continuous Naloxone Infusion in Rats"; J for Pharm Exper Thera (1991), 259 (2), pp. 582-589.
Parwartikar et al., "Naloxone-Mathadone Combination for the Treatment of Opiate Dependence"; Missouri Institute of Psychiatry, pp. 1350-1354, (1973).
Parwatikar et al., "Methadone-naloxone in combination for the Treatment of Heroin Addicts"; Clin. Pharm and Thera, vol. 14, No. 6, pp. 941-948, (1973).
PCT Application PCT/EP2003/003540: International Preliminary Examination Report dated Aug. 17, 2004.
PCT Application PCT/EP2003/003541: International Preliminary Examination Report dated Jul. 6, 2004.
PCT Application PCT/EP2005/006155: International Search Report dated Aug. 25, 2005 (2 pages).
PCT Application PCT/EP2006/060336: International Preliminary Report on Patentability and Written Opinion of the International Searching Authority dated May 18, 2007.
PCT Application PCT/EP2006/060341: International Preliminary Report on Patentability and Written Opinion of the International Searching Authority dated May 16, 2007.
PCT Application PCT/EP2008/062834: International Preliminary Report on Patentability and Written Opinion of the International Searching Authority dated Mar. 30, 2010.

(56) References Cited

OTHER PUBLICATIONS

PCT Application PCT/EP2009/058630: International Search Report and Written Opinion of the International Searching Authority dated Oct. 9, 2009.
PCT Application PCT/EP2011/074103: International Preliminary Report on Patentability and Written Opinion of the International Searching Authority dated Jul. 2, 2013.
PCT Application PCT/EP2011/074103: International Search Report dated Feb. 3, 2012.
Peachey et al., "Assessment of Opioid Dependence with Naloxone," British Journal of Addiction (1988) 83(2), 193-201.
Philippe et al., "Mu opoid receptor expression is increased in inflammatory bowel diseases: implications for homeostatic intestinal inflammation". GUT, vol. 55, No. 6, pp. 815-823 (2006).
Physician's Desk Reference (2001) see "Oxycontin," pp. 2697-2701.
Physician's Desk Reference (2001) see "Revia," pp. 1146-1149.
Physician's Desk Reference 48th ed.; 1994; "Talwin," 2120-2121, Montvale, NJ.
Pitts et al., "Antinociceptive and Response Rate-Altering Effects of Kappa Opioid Agonists, Spiradoline, Enadoline and U69,593, Alone and in Combination with Opioid Antagonists in Squirrel Monkeys"; J of Pharm and Exper Thera (1994) vol. 271, No. 3, pp. 1501-1508.
Poole et al., "The Effect of Sustained-Release Morphine on Breathlessness and Quality of Life in Severe Chronic Obstructive Pulmonary Disease," Am J Respir Crit Care Med, vol. 157, pp. 1877-1880 (1998).
Portenoy et al., "Breakthrough pain: characteristics and impact in patients with cancer pain," PAIN, vol. 81, No. 1-2, pp. 129-134 (1999).
Portenoy et al., "Breakthrough pain: definition, prevalence and characteristics," PAIN, vol. 41, pp. 273-281 (1990).
Press Release "International Patent Application to Be Published on Abuse-Resistant Pain Reliever Being Developed by Perdue Pharma"; Aug. 8, 2001.
Preston et al., "Abuse liability and studies of opioid agonist-antagonists in humans"; Drug and Alcohol Dependence (1991) vol. 28, pp. 49-82.
Preston et al., "Buprenorphine and Naloxone alone and in combination in Opioid-dependant Humans"; Psychopharmacology (1988), vol. 94, pp. 484-490.
Preston et al., "Differential Naltrexone Antagonism of Hydromorphone and Pentazocine Effects in Human Volunteers"; J of Pharm and Ezper Thera (1993) vol. 264, No. 2 pp. 813-823.
Preston et al., "Effects of Sublingually given naloxone in Opioid-dependant human volunteers"; Drug and Alcohol Dependence (1990) vol. 25, pp. 27-34.
Rapaka et al., "Discovery of Novel Opioid Medications"; NIDA Research Monograph 147 (1995) p. 55-83.
Rawal, et al., "An experimental study of urodynamic effects of epidural morphine and of naloxone reversal", Anesth Analg. Jul. 1983;62(7):641-647.
Reents et al., "Naloxone and Naltrexone* Application in COPD," Chest, vol. 93, No. 1, pp. 217-219 (1988).
Reimer et al., "Meeting the challenges of opioid-induced constipation in chronic pain management—a novel approach," Pharmacology, 83:10-17 (2009).
Rentz et al., "Validation of the Bowel Function Index to detect clinically meaningful changes in opioid-induced constipation," Journal of Medical Economics (JME), 12(0):371-383 (2009).
Resnick et al., "Naloxone Precipitated Withdrawal: A Method for Rapid Induction Onto Naltrexone," Clinical Pharmacology and Therapeutics, vol. 21, No. 4, pp. 409-413; received for publication Nov. 16, 1976.
Revicki et al., "Recommendation on health-related quality of life research to support labeling and promotional claims in the United States" QOL Research 9(8): 887-900 (2000).
Richter et al., "Clinical Investigation on the Development of Dependence during Oral Therapy with Tramadol"; Arzniem-Forsch/Drug Res. 35 (No. II)(1985)pp. 1742-1744.

Rosen et al., "A Pilot Study of Dextromethorphan in Naloxone-Precipitated Opiate Withdrawal"; European J. of Pharm. (1996) vol. 307, pp. 251-257.
Rosen et al., "The effect of Lamotrigine on Naloxone-precipitated Opiate withdrawal"; Drug and Alcohol Dependence (1998) vol. 52, pp. 173-176.
Rosow et al., Reversal of opioid-induced bladder dysfunction by intravenous naloxone and methylnaltrexone, Clin Pharm & Ther. vol. 82, No. 1, pp. 48-53 (2007).
Rote Liste 2004, Jan. 1, 2004; Frankfurt/Main, vol. 2004, pp. 05001-05033.
Sandner F., "Hope for patients with chronic pain: naloxone and oxycodone fixed combination offers analgesia and prevention of constipation also during sleep," J of Pham and Therapy, vol. 16; No. 6; pp. 179-180 (2007).
Sandner-Kiesling et al., "Long-term efficacy and safety of combined prolonged-release oxycodone and naloxone in the management of non-cancer chronic pain," International Journal of Clinical Practice, 64(6):763-774 (2010).
Schenck et al., "Severe, childhood-onset, idiopathic, life-long insomnia responding selectively to opiate therapy: case report with 19 year follow-up," Sleep Med., vol. 2, No. 6, pp. 531-536 (2001).
Schenck et al., Letter to the Editor, Sleep Med., vol. 4, No. 3, p. 251 (2003).
Schmidt, W.K. "Alvimopan (ADL 8-2698) is a Novel Peripheral Opioid Antagonist," The American Journal of Surgery, 182 (Suppl. to Nov. 2001) 27S-38S (2001).
Schuh et al., "Buprenorphine, Morphine and Naloxone Effects during Ascending Morphine Maintenance in Humans"; J. Pharm and Exper Thera (1996) vol. 278, 2, pp. 836-846.
Schuh et al., "Onset, Magnitude and Duration of Opioid Blockade Produced by Buprenorphine and Naltrexone in Humans"; Psychopharmacology (1999) vol. 145, pp. 162-174.
Schutter et al., "Innovative pain therapy with a fixed combination of prolonged-release oxycodone/naloxone: a large observational study under conditions of daily practice," Current Medical Research and Opinion, 26(6):1377-1387 (2010).
Shen et al., "Ultra-Low Doses of Naltrexone or Etorphine Increase Morphine's Antinocieceptive Potencey and Attenuate Tolerance/Dependence in Mice," Brain Research (1997), 757:176-190.
Shin Yakuzaigaku Soron (3rd revised edition), 1987, p. 148-151.
Simpson et al., "Fixed-ratio combination oxycodone/naloxone compared with oxycodone alone for the relief of opiod induced constipation in moderate-to-severe non-cancer pain," Current Medical Research and Opinion (CMRO), 24(12):3503-3512 (2008).
Smith et al., "Low-dose naltrexone as a treatment for active Crohn's disease," AGA Abstracts, S1397, XP009095749, p. A-218 (2006).
Smith et al., "Low-dose naltrexone therapy improves active Crohn's disease," The American Journal of Gastroenterology, vol. 102, No. 4 pp. 820-828 (2007).
Smith et al., "Single and multiple-dose pharmacokinetic evaluation of oxycodone and naloxone in an opioid agonist/antagonist prolonged-release combination in healthy adult volunteers," Clinical Therapeutics, 30(11):2051-2068 (2008).
Smith et al., "Prolonged-release oxycodone/naloxone tablets: Dose-proportional pharmacokinetics (abstract PW 256)," Presented at the 12th World Congress on Pain, International Association for the Study of Pain (IASP), Glasgow, Scotland, UK (MIS 4790606), Aug. 17-22, 2008.
Stevens et al., Nonspecific Excitatory Effects of Morphine: Reverse-Order Precipitated Withdrawal and Dose-Dose Interactions: Psychopharmacology (1981) vol. 75, pp. 210-211.
Stine et al., "Reduction of Opiate Withdrawal-like Symptoms by Cocaine Abuse during Methadone and Buprenorphine Maintenance"; Am. J. Drug and Alcohol Abuse (1994) vol. 20, 4, pp. 445-458.
Stine et al., "Use of Drug Combinations in Treatment of Opioid Withdrawal"; J. Clinical Psych. (1992) vol. 12, No. 3, pp. 203-209.
Stoller et al., "Effects of buprenorphine/naloxone in opioid-dependent humans" Psychopharmacology (2001) vol. 154, pp. 230-242.
Strain et al., "Acute Effects of Buprenorphine, hydromorphone and naloxone in methadone-maintained volunteers"; J. Pharm and Exper Thera (1992) vol. 261, No. 3, pp. 985-993.

(56) References Cited

OTHER PUBLICATIONS

Strain et al., "Effects of buprenorphine versus buprenorphine/naloxone tablets in non-dependent opioid abusers"; Psychopharmacology (2000) vol. 148, pp. 374-383.
Strain et al., "Opioid antagonist effects of dezocine in opioid-dependent humans"; Clin Pharm and Thera (1996) vol. 60, No. 2, pp. 206-217.
Strain et al., "Precipitated Withdrawal by Pentazocine in Methadone-Maintained Volunteers"; J. Pharm and Exper Thera (1993) vol. 267, No. 2, pp. 624-634.
Sunshine et al., "Analgesic Efficacy of Pentazocine Versus a Pentazocine-Naloxone Combination Following Oral Administration," Clin. J. Pain (1988), 4:35-40.
Suzuki et al., "Morphine conditioned place preference after chronic treatment with naloxone in the rat"; Research Communications in Substance Abuse (1991) vol. 12., No. 3., pp. 119-131.
Sykes "An investigation of the ability of oral naloxone to correct opioid-related constipation in patients with advanced cancer," Palliative Medicine (1996), 10:134-144.
Sykes "Oral naloxone in opioid-associated constipation," Lancet (1991) vol. 337 p. 1475.
Sykes, N.P., "Using Oral Naloxone in Management of Opioid Bowel Dysfunction," in Handbook of Opioid Bowel Syndrome, Chapter 9, (Yuan, C.-S. ed., The Haworth Medical Press 2005).
Tai et al., "Naltrexone: An Antagonist Therapy for Heroin Addiction"; NIDA (1997) 5 pages.
Trzepacz et al., "Response to Opioids in Three Patients with Restless Legs Syndrome," Am. J. Psychiatry, vol. 141, pp. 993-999 (1984).
U.S. Appl. No. 60/290,439, filed May 11, 2001.
Umbricht et al., "Naltrexone shortened opioid detoxification with buprenorphine"; Drug and Alcohol Dependence (1999) vol. 56 pp. 181-190.
Vaccarino et al., "Endogenous Opiates: 1999"; Peptides 21 (2000) pp. 1975-2034.
Vaccarino et al.,"Analgesia Produced by Normal Doses of Opioid Antagonists Alone and in Combination with Morphine", Pain (1989), 36:103-109.
Valoron® Product Information, 1997-2001 (in German, w/ English translation).
Vicodin, Physicians' Desk Reference 48th ed., 1994; pp. 1143-1145.
Vondrackova et al. "Analgesic efficacy and safety of oxycodone in combination with naloxone as prolonged release tablets in patients with moderate to severe chronic pain," Journal of Pain, vol. 9, No. 12 pp. 1144-1154 (2008).
Walsh et al., "Effects of Naltrexone on Response to Intravenous Cocain, Hydromorphone and their Combination in Humans," (1996).
Walters et al., "Successful Treatment of the Idiopathic Restless Legs Syndrome in a Randomized Double-Blind Trial of Oxycodone Versus Placebo," Sleep, vol. 16, No. 4, pp. 327-332 (1993).
Wang et al., "cDNA cloning of an orphan opiate receptor gene family member and its splice variant"; FEBS letters 348 (1994) pp. 75-79.
Wang et al., "Crossover and Parallel Study of Oral Analgesics," J. Clin. Pharmacol (1981), 21:162-168.
Wang et al., "Inverse Agonists and neutral antagonists at mu opioid receptor (MOR): possible role of basal receptor signaling in narcotic dependence"; J. Neurochemistry (2001) vol. 77, pp. 1590-1600.
Wang et al., "Rating the Presence and Severity of Opiate Dependence," Clinical Pharmacology and Therapeutics, vol. 16, No. 4, pp. 653-657; received for publication Jan. 21, 1974.
Watkins et al. "Aminotransferase Elevations in Healty Adults Receiving 4 Grams of Acetaminophen Daily" Jama, Jul. 5, 2006 vol. 296 No. 1.
Way et al., "Responsivity to Naloxone during Morphine Dependence"; Annals New York Academy of Sciences, pp. 252-261, (1976).
Weinberg et al., "Sublingual absorption of selected opioid analgesics"; Clin Pharm Thera (1988) vol. 44, No. 3, pp. 335-342.
Weinhold et al., "Buprenorphine Alone and in Combination with Naltrexone in Non-Dependent Humans," Drug and Alcohol Dependence (1992), 30:263-274.

Wells et al., "In vivo Pharmacological Characterization of SoRI 9409, a Nonpeptidic Opioid-Agonist/ -Antagonist that Produces Limited Antinociceptive Tolerance and Attenuates Morphione Physical Dependence"; J. Pharm and Exper Thera (2001) vol. 297, No. 2, pp. 597-605.
Wiesen et al., "The Safety and Value of Naloxone as a Therapeutic Aid," Drug and Alcohol Dependence, 2 (1977) pp. 123-130.
Wikler et al., "N-Allylnormorphine: Effects of single dose and Precipitation of Acute "Abstinence Syndromes" during addiction to morphine, methadone or heroin in man (post addicts)"; N-Allylnormorphine During Narcotic Addiction (1953) pp. 8-20.
Wilkinson "The Dynamics of Drug Absorption, Distribution, and Elimination," Goodman and Gilman's The Pharmacological Basis of Therapeutics, Chapter 1, Pharmacokinetics, copyright page and pp. 3-29 (2001).
Wilmington, Del., PR Newswire; New Data Published Describing Favorable Safety Profile of REVIA (Naltrexone Hydrochloride Tablets) When Used to Treat Alcohol Dependence, Dec. 1997.
Wodak Alex, "Drug Treatment for Opioid Dependence"; Australian Prescriber (2001) vol. 24, No. 1, pp. 4-6.
Woodcock et al., "Effects of Dihydrocodeine, Alcohol, and Caffeine on Breathlessness and Exercise Tolerance in Patients with Chronic Obstructive Lung Disease and Normal Blood Cases," N. Engl. J. Med., (1981) vol. 305, No. 27, pp. 1611-1616.
Woodcock et al., Correspondence, N. Engl. J. Med., (1982) vol. 306, pp. 1363-1364.
Woodward et al., "Prolonged-release oxycodone/naloxone tablets: Pharmacokinetics in the elderly (abstract)," Presented at the 12th World Congress on Pain, International Association for the Study of Pain (IASP), Glasgow, Scotland, UK, Abstract PW 255, (MIS 4789067), Aug. 17-22, 2008.
Wright et al., "Acute physical dependence in Humans; repeated naloxone-precipitated withdrawal after a single-dose of methadone"; Drug and Alcohol Dependence (1991) vol. 27, pp. 139-148.
Wyrwich et al. "Further evidence supporting an SEM-based criterion for identifying meaningful intra-individual changes in health-related quality of life" J. Clin. Epidemiol. 52:861-873 (1991).
Yoburn et al., "Opioid Antagonist-induced Receptor Upregulation: Effects of Concurrent Agonist Administration"; Brain Research Bulletin (1994), vol. 33, pp. 237-240.
Yoburn et al., "Supersensitivity to Opioid Analgesics Following Chronic Opioid Antagonist Treatment: Relationship to Receptor Sensitivity"; Pharmacology Bio Beh (1995) vol. 51 No. 2, pp. 535-539.
Yuan et al., "Efficacy of Orally Administered Methylnaltrexone in Decreasing Subjective Effects After Intravenous Morphine", Drug and Alcohol Dependence (1998); 52:161-165.
Yuan et al., "The Safety and Efficacy of Oral Methylnaltrexone in Preventing Morphine-induced Delay in Oral-Cecal Transit Time", Clinical Trials and Therapeutics (1997), 61:467-475.
Zaks et al., "Naloxone Treatment of Opiate Dependence"; JAMA (1971) vol. 215, No. 13, pp. 2108-2110.
Zech et al., "Validation of World Health Organization Guidelines for Cancer Pain Relief: a 10-year Prospective Study," Pain, Oct. 1995:63(1):65-76.
Zeppetella et al., "Opioids for cancer breakthrough pain: A pilot study reporting patient assessment of time to meaningful pain relief," J of Pain and Symptom Management, vol. 35, No. 5, pp. 563-567 (2008).
Zhang et al., "Down-Regulation of -Opioid Receptors in Rat and Monkey Dorsal Root Ganglion Neurons and Spinal Cord After Peripheral Axotomy"; Neuroscience (1998) vol. 82., pp. 223-240.
Zhou et al. "A clinical analysis of 18 cases of naloxone treating pruritis due to cholestia, hebei," Modern Journal of Integrated Chinese and Western Medicine, vol. 8, No. 1, p. 43 (1999) (English translation).
Zhu et al., "Naltrexone-precipitated morphine withdrawal in infant rat is attenuated by acute administration if NOS inhibitors but not NMDA receptor antagonists"; Psychopharmacology (2000) vol. 150, pp. 325-336.

* cited by examiner

US 9,271,940 B2

IMMEDIATE RELEASE PHARMACEUTICAL COMPOSITIONS COMPRISING OXYCODONE AND NALOXONE

CROSS REFERENCE TO RELATED APPLICATIONS

This application claims priority under 35 U.S.C. §§119(a)-(d) and 365(b) of European Patent Application No. EP 09154805.7, filed 10 Mar. 2009, the contents of all of which are incorporated herein in their entireties by reference thereto.

FIELD OF THE INVENTION

The present invention pertains to pharmaceutical compositions suitable for treating patients suffering from pain.

BACKGROUND OF THE INVENTION

The importance of adequately treating patients suffering from pain has been increasingly recognized over the past decade.

For the treatment of chronic moderate to strong and even severe pain as it occurs in cancer patients, opioid analgesics have become increasingly popular over the last decades. Among the factors contributing to this development has been the introduction of controlled release preparations of opioids such as morphine, hydromorphone and oxycodone which can be taken by a patient at reduced frequency compared to the immediate release preparations of these agents which had been available before.

Controlled release preparations of the opioid oxycodone such as the product Oxygesic® tablets which comprises oxycodone hydrochloride as the active agent and Targin® tablets which comprises a combination of oxycodone hydrochloride and the opioid antagonist naloxone hydrochloride have been successful both from a commercial perspective and in terms of acceptance by patients and medical practitioners.

However, there remain situations where controlled release preparations of opioids may not necessarily be medications of first choice when treating patients suffering from pain.

OBJECTIVE AND SUMMARY OF THE INVENTION

It is one objective of the present invention to provide pharmaceutical compositions suitable for the treatment of pain and in particular for the treatment of chronic moderate to strong and even severe pain which can be used for titrating patients suffering from pain and/or treating breakthrough pain in patients suffering from pain while concomitantly avoiding undesired side effects as they may occur during standard pain therapy.

These and other objectives as they will become apparent from the ensuing description are attained by the subject-matter of the independent claims. The dependent claims as set forth hereinafter refer to some of the preferred embodiments of the present invention.

The present invention in one embodiment relates to an oral immediate release pharmaceutical composition comprising at least oxycodone or a pharmaceutically acceptable salt thereof and naloxone or a pharmaceutically acceptable salt thereof in about a 2:1 ratio (oxycodone or a pharmaceutically acceptable salt thereof: naloxone or a pharmaceutically acceptable salt thereof) by weight.

Generally, oral immediate release pharmaceutical compositions in accordance with the present invention may comprise other pharmaceutically active agents in addition to oxycodone or a pharmaceutically acceptable salt thereof and naloxone or a pharmaceutically acceptable salt thereof. However, it can be a preferred embodiment of the present invention that oxycodone or a pharmaceutically acceptable salt thereof and naloxone or a pharmaceutically acceptable salt thereof are the sole pharmaceutically active agents of pharmaceutical compositions in accordance with the present invention.

Generally, oral immediate release pharmaceutical compositions in accordance with the present invention may comprise oxycodone in the form of its free base or a salt thereof and naloxone in the form of its free base or a salt thereof. However, it can be preferred that oral immediate release pharmaceutical compositions in accordance with the invention comprise oxycodone in the form of oxycodone hydrochloride and naloxone in the form of naloxone hydrochloride. It may be an even more preferred embodiment that oxycodone hydrochloride and naloxone hydrochloride form the sole pharmaceutically active agents of the pharmaceutical composition.

In a first aspect, oral immediate release pharmaceutical compositions in accordance with the invention comprise an amount of oxycodone or a pharmaceutically acceptable salt thereof equivalent to about 1 mg to about 160 mg of oxycodone hydrochloride and an amount of naloxone or a pharmaceutically acceptable salt thereof equivalent to about 0.5 mg to about 80 mg of naloxone hydrochloride. In one of the preferred embodiments, oral immediate release pharmaceutical compositions in accordance with the invention may comprise an amount of oxycodone or a pharmaceutically acceptable salt thereof equivalent to about 2.5 mg to about 20 mg of oxycodone hydrochloride and an amount of naloxone or a pharmaceutically acceptable salt thereof equivalent to about 1.25 mg to about 10 mg of naloxone hydrochloride. These pharmaceutical compositions may comprise the pharmaceutically active agents in about a 2:1 ratio by weight.

A preferred embodiment of this first aspect can relate to oral immediate release pharmaceutical compositions comprising oxycodone hydrochloride and naloxone hydrochloride as the sole pharmaceutically active agents in about a 2:1 ratio (oxycodone hydrochloride:naloxone hydrochloride) with oxycodone hydrochloride being present in an amount of about 2.5 mg to about 40 mg of oxycodone hydrochloride and with naloxone hydrochloride being present in an amount of about 1.25 mg to about 20 mg of naloxone hydrochloride.

An even more preferred embodiment of this first aspect can relate to oral immediate release pharmaceutical compositions comprising oxycodone hydrochloride and naloxone hydrochloride as the sole pharmaceutically active agent in about a 2:1 ratio (oxycodone hydrochloride:naloxone hydrochloride) with oxycodone hydrochloride being present in an amount of about 2.5 mg to about 20 mg of oxycodone hydrochloride and with naloxone hydrochloride being present in an amount of about 1.25 mg to about 10 mg of naloxone hydrochloride.

A second aspect of the present invention relates to oral immediate release pharmaceutical compositions which comprise oxycodone or a pharmaceutically acceptable salt thereof and naloxone or a pharmaceutically acceptable salt thereof in about a 2:1 ratio (oxycodone or pharmaceutically acceptable salt thereof: naloxone or a pharmaceutically acceptable salt thereof) by weight and wherein the formulation releases in vitro, when measured using the Ph. Eur. Paddle Method at 100 rpm in 0.1 N hydrochloric acid at 37° C. and using UV detection at 230 nm, ≥75% of oxycodone or a pharmaceutically acceptable salt thereof by weight and ≥75% of naloxone or a pharmaceutically acceptable salt thereof by weight at 45 min.

A preferred embodiment of this second aspect can relate to oral immediate release pharmaceutical compositions which comprise oxycodone or a pharmaceutically acceptable salt thereof and naloxone or a pharmaceutically acceptable salt thereof in about a 2:1 ratio (oxycodone or a pharmaceutically acceptable salt thereof to naloxone or a pharmaceutically acceptable salt thereof) by weight, wherein the formulation releases in vitro, when measured using the Ph. Eur. Paddle Method at 100 rpm in 0.1 N hydrochloric acid at 37° C. and using UV detection at 230 nm, ≥80% of oxycodone or a pharmaceutically acceptable salt thereof by weight and ≥80% of naloxone or a pharmaceutically acceptable salt thereof by weight at 15 min.

A more preferred embodiment of this second aspect can relate to oral immediate release pharmaceutical compositions which comprise oxycodone or a pharmaceutically acceptable salt thereof and naloxone or a pharmaceutically acceptable salt thereof in about a 2:1 ratio (oxycodone or a pharmaceutically acceptable salt thereof to naloxone or a pharmaceutically acceptable salt thereof) by weight, wherein the formulation releases in vitro, when measured using the Ph. Eur. Paddle Method at 100 rpm in 0.1 N hydrochloric acid at 37° C. and using UV detection at 230 nm, ≥90% of oxycodone or a pharmaceutically acceptable salt thereof by weight and ≥90% of naloxone or a pharmaceutically acceptable salt thereof by weight at 15 min.

A even more preferred embodiment of this second aspect can relate to oral immediate release pharmaceutical compositions which comprise oxycodone or a pharmaceutically acceptable salt thereof and naloxone or a pharmaceutically acceptable salt thereof in about a 2:1 ratio (oxycodone or a pharmaceutically acceptable salt thereof to naloxone or a pharmaceutically acceptable salt thereof) by weight, wherein the formulation releases in vitro, when measured using the Ph. Eur. Paddle Method at 100 rpm in 0.1 N hydrochloric acid at 37° C. and using UV detection at 230 nm, ≥95% of oxycodone or a pharmaceutically acceptable salt thereof by weight and ≥95% of naloxone or a pharmaceutically acceptable salt thereof by weight at 15 min.

In all embodiments of the second aspect, oral immediate release pharmaceutical compositions may comprise an amount of oxycodone or a pharmaceutically acceptable salt thereof equivalent to about 1 mg to about 160 mg of oxycodone hydrochloride and an amount of naloxone or a pharmaceutically acceptable salt thereof equivalent to about 0.5 mg to about 80 mg of naloxone hydrochloride.

Amounts of oxycodone or a pharmaceutically acceptable salt thereof equivalent to about 1 mg to about 80 mg of oxycodone hydrochloride and an amount of naloxone or a pharmaceutically acceptable salt thereof equivalent to about 0.5 mg to about 40 mg of naloxone hydrochloride, amounts of oxycodone or a pharmaceutically acceptable salt thereof equivalent to about 1 mg to about 40 mg of oxycodone hydrochloride and an amount of naloxone or a pharmaceutically acceptable salt thereof equivalent to about 0.5 mg to about 20 mg of naloxone hydrochloride or amounts of oxycodone or a pharmaceutically acceptable salt thereof equivalent to about 1 mg to about 20 mg of oxycodone hydrochloride and an amount of naloxone or a pharmaceutically acceptable salt thereof equivalent to about 0.5 mg to about 10 mg of naloxone hydrochloride may be even more preferred.

In a third aspect of the present invention, an oral immediate release pharmaceutical composition may comprise oxycodone or a pharmaceutically acceptable salt thereof and naloxone or a pharmaceutically acceptable salt thereof, wherein the composition is in solid form and wherein the formulation releases in vitro, when measured using the Ph. Eur. Paddle Method at 100 rpm in 0.1 N hydrochloric acid at 37° C. and using UV detection at 230 nm, ≥75% of oxycodone or a pharmaceutically acceptable salt thereof by weight and ≥75% of naloxone or a pharmaceutically acceptable salt thereof by weight at 15 min.

A preferred embodiment of this third aspect can relate to oral immediate release pharmaceutical compositions, wherein the formulation releases in vitro, when measured using the Ph. Eur. Paddle Method at 100 rpm in 0.1 N hydrochloric acid at 37° C. and using UV detection at 230 nm, ≥80% of oxycodone or a pharmaceutically acceptable salt thereof by weight and ≥80% of naloxone or a pharmaceutically acceptable salt thereof by weight at 15 min.

A more preferred embodiment of this third aspect can relate to oral immediate release pharmaceutical compositions, wherein the formulation releases in vitro, when measured using the Ph. Eur. Paddle Method at 100 rpm in 0.1 N hydrochloric acid at 37° C. and using UV detection at 230 nm, ≥90% of oxycodone or a pharmaceutically acceptable salt thereof by weight and ≥90% of naloxone or a pharmaceutically acceptable salt thereof by weight at 15 min.

An even more preferred embodiment of this third aspect can relate to oral immediate release pharmaceutical compositions, wherein the formulation releases in vitro, when measured using the Ph. Eur. Paddle Method at 100 rpm in 0.1 N hydrochloric acid at 37° C. and using UV detection at 230 nm, ≥95% of oxycodone or a pharmaceutically acceptable salt thereof by weight and ≥95% of naloxone or a pharmaceutically acceptable salt thereof by weight at 15 min.

In all embodiments of the third aspect, oral immediate release pharmaceutical compositions may comprise an amount of oxycodone or a pharmaceutically acceptable salt thereof equivalent to about 1 mg to about 160 mg of oxycodone hydrochloride and an amount of naloxone or a pharmaceutically acceptable salt thereof equivalent to about 0.5 mg to about 80 mg of naloxone hydrochloride.

Amounts of oxycodone or a pharmaceutically acceptable salt thereof equivalent to about 1 mg to about 80 mg of oxycodone hydrochloride and an amount of naloxone or a pharmaceutically acceptable salt thereof equivalent to about 0.5 mg to about 40 mg of naloxone hydrochloride, amounts of oxycodone or a pharmaceutically acceptable salt thereof equivalent to about 1 mg to about 40 mg of oxycodone hydrochloride and an amount of naloxone or a pharmaceutically acceptable salt thereof equivalent to about 0.5 mg to about 20 mg of naloxone hydrochloride or amounts of oxycodone or a pharmaceutically acceptable salt thereof equivalent to about 1 mg to about 20 mg of oxycodone hydrochloride and an amount of naloxone or a pharmaceutically acceptable salt thereof equivalent to about 0.5 mg to about 10 mg of naloxone hydrochloride may be even more preferred.

In all embodiments of the third aspect, the pharmaceutical composition may comprise a disintegrant and optionally a filler and optionally other pharmaceutically acceptable excipients. Preferably, one can use a combination of e.g. starch and lactose as disintegrant. Lactose alone may at the same time function as a filler. A particularly preferred embodiment relies on the product Starlac®, a combination of lactost 85% and starch 15%, which may function both as a disintegrant and as a filler. Different types of disintegrants, fillers or other types of pharmaceutically acceptable excipients are set forth hereinafter. The combined filler/disintegrant may be comprised within the pharmaceutical composition in an amount of about 40% to about 90%, preferably in an amount of about 50% to about 85% and even more preferably in an amount of about 60% to about 80% by weight based on the weight of the composition. These numbers particularly apply if an excipient having a dual function both as a disintegrant and a filler such as Starlac® is used.

In all embodiments of the third aspect, the pharmaceutical composition may comprise oxycodone or a pharmaceutically acceptable salt thereof and naloxone or a pharmaceutically acceptable salt thereof in about a 2:1 ratio (oxycodone or a pharmaceutically acceptable salt thereof to naloxone or a pharmaceutically acceptable salt thereof) by weight.

In all embodiments of the third aspect of the invention, the pharmaceutical composition may be provided in the form of tablets, capsules, granules, multiparticulates and the like. Tablets can be particularly preferred.

Of the oral immediate release pharmaceutical compositions of the invention which comprise an amount of oxycodone or a pharmaceutically acceptable salt thereof equivalent to about 2.5 mg to about 20 mg of oxycodone hydrochloride and an amount of naloxone or a pharmaceutically acceptable salt thereof equivalent to about 1.25 mg to about 10 mg of naloxone hydrochloride in a ratio of about 2:1 by weight, those can be preferred which provide for an AUCt of oxycodone in the range of about 15 ng·h/mL to about 500 ng·h/mL, preferably in the range of about 20 ng·h/mL to about 400 ng·h/mL, more preferably in the range of about 25 ng·h/mL to about 300 ng·h/mL and even more preferably in the range of about 30 ng·h/mL to about 250 ng·h/mL when administered in a single dose study in human healthy volunteers. Such oral immediate release pharmaceutical compositions may preferably comprise the hydrochloride salts of oxycodone and naloxone.

Of the oral immediate release pharmaceutical compositions of the invention which comprise an amount of oxycodone or a pharmaceutically acceptable salt thereof equivalent to about 2.5 mg to about 20 mg of oxycodone hydrochloride and an amount of naloxone or a pharmaceutically acceptable salt thereof equivalent to about 1.25 mg to about 10 mg of naloxone hydrochloride in a ratio of about 2:1 by weight, those can be preferred which provide for a Cmax of oxycodone in the range of about 1 ng/mL to about 300 ng/mL, preferably in the range of about 2 ng/mL to about 200 ng/mL, more preferably in the range of about 3 ng/mL to about 100 ng/mL, even more preferably in the range of about 4 ng/mL to about 75 ng/mL and most preferably in the range of about 6 ng/mL to about 50 ng/mL when administered in a single dose study in human healthy volunteers. Such oral immediate release pharmaceutical compositions may preferably comprise the hydrochloride salts of oxycodone and naloxone.

The oral immediate release pharmaceutical compositions in accordance with the invention may be in the form of, but are not limited to, a tablet, a capsule, multiparticulates, e.g. granules, spheroids or beads, and liquids, e.g a solution, suspension, or emulsion.

Oral immediate release pharmaceutical compositions in accordance with the invention may comprise at least a diluent and optionally a disintegrant as pharmaceutically acceptable excipients. Further, they may comprise other pharmaceutically acceptable excipients such as lubricants, fillers, colourants, flavourants, pH-adjusters, plasticizers, anti-tack agents, binders and the like. Oral immediate release pharmaceutical compositions in accordance with the invention may also comprise at least a disintegrant and optionally a diluent as pharmaceutically acceptable excipients. Further they may comprise other pharmaceutically acceptable excipients such as lubricants, fillers, colourants, flavourants, pH-adjusters, plasticizers, anti-tack agents, binders and the like. It is to be understood that one preferably can use excipients which have dual function both as a disintegrant and a diluent such as the Starlac® product.

In a particularly preferred embodiment of the present invention, an oral immediate release pharmaceutical composition comprises about 2.5 mg to about 20 mg of oxycodone hydrochloride and about 1.25 mg to about 10 mg of naloxone hydrochloride in about a 2:1 ratio (oxycodone hydrochloride: naloxone hydrochloride) by weight, wherein the composition comprises oxycodone hydrochloride and naloxone hydrochloride as the sole pharmaceutically active agents, wherein the composition is in the form of a tablet, wherein the formulation comprises at least a diluent and optionally a disintegrant as pharmaceutically acceptable excipients and wherein the formulation releases in vitro, when measured using the Ph. Eur. Paddle Method at 100 rpm in 0.1 N hydrochloric acid at 37° C. and using UV detection at 230 nm, ≥80% of oxycodone or a pharmaceutically acceptable salt thereof by weight and ≥80% of naloxone or a pharmaceutically acceptable salt thereof by weight at 45 min. In a further preferred aspect of these particularly preferred embodiments of the present invention, a pharmaceutical composition may release in vitro, when measured using the Ph. Eur. Paddle Method at 100 rpm in 0.1 N hydrochloric acid at 37° C. and using UV detection at 230 nm, ≥95% of oxycodone hydrochloride and ≥95% of naloxone hydrochloride by weight at 15 min.

Another aspect of these particularly preferred embodiments of the present invention relates to pharmaceutical compositions which provide for an AUCt of oxycodone in the range of about 25 ng·h/mL to about 300 ng·h/mL and more preferably in the range of about 30 ng·h/mL to about 250 ng·h/mL when administered in a single dose study in human healthy volunteers. Such oral immediate release pharmaceutical compositions may preferably comprise the hydrochloride salts of oxycodone and naloxone.

Another aspect of these particularly preferred embodiments of the present invention relates to pharmaceutical compositions which provide for a Cmax of oxycodone in the range of about 4 ng/mL to about 75 ng/mL and more preferably in the range of about 6 ng/mL to about 50 ng/mL when administered in a single dose study in human healthy volunteers. Such oral immediate release pharmaceutical compositions may preferably comprise the hydrochloride salts of oxycodone and naloxone. Pharmaceutical compositions which provide in addition the AUC values of the preceding paragraph are particularly preferred.

Oral immediate release pharmaceutical compositions in accordance with the invention can be used for titrating patients suffering from pain, in particular those suffering from chronic moderate to strong and even severe pain.

Oral immediate release pharmaceutical compositions in accordance with the invention can also be used for treating breakthrough pain in patients suffering from pain, in particular those suffering from chronic moderate to strong and even severe pain.

Oral immediate release pharmaceutical compositions in accordance with the invention can also be used to treat pain and in particular chronic moderate to strong and even severe pain in patients suffering from pain.

The present invention also relates to the use of oral immediate release pharmaceutical compositions as described above and the manufacture of a medicament for titrating patients suffering from pain, in particular those suffering from chronic moderate to strong and even severe pain.

Further, the present invention relates to the use of oral immediate release pharmaceutical compositions as described above and the manufacture of a medicament for treating breakthrough pain in patients suffering from pain, in particular in those suffering from chronic moderate to strong and even severe pain.

Further, the present invention relates to the use of an oral immediate release pharmaceutical composition as described above and the manufacture of a medicament for treating pain in patients suffering from pain, in particular in those suffering from chronic moderate to strong and even severe pain.

The present invention in another aspect relates to a method of titrating a patient suffering from pain, in particular from chronic moderate to strong and even severe pain, by administering an oral immediate release pharmaceutical composition as described above.

Yet another aspect of the present invention relates to a method of treating breakthrough pain in a patient suffering from pain, in particular from chronic moderate to strong and even severe pain, by administering an oral immediate release pharmaceutical composition as described above.

Yet another aspect of the present invention relates to a method of treating pain, in particular chronic moderate to strong and even severe pain, in patients suffering from pain, by administering an oral immediate release pharmaceutical composition as described above.

Further, the present invention relates to a method of manufacturing an oral immediate release pharmaceutical composition as described above.

FIGURE LEGENDS

DETAILED DESCRIPTION OF THE INVENTION

Figure 1:
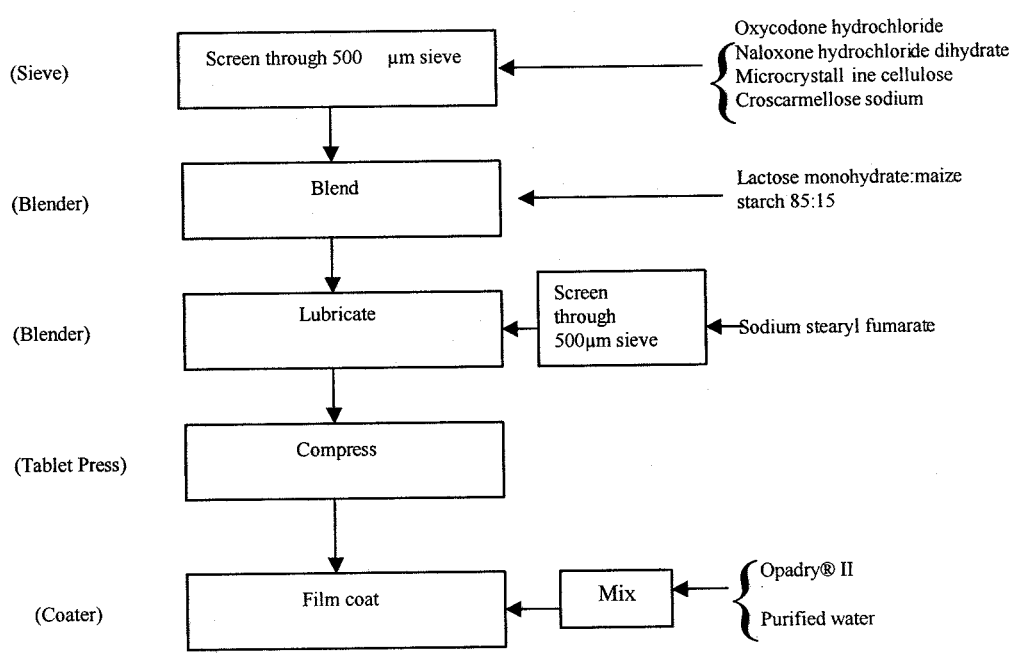
FIG. 1 depicts a flow chart of a manufacturing process for pharmaceutical compositions of the invention.

The present invention as illustratively described in the following may suitably be practised in the absence of any element or elements, limitation or limitations, not specifically disclosed herein.

The present invention will be described with respect to particular embodiments and with reference to certain figures but the invention is not limited thereto but only by the claims. The figures as described are only schematic and non-limiting. Terms as set forth hereinafter are generally to be understood in their common sense unless indicated otherwise.

Where the term "comprising" is used in the present description and claims, it does not exclude other elements. For the purposes of the present invention, the term "consisting of" is considered to be a preferred embodiment of the term "comprising of". If hereinafter a group is defined to comprise at least a certain number of embodiments, this is also to be understood to disclose a group which preferably consists only of these embodiments.

Where an indefinite or definite article is used when referring to a singular noun, e.g. "a", "an" or "the", this includes a plural of that noun unless something else is specifically stated. The terms "about" or "approximately" in the context of the present invention denote an interval of accuracy that the person skilled in the art will understand to still ensure the technical effect of the feature in question. The term typically indicates deviation from the indicated numerical value of ±10%, and preferably of ±5%.

If in the following reference is made to oxycodone or naloxone, this always also includes the reference to a pharmaceutically acceptable salt of the free base of oxycodone or a pharmaceutically acceptable salt of the free base of naloxone or to derivatives thereof unless it is specifically indicated that the term "oxycodone" or "naloxone" should only refer to the free base.

The term "immediate release" refers to the release rate by which the active ingredients, i.e. oxycodone or a pharmaceutically acceptable salt thereof and naloxone or a pharmaceutically acceptable salt thereof, are released from the pharmaceutical composition. In line with the general understanding, the term "immediate release" refers to pharmaceutical compositions showing a release of the active substance(s) which is not deliberately modified by a special formulation design and/or manufacturing methods.

The term "immediate release" in particular refers to the property that pharmaceutical compositions in accordance with the invention release in vitro, when measured using the Ph. Eur. Paddle Method at 100 rpm in 0.1 N hydrochloric acid at 37° C. and using UV detection at 230 nm, ≥75% of oxycodone or a pharmaceutically acceptable salt thereof by weight and ≥75% of naloxone or a pharmaceutically acceptable salt thereof by weight at 45 min.

The in vitro release rates are determined according to the European Pharmacopeia (Ph. Eur.) Paddle method as described in the Ph. Eur. 2.9.3 $6^{th}$ edition. The paddle speed is set at 100 rpm in simulated gastric fluid (USP (United States Pharmacopeia without pepsin)) dissolution medium. Aliquots of the dissolution media are withdrawn at 15 minutes and 45 minutes and analysed by HPLC using a reverse phase Merck LiChrospher 60 RP Select B column maintained at 60° C. The mobile phase consists of 85:15 v/v; pH 2.0 potassium chloride:methanol. Ultraviolet detection takes place at 230 nm. Oxycodone and naloxone are quantified by an external standard assay.

If the oral immediate release pharmaceutical dosage form comprises an amount of oxcodone or a pharmaceutically acceptable salt thereof equivalent to an amount of up to 5 mg of oxycodone hydrochloride and an amount of naloxone or a pharmaceutically acceptable salt thereof equivalent to an amount of up to 2.5 mg of naloxone hydrochloride, the Ph. Eur. paddle test is performed in 500 ml of 0.1 N hydrochloric acid.

If the oral immediate release pharmaceutical dosage form comprises an amount of oxcodone or a pharmaceutically acceptable salt thereof equivalent to an amount of more than 5 mg of oxycodone hydrochloride and an amount of naloxone or a pharmaceutically acceptable salt thereof equivalent to an amount of more than 2.5 mg of naloxone hydrochloride, the Ph. Eur. paddle test is performed in 900 ml of 0.1 N hydrochloric acid.

The term "titration" and its grammatical variations as mentioned hereinafter refers to the process by which a medical practitioner identifies a suitable dosage for a specific opioid such as oxycodone hydrochloride for a patient suffering from pain and in particular from chronic moderate to strong and even severe pain. As patients suffering from pain have different requirements with respect to the amount of opioid analgesics to be dosed due to their different metabolic properties, typically a physician first tries escalating doses of an immediate release formulation of an opioid formulation to identify the dosage amount of the opioid which will be sufficient for the patient to be pain-free or to have at least a significant reduction of pain intensity to provide acceptable pain control.

When a dosage amount being suitable to permanently control the (chronic) pain experienced by these patients is identified, the patient is typically changed to a controlled release formulation with a corresponding dosage amount so that the medication can be taken on a by-the-clock regimen at a reduced frequency, e.g. every 12 hours or only once a day. Such patients, who without pain treatment would suffer from chronic pain sensation, are typically designated as patients with controlled background pain.

In the context of the present invention the term "breakthrough pain" and its grammatical variations refer to a transitory increase in pain above the baseline or background pain experienced by patients being treated on a by-the-clock regimen of opioids.

The term "baseline pain" as used hereinafter is typically the pain that is reported by a patient as the average pain intensity experience for e.g. 12 or more hours with the patient being on an opioid regimen for treating pain.

Pain intensities of baseline pain will typically be determined using common methods such as a numerical analogue scale test (NAS). Determination of breakthrough pain attacks and baseline pain has been described in e.g. Portenoy et al. (1999) (*The Journal of Pain* 7(8):583-591) and Portenoy et al. (1999) (*Pain* 81:129-134). The definitions of breakthrough pain and controlled baseline pain as given in these publications are incorporated by reference herein. Thus, the designation of controlled baseline pain will typically require that two criteria are met.

First the patient will have to answer the question "Does your pain currently have a component that you would describe as "constant" or "almost constant" or "would be constant or almost constant" if not for the treatment being received?" in the affirmative. Second, the patient must be required to be treated by an opioid regimen that is consistent with relatively good pain control. The person skilled in the art will know how to determine controlled baseline pain on the basis of the information provided in the two references.

Breakthrough pain will then be identified as a flare of pain which is experienced by the patient above the level of a controlled baseline pain. Pain intensity may be assessed using e.g. a 5-point categorical scale with the items "none", "slight", "moderate", "severe" and "excruciating". A patient will typically experience a breakthrough pain attack if this attack has been rated by the patient as either severe or excruciating.

The term "bioequivalence" and its grammatical variations as mentioned hereinafter are used in their common sense. In particular, a pharmaceutical composition is said to be bioequivalent to a reference pharmaceutical composition if the 90% confidence interval of the mean value for the area under the curve (AUC) (AUCt or AUCinf) of the blood plasma levels of the pharmaceutical test composition is within 80% to 125% of the corresponding mean value of the reference pharmaceutical composition and if the 90% confidence interval of the mean value for the maximum concentration ($C_{max}$) of the blood plasma levels of the pharmaceutical test composition is within 80% to 125% of the corresponding mean value of the reference pharmaceutical composition.

The $C_{max}$ value indicates the maximum blood plasma concentration of the active agents, i.e. oxycodone and/or naloxone (or of their salts such as the hydrochloride salt).

The $t_{max}$ value indicates the time point at which the $C_{max}$ value is reached. In other words, $t_{max}$ is the time point of the maximum observed plasma concentration.

The AUC (Area Under the Curve) value corresponds to the area of the concentration curve. The AUC value is proportional to the amount of active agents, i.e. oxycodone and naloxone (or of their salts such as the hydrochloride salt) absorbed into the blood circulation in total and is hence a measure of the bioavailability.

The AUCt value is the value for the area under the plasma concentration-time curve from the time of administration to the last measurable concentration. AUCt values are usually calculated using the trapezoidal method. Where possible, LambdaZ, which is the terminal phase rate constant, is estimated using those points determined to be in the terminal lock-linear phase. t1/2Z, which is the apparent terminal phase half-life, is commonly determined from the ratio of ln 2 to LambdaZ. The areas under the plasma concentration-time curve between the last measured point and infinity may be calculated from the ratio of the final observed plasma concentration ($C_{last}$) to LambdaZ. This is then added to the AUCt to yield AUCinf, which is the area under the plasma concentration-time curve from the time of administration to infinity.

The term "bioavailability" is defined for purposes of the present invention as the extent to which active agents such as oxycodone and naloxone (or their salts such as the hydrochloride salt) are absorbed after oral administration of the pharmaceutical composition.

The term "steady state" can be described as follows: At the time t=0, the time the first dose is administered, the concentration C=0. The concentration then passes through a first maximum and then drops to a first minimum. Before the concentration drops to 0, another dose is administered, so that the second increase in concentration doesn't start at 0.

Building on this first concentration minimum, the curve passes through a second maximum after the second dose has been administered, which is above the first maximum, and drops to a second minimum, which is above the first minimum. Thus, the blood plasma curve escalates due to the repeated doses and the associated step-by-step accumulation of active agent, until it levels off to a point where absorption and elimination are in balance. The state, at which absorption and elimination are in equilibrium and the concentration oscillates constantly between a defined minimum and a defined maximum, is called steady state.

The terms "maintenance therapy" and "chronic therapy" are defined for purposes of the present invention as the drug therapy administered to a patient after a patient is titrated with an opioid analgesic to a steady state as define above. Baseline pain as mentioned above refers to the pain sensation during maintenance/chronic therapy.

Parameters describing the blood plasma curve can be obtained in clinical trials, first by once-off administration of the active agent such as oxycodone and naloxone (or of their salts such as the hydrochloride salt) to a number of test persons. The blood plasma values of the individual test persons are then averaged, e.g. a mean AUC, $C_{max}$ and $t_{max}$ value is obtained.

In the context of the present invention, pharmacokinetic parameters such as AUC, $C_{max}$ and $t_{max}$ refer to mean values unless indicated otherwise. Further, in the context of the present invention, in vivo parameters such as values for AUC, $C_{max}$, $t_{max}$, or analgesic efficacy refer to parameters or values obtained after administration at steady state or of a single dose to human patients and/or healthy human subjects.

If pharmacokinetic parameters such as mean $t_{max}$, $c_{max}$ and AUC are measured for healthy human subjects, they are typically obtained by measuring the development of blood plasma values over time in a test population of approximately 16 to 24 healthy human subjects.

Regulatory bodies such as the European Agency for the Evaluation of Medicinal Products (EMEA) or the Food and Drug Administration (FDA) will usually accept data obtained from e.g. 20 or 24 test persons. However, initial trials involving fewer participants such as 5 test persons may also be acceptable.

The term "healthy" human subject in this context refers to a typical male or female of usually Caucasian origin with average values as regards height, weight and physiological parameters such as blood pressure etc. Healthy human subjects for the purposes of the present invention are selected according to inclusion and exclusion criteria which are based on and in accordance with recommendations of the International Conference for Harmonization of Clinical Trials (ICH). For the purposes of the present invention, healthy subjects may be identified according to the inclusion and exclusion criteria as laid out in e.g. Example 2 and Example 3.

Thus, inclusion criteria comprise e.g. an age between ≥18 and ≤60 years; e.g. a BMI within the range 19-29 kg/m², and e.g. within the weight range 60-100 kg for males and 55-90 kg for females; that females must be non-nursing, non-pregnant, and provide a negative urine β-hCG pregnancy test within 24 hours before receiving the study medication; generally good health, evidenced by a lack of significantly abnormal findings on medical history, physical examination, clinical laboratory tests, vital signs, and ECG etc.

Exclusion criteria comprise e.g. exposure to any investigational drug or placebo within 3 months of the first dose of study medication, any significant illness within the 30 days before the first dose of study medication, any clinically significant abnormalities identified at prestudy screening for medical history, physical examination or laboratory analyses, use of any prescription medication (except HRT for postmenopausal females and contraceptive medication) in the 21 days, or over the counter medication including acid controllers, vitamins, herbal products and/or mineral supplements in the 7 days, before first dose of study medication, concurrent medical condition known to interfere with gastrointestinal drug absorption (e.g. delayed gastric emptying, mal absorption syndromes), distribution (e.g. obesity), metabolism or excretion (e.g. hepatitis, glomerulonephritis), history of or concurrent medical condition, which in the opinion of the investigator would compromise the ability of the subject to safely complete the study, history of seizure disorders for which subjects required pharmacologic treatment, current history of smoking more than 5 cigarettes a day, subjects with evidence of active or past history of substance or alcohol abuse according to DSM-IV criteria, subjects who reported regular consumption of 2 or more alcoholic drinks per day or have blood alcohol levels of ≥0.5% at screening, donation of more than 500 mL of blood or blood products or other major blood loss in the 3 months before first dose of study medication, any positive results in the prestudy screen for ethanol, opiates, barbiturates, amphetamines, cocaine metabolites, methadone, propoxyphene, phencyclidine, benzodiazepines, and cannabinoids in the specimen of urine collected at screening, known sensitivity to oxycodone, naloxone, or related compounds etc.

If pharmacokinetic parameters such as mean $t_{max}$, $c_{max}$ and AUC are obtained in patients, the patient group will comprise typically between 10 to 200 patients. A reasonable number of patients will e.g. be 10, 20, 30, 40, 50, 75, 100, 125 or 150 patients. Patients will be selected according to symptoms of the condition to be treated. Patients may be e.g. ≥18 years, suffer from moderate to strong and even severe chronic pain of tumor and non-tumor origin, will show insufficient efficacy and/or tolerability with a WHO step II or III analgesic etc. A patient may e.g. not be considered for determination of pharmacokinetic parameters if there are indications of current alcohol or drug abuse, of current severe cardiovascular and respiratory diseases, of severe liver and renal insufficiency etc.

It is to be understood that values of pharmacokinetic parameters as indicated above and below have been deduced on the basis of the data which were obtained in Examples 2 and 3, all of which relate to single dose studies in healthy human subjects. However, it is assumed that comparable results will be obtained upon steady state administration in healthy human subjects or single dose and steady state administration in human patients. The skilled person, of course, knows that Cmax of steady state will be higher than Cmax after single dose administration.

Pharmacokinetic parameter calculations may be performed with WinNonlin Enterprise Edition, Version 4.1.

As mentioned above, the present invention relates to an oral immediate release pharmaceutical composition comprising at least oxycodone or a pharmaceutically acceptable salt thereof and naloxone or a pharmaceutically acceptable salt thereof in about a 2:1 ratio (oxycodone or a pharmaceutically acceptable salt thereof: naloxone or a pharmaceutically acceptable salt thereof) by weight.

Further, as becomes clear from Experiment 2, oral immediate release pharmaceutical compositions of the invention are dose-proportional, particularly when they comprise an amount of oxycodone or a pharmaceutically acceptable salt thereof equivalent to about 2.5 mg to about 20 mg of oxycodone hydrochloride and an amount of naloxone or a pharmaceutically acceptable salt thereof equivalent to about 1.25 mg to about 10 mg of naloxone hydrochloride in a ratio of about 2:1 by weight.

The oral immediate release pharmaceutical compositions of the invention are particularly suitable for titration of patients suffering from pain and/or for treating breakthrough pain in patients suffering from pain.

In particular, the oral immediate release formulations of the present invention may be used for titrating a patient suffering from pain and in particular from strong to severe (chronic) pain for which titration with controlled release formulations of oxycodone and naloxone in the past would have meant an unpleasant if not unacceptable experience of pain due to the delayed action of controlled release preparations.

Furthermore, oral immediate release formulations in accordance with the present invention can be used to treat e.g. breakthrough pain attacks in patients, who are already treated with controlled release formulations of oxycodone or a pharmaceutically acceptable salt thereof and naloxone or a pharmaceutically acceptable salt thereof but nevertheless have experienced sudden pain attacks and therefore have required an immediate release formulation comprising only the opioid oxycodone hydrochloride.

As mentioned, the pharmaceutical dosage forms of the present invention also relate to an oral immediate release pharmaceutical composition comprising at least oxycodone or a pharmaceutically acceptable salt thereof and naloxone or a pharmaceutically acceptable salt thereof, wherein the composition is provided in the form of a tablet and wherein the composition provides a fast in vitro dissolution profile such that e.g. more than 90% or even more than 95% of the actives are released after 15 min. These combined properties have the advantage that the composition may be administered in solid form, e.g. as tablet which can be swallowed. At the same time, patient groups such as children or elderly persons who may have problems with swallowing, may administer the tablet by firstly dissolving it rapidly in liquid prior to administration or it may be placed directly in the mouth for fast dissolve in the saliva. This can be of important convenience if pain attacks suddenly occur so that quick pain relief is required.

As already mentioned, the present invention essentially relates to an oral immediate release pharmaceutical composition comprising at least oxycodone or a pharmaceutically acceptable salt thereof and naloxone or a pharmaceutically acceptable salt thereof, preferably in about a 2:1 ratio (oxycodone or a pharmaceutically acceptable salt thereof: naloxone or a pharmaceutically acceptable salt thereof) by weight.

In principle, the oral immediate release pharmaceutical compositions may comprise pharmaceutically active agents in addition to oxycodone and naloxone. However, in a preferred embodiment of all aspects of the invention, oral immediate release pharmaceutical compositions in accordance with the invention comprise oxycodone or a pharmaceutically acceptable salt thereof and naloxone or a pharmaceutically acceptable salt thereof as the sole pharmaceutically active agents.

Oxycodone and naloxone may be present in the oral immediate release pharmaceutical dosage forms of the present invention as free base.

However, oxycodone or naloxone may also be present in the form of their pharmaceutically acceptable salts. Such salts include e.g. the hydrochloride salt, the sulphate salt, the bisulphate salt, the tartrate salt, the nitrate salt, the citrate salt, the bitartrate salt, the phosphate salt, the malate salt, the maleate salt, the hydrobromide salt, the hydroiodide salt, the fumarate salt, the succinate salt and the like.

Oxycodone and naloxone as mentioned hereinafter may also be present as base addition salts such as metal salts of alkali metals including lithium, sodium and potassium. They may also be present in the form of derivatives of the free base. Such derivatives include e.g. esters.

In a preferred embodiment, the present invention uses oxycodone hydrochloride and naloxone hydrochloride. In a further preferred embodiment of the present invention, oral immediate release pharmaceutical compositions comprise oxycodone hydrochloride and naloxone hydrochloride, preferably in about a 2:1 ratio by weight as the sole pharmaceutically active agents.

The oral immediate release pharmaceutical compositions of the present invention will comprise oxycodone in an amount that will be sufficient to treat pain and in particular strong to severe (chronic) pain in patients. Typically, a pharmaceutical composition of the invention will comprise an amount of oxycodone or a pharmaceutically acceptable salt thereof equivalent to about 1 mg to about 160 mg of oxycodone hydrochloride.

The amount of naloxone in the pharmaceutical compositions of the present invention will be chosen such that the amount of naloxone administered does not substantially negatively influence the pain relief mediated by oxycodone. Typically, a pharmaceutical composition of the present invention will comprise an amount of naloxone or a pharmaceutically acceptable salt thereof equivalent to about 0.5 mg to about 80 mg of naloxone hydrochloride.

It is to be understood that the amount of oxycodone or a pharmaceutically acceptable salt thereof and of naloxone or a pharmaceutically acceptable salt thereof can be chosen such that the ratio of oxycodone or a pharmaceutically acceptable salt thereof: naloxone or a pharmaceutically acceptable salt thereof is about 2:1 by weight based on the weight of oxycodone or a pharmaceutically acceptable salt thereof and naloxone or a pharmaceutically acceptable salt thereof.

Thus, pharmaceutical compositions of the present invention will typically comprise an amount of oxycodone or a pharmaceutically acceptable salt thereof equivalent to about 1 mg to about 160 mg of oxycodone hydrochloride, equivalent to about 1 mg to about 80 mg of oxycodone hydrochloride, equivalent to about 1 mg to about 40 mg of oxycodone hydrochloride, equivalent to about 1 mg to about 20 mg of oxycodone hydrochloride, equivalent to about 1 mg to about 10 mg of oxycodone hydrochloride, equivalent to about 1 mg to about 5 mg of oxycodone hydrochloride and equivalent to about 1 mg to about 2.5 mg of oxycodone hydrochloride.

Further, pharmaceutical compositions of the present invention will typically comprise an amount of naloxone or a pharmaceutically acceptable salt thereof equivalent to about 0.5 mg to about 80 mg of naloxone, equivalent to about 0.5 mg to about 40 mg of naloxone hydrochloride, equivalent to about 0.5 mg to about 20 mg of naloxone hydrochloride, equivalent to about 0.5 mg to about 10 mg of naloxone hydrochloride, equivalent to about 0.5 mg to about 5 mg of naloxone hydrochloride, equivalent to about 0.5 mg to about 2.5 mg of naloxone hydrochloride, and equivalent to about 0.5 mg to about 1.25 mg of naloxone hydrochloride.

Preferred embodiments of the present invention relate to pharmaceutical compositions which comprise an amount of oxycodone or a pharmaceutically acceptable salt thereof equivalent to about 2.5 mg to about 40 mg of oxycodone hydrochloride, preferably to about 2.5 mg to about 20 mg of oxycodone hydrochloride, and an amount of naloxone or a pharmaceutically acceptable salt thereof equivalent to about 1.25 mg to about 20 mg of naloxone hydrochloride, preferably to about 1.25 mg to about 10 mg of naloxone hydrochloride. These compositions may in particular use the hydrochloride salts of oxycodone and naloxone.

Particularly preferred dosage strengths of oral immediate release pharmaceutical compositions in accordance with the invention comprise an amount of oxycodone or a pharmaceutically acceptable salt thereof equivalent to about 2.5 mg and an amount of naloxone or a pharmaceutically acceptable salt thereof equivalent to about 1.25 mg, an amount of oxycodone or a pharmaceutically acceptable salt thereof equivalent to about 5 mg of oxycodone hydrochloride and an amount of naloxone or a pharmaceutically acceptable salt thereof equivalent to about 2.5 mg of naloxone hydrochloride, an amount of oxycodone or a pharmaceutically acceptable salt thereof equivalent to about 10 mg of oxycodone hydrochloride and an amount of naloxone or a pharmaceutically acceptable salt thereof equivalent to about 5 mg of naloxone hydrochloride, and an amount of oxycodone or a pharmaceutically acceptable salt thereof equivalent to about 20 mg of oxycodone hydrochloride and an amount of naloxone or a pharmaceutically acceptable salt thereof equivalent to about 10 mg of naloxone hydrochloride. These compositions may in particular use the hydrochloride salts of oxycodone and naloxone.

Particularly preferred embodiments of the present invention relate to oral immediate release pharmaceutical compositions comprising 2.5 mg of oxycodone hydrochloride and 1.25 mg of naloxone hydrochloride, 5 mg of oxycodone hydrochloride and 2.5 mg of naloxone hydrochloride, 10 mg of oxycodone hydrochloride and 5 mg of naloxone hydrochloride, and 20 mg of oxycodone hydrochloride and 10 mg of naloxone hydrochloride.

Oral immediate release pharmaceutical compositions in accordance with the invention which comprise oxycodone or a pharmaceutically acceptable salt thereof and naloxone or a pharmaceutically acceptable salt thereof in about a 2:1 ratio by weight, typically release in vitro, when measured using the Ph. Eur. Paddle Method at 100 rpm in 0.1 N hydrochloric acid at 37° C. and using UV detection at 230 nm, ≥75% of oxycodone or a pharmaceutically acceptable salt thereof by weight and ≥75% of naloxone or a pharmaceutically acceptable salt thereof by weight at 45 min. More preferably, pharmaceutical compositions in accordance with the invention release in vitro, when measured using the Ph. Eur. Paddle Method at 100 rpm in 0.1 N hydrochloric acid at 37° C. and using UV detection at 230 nm, ≥80% of oxycodone or a pharmaceutically acceptable salt thereof by weight and ≥80% of naloxone or a pharmaceutically acceptable salt thereof by weight at 45 min.

Even more preferably, pharmaceutical compositions in accordance with the present invention which comprise oxycodone or a pharmaceutically acceptable salt thereof and naloxone or a pharmaceutically acceptable salt thereof in about a 2:1 ratio by weight, release in vitro, when measured using the Ph. Eur. Paddle Method at 100 rpm in 0.1 N hydrochloric acid at 37° C. and using UV detection at 230 nm, 80%, and preferably ≥90%, and even more preferably ≥95%, of oxycodone or a pharmaceutically acceptable salt thereof and ≥80%, preferably ≥90%, and even more preferably ≥95%, of naloxone or a pharmaceutically acceptable salt thereof at 15 min.

Oral immediate release pharmaceutical compositions in accordance with the present invention may be provided in a dosage form common for immediate release formulations. Thus, oral immediate release pharmaceutical compositions according to the present invention may be in solid form such as a tablet, a capsule, multiparticulates, e.g. granules, spheroids or beads, or liquids, e.g. a solution, suspension, or emulsion. A preferred dosage form for oral immediate release pharmaceutical compositions of the present invention is a tablet.

When producing oral immediate release pharmaceutical compositions in accordance with the present invention one may use, in addition to oxycodone or a pharmaceutically acceptable salt thereof and naloxone or a pharmaceutically acceptable salt thereof, pharmaceutically acceptable excipients as they are common in the pharmaceutical arts. Typical pharmaceutically acceptable excipients are disintegrants, diluents, lubricants, glidants, anti-tacking agents, plasticizers, colourants, flavorants, binders, pH adjusters and the like. These excipients (with the exception of disintegrants) are to be chosen such that they do not substantially alter the immediate release in vitro release rates as described above.

It can be preferred for the pharmaceutical compositions of the present invention to comprise at least a diluent and optionally a disintegrant as pharmaceutically acceptable excipients, particularly if the pharmaceutical compositions of the present invention are provided as a tablet. It can also be preferred for the pharmaceutical compositions of the present invention to comprise at least a disintegrant and optionally a diluent as pharmaceutically acceptable excipients, particularly if the pharmaceutical compositions of the present invention are provided as a tablet. It can further be preferred to use excipients which act both as a disintegrant and a diluent.

The disintegrant, for example, will ensure that the tablet after administration will rapidly disintegrate so that the active ingredients oxycodone or a pharmaceutically acceptable salt thereof and naloxone or a pharmaceutically acceptable salt thereof become readily available for absorption.

Diluents may be selected from but are not limited to lactose such as lactose monohydrate, lactose anhydrous, starch such as maize starch, pregelatinized starch, microcrystalline cellulose, glucose, Mannitol, Maltitol, StarLac® (85% spray dried lactose, 15% maize starch), saccharose, calcium salts like calcium hydrogen phosphate or any combinations of the above.

Disintegrants may be selected from but are not limited to inter alia StarLac® (85% spray dried lactose, 15% maize starch), croscarmellose such as croscarmellose sodium, sodium starch glycolate, crospovidone, alginic acid, or low substituted hydroxypropyl cellulose.

A combination of lactose and starch such as the Starlac® product can be particularly preferred as it combines the properties of a filler and a disintegrant.

Glidants and lubricants may be selected but are not limited to inter alia highly dispersed silica, talcum, magnesium oxide, magnesium stearate, sodium stearyl fumarate etc.

Flowing agents and lubricants comprise inter alia highly dispersed silica, talcum, magnesium oxide, magnesium stearate, sodium stearyl fumarate etc.

If pharmaceutical compositions of the present invention are provided as a tablet, they may be coated for identification purposes with a cosmetic coating. Such coatings will have no substantial impact on the immediate release properties of the pharmaceutical compositions in accordance with the invention.

In a preferred embodiment, the present invention relates to oral immediate release pharmaceutical compositions comprising about 2.5 to about 160 mg of oxycodone hydrochloride and about 1.25 mg to about 80 mg of naloxone hydrochloride in about a 2:1 ratio (oxycodone hydrochloride: naloxone hydrochloride) by weight, wherein the formulation releases in vitro, when measured using the Ph. Eur. Paddle Method at 100 rpm in 0.1 N hydrochloric acid at 37° C. and using UV detection at 230 nm, ≥90% and preferably ≥95% of oxycodone hydrochloride by weight and ≥90% and preferably ≥95% of naloxone hydrochloride by weight at 15 min. Preferably such compositions comprise a disintegrant and take a solid form such as a tablet.

In another preferred embodiment, the present invention relates to oral immediate release pharmaceutical compositions comprising about 2.5 to about 80 mg of oxycodone hydrochloride and about 1.25 mg to about 40 mg of naloxone hydrochloride in about a 2:1 ratio (oxycodone hydrochloride: naloxone hydrochloride) by weight, wherein the formulation releases in vitro, when measured using the Ph. Eur. Paddle Method at 100 rpm in 0.1 N hydrochloric acid at 37° C. and using UV detection at 230 nm, ≥90% and preferably ≥95% of oxycodone hydrochloride by weight and ≥90% and preferably ≥95% of naloxone hydrochloride by weight at 15 min.

Preferably such compositions comprise a disintegrant and take a solid form such as a tablet.

In another preferred embodiment, the present invention relates to oral immediate release pharmaceutical compositions comprising about 2.5 to about 40 mg of oxycodone hydrochloride and about 1.25 mg to about 20 mg of naloxone hydrochloride in about a 2:1 ratio (oxycodone hydrochloride: naloxone hydrochloride) by weight, wherein the formulation releases in vitro, when measured using the Ph. Eur. Paddle Method at 100 rpm in 0.1 N hydrochloric acid at 37° C. and using UV detection at 230 nm, ≥90% and preferably ≥95% of oxycodone hydrochloride by weight and ≥90% and preferably ≥95% of naloxone hydrochloride by weight at 15 min. Preferably such compositions comprise a disintegrant and take a solid form such as a tablet.

In another preferred embodiment, the present invention relates to oral immediate release pharmaceutical compositions comprising about 2.5 to about 20 mg of oxycodone hydrochloride and about 1.25 mg to about 10 mg of naloxone hydrochloride in about a 2:1 ratio (oxycodone hydrochloride: naloxone hydrochloride) by weight, wherein the formulation releases in vitro, when measured using the Ph. Eur. Paddle Method at 100 rpm in 0.1 N hydrochloric acid at 37° C. and using UV detection at 230 nm, ≥90% and preferably ≥95% of oxycodone hydrochloride by weight and ≥90% and preferably ≥95% of naloxone hydrochloride by weight at 15 min. Preferably such compositions comprise a disintegrant and take a solid form such as a tablet.

In yet another preferred embodiment, the present invention relates to oral immediate release pharmaceutical compositions comprising about 2.5 to about 10 mg of oxycodone hydrochloride and about 1.25 mg to about 5 mg of naloxone hydrochloride in about a 2:1 ratio (oxycodone hydrochloride: naloxone hydrochloride) by weight, wherein the formulation releases in vitro, when measured using the Ph. Eur. Paddle Method at 100 rpm in 0.1 N hydrochloric acid at 37° C. and using UV detection at 230 nm, ≥90% and preferably ≥95% of oxycodone hydrochloride by weight and ≥90% and preferably ≥95% of naloxone hydrochloride by weight at 15 min. Preferably such compositions comprise a disintegrant and take a solid form such as a tablet.

Of the oral immediate release pharmaceutical compositions of the invention which comprise an amount of oxycodone or a pharmaceutically acceptable salt thereof equivalent to about 2.5 mg to about 20 mg of oxycodone hydrochloride and an amount of naloxone or a pharmaceutically acceptable salt thereof equivalent to about 1.25 mg to about 10 mg of naloxone hydrochloride in a ratio of about 2:1 by weight, those can be preferred which provide for an AUCt of oxycodone in the range of about 15 ng·h/mL to about 500 ng·h/mL, preferably in the range of about 20 ng·h/mL to about 400 ng·h/mL, more preferably in the range of about 25 ng·h/mL to about 300 ng·h/mL, and even more preferably in the range of about 30 ng·h/mL to about 250 ng·h/mL, when administered in a single dose study in healthy human volunteers. Such oral immediate release pharmaceutical compositions may preferably comprise the hydrochloride salts of oxycodone and naloxone.

Of the oral immediate release pharmaceutical compositions of the invention which comprise an amount of oxycodone or a pharmaceutically acceptable salt thereof equivalent to about 2.5 mg to about 20 mg of oxycodone hydrochloride and an amount of naloxone or a pharmaceutically acceptable salt thereof equivalent to about 1.25 mg to about 10 mg of naloxone hydrochloride in a ratio of about 2:1 by weight, those can be preferred which provide for a Cmax of oxycodone in the range of about 1 ng/mL to about 300 ng/mL, preferably in the range of about 2 ng/mL to about 200 ng/mL, more preferably in the range of about 3 ng/mL to about 100 ng/mL, even more preferably in the range of about 4 ng/mL to about 75 ng/mL and most preferably in the range of about 6 ng/mL to about 50 ng/mL when administered in a single dose study in healthy human volunteers. Such oral immediate release pharmaceutical compositions may preferably comprise the hydrochloride salts of oxycodone and naloxone.

Embodiments of the present invention also relate to oral immediate release pharmaceutical compositions which comprise oxycodone or a pharmaceutically acceptable salt thereof and naloxone or a pharmaceutically acceptable salt thereof and wherein the pharmaceutical composition after storage under stressed conditions releases the pharmaceutically active agents with substantially the same release rate as before subjecting the pharmaceutical composition to stressed conditions.

Other embodiments of the present invention relate oral immediate release pharmaceutical compositions which comprise oxycodone or a pharmaceutically acceptable salt thereof and naloxone or a pharmaceutically acceptable salt thereof and wherein the pharmaceutical composition after storage under stressed conditions has less than 3.0% of total substances related to oxycodone or a pharmaceutically acceptable salt thereof and/or related to naloxone or a pharmaceutically acceptable salt or thereof.

Storage under stressed conditions in the context of the present invention means that a pharmaceutical composition is subjected to increased temperature and/or relative humidity (RH) for prolonged periods of time. For example, typical stressed conditions refer to storage over at least one, two, three, four, five, six, nine or twelve months at 25° C. and 60% RH. Other stressed conditions refer to storage over at least one, two, three, four or five months at 40° C. and 75% RH.

Such stressed storage conditions are used to determine whether a pharmaceutical composition has a shelf life sufficient for long time storage under conditions as they are common in patients' households without negative effects on its safety and efficacy. Such negative effects may include that the in-vitro release rates change over time so that the efficacy of the composition is affected as different amounts of actives are released after administration. Similarly, negative effects may also result from degradation of the pharmaceutically active agents which may either decrease the overall amount of functional pharmaceutically active agent or lead to formation of toxic by-products.

If changes in the in vitro release profile or with respect to the amount of the active agent(s) of a pharmaceutical composition are observed after storage under stressed conditions, this may be indicative of stability problems. If such changes are not observed, this means vice versa that the pharmaceutical composition is storage stable.

The term "substantially the same release rate" refers to the situation where the in vitro release rate for a pharmaceutical composition which has been subjected to stressed conditions is compared to a reference composition. The reference composition is an identical pharmaceutical composition which, however, has not been subjected to stressed conditions. If the in vitro release profile of the composition subjected to stressed conditions does not deviate by more than about 20%, preferably by no more than about 15%, more preferably by no more than 10% and even more preferably by no more than about 5% from the in vitro release profile of the reference composition, the in-vitro release rate is considered to be substantially the same.

The term "total oxycodone and naloxone related substances" refers to substances that arise from chemical reactions of these pharmaceutically active agents. These include e.g. naloxone n-oxide and the like.

In order to assess stability one may subject a pharmaceutical composition to stressed conditions as mentioned above and determine the amount of oxycodone and/or naloxone related substances. One then determines the amount of oxycodone and/or naloxone related substances for an identical pharmaceutical composition which has not been subjected to stressed conditions. This composition is considered to be a reference composition. The detection of "oxycodone related substances" and "naloxone related substances" is typically performed by HPLC analysis. The identity of substances can be determined by doing the same analysis with pure known reference substances.

A pharmaceutical composition will be considered to be stable if after subjecting it to stressed conditions, it has no more than about 3%, preferably no more than about 2%, more preferably no more than about 1% and even more preferably no more than about 0.5% of oxycodone and/or naloxone related substances in comparison to the amount of hydromorphone or naloxone that is present within the composition.

It is to be understood that the properties of compositions having substantially the same release rate after storage under stressed conditions and/or having less than 3% of oxycodone and naloxone related substances after storage under stressed conditions pertain also to embodiments which have mentioned before, such as compositions having a 2:1 by weight ratio, compositions having the above mentioned amounts and/or compositions having the above mentioned in vitro release profiles, particularly if the compositions take a solid form such as tablet.

Pharmaceutical compositions in accordance with the invention which are provided in solid form, e.g. in the form of a tablet may be produced by a method comprising e.g. the following steps:

a) Blending oxycodone or a pharmaceutically acceptable salt thereof, naloxone or a pharmaceutically acceptable salt thereof both of a suitable particle size, a diluent and optionally a disintegrant;
b) Optionally lubricating said blend;
c) Directly compressing said blend to obtain a tablet.

Pharmaceutical compositions in accordance with the invention which are provided in solid form, e.g. in the form of a tablet may be produced by a method comprising e.g. the following steps:

a) Blending oxycodone or a pharmaceutically acceptable salt thereof, naloxone or a pharmaceutically acceptable salt thereof both of a suitable particle size, a disintegrant and optionally a diluent;
b) Optionally lubricating said blend;
c) Directly compressing said blend to obtain a tablet.

If deemed necessary, the above process may comprise screening steps at various occasions in order to ensure lump-free components for uniform blending.

Preferably, all excipients, and optionally the active ingredients also, are within the same size range. A typical size range would be about 100 µm to about 300 µm.

Tablets which are obtained by such a procedure have been found to rapidly disintegrate and to e.g. release in vitro ≥90% and preferably ≥95% of oxycodone or a pharmaceutically acceptable salt thereof and 90% and preferably ≥95% of naloxone or a pharmaceutically acceptable salt thereof at 15 min. when measured by the Ph. Eur. Paddle Method as outlined above. As can be taken from Example 4, tablets produced according to such a procedure are storage stable, meaning that they do not substantially change their in vitro release behaviour after prolonged storage under stressed conditions.

Immediate release pharmaceutical compositions as described above and as manufactured above may be used for titrating patients suffering from pain and in particular from moderate to severe (chronic) pain. Such formulations may also be used for treating breakthrough pain in patients suffering from pain and in particular from moderate to severe (chronic) pain.

Using oral immediate release pharmaceutical compositions for titration of patients and treating breakthrough pain in patients will ensure a quick pain relief in the patients as a consequence of the immediate release properties without their suffering from typical opioid induced side effects such as constipation and urinary retention.

The invention will be described below with respect to some specific examples. These examples are, however, not to be construed as limiting.

The invention can be illustrated by the following embodiments enumerated in the numbered paragraphs below:

1. An oral immediate release pharmaceutical composition comprising at least oxycodone or a pharmaceutically acceptable salt thereof and naloxone or a pharmaceutically acceptable salt thereof in about a 2:1 ratio (oxycodone or a pharmaceutically acceptable salt thereof: naloxone or a pharmaceutically acceptable salt thereof) by weight.

2. An oral immediate release pharmaceutical composition of paragraph 1,
   wherein the pharmaceutically acceptable salt of oxycodone and wherein the pharmaceutically acceptable salt of naloxone are selected from the hydrochloride salts of oxycodone and naloxone.

3. An oral immediate release pharmaceutical composition of paragraph 2,
   wherein the composition comprises oxycodone hydrochloride and naloxone hydrochloride as the sole pharmaceutically active agents.

4. An oral immediate release pharmaceutical composition of any of paragraphs 1, 2 or 3,
   wherein the formulation comprises an amount of oxycodone or a pharmaceutically acceptable salt thereof equivalent to about 1 mg to about 160 mg of oxycodone hydrochloride and an amount of naloxone or a pharmaceutically acceptable salt thereof equivalent to about 0.5 mg to about 80 mg of naloxone hydrochloride.

5. An oral immediate release pharmaceutical composition of paragraph 4,
   wherein the formulation comprises an amount of oxycodone or a pharmaceutically acceptable salt thereof equivalent to about 2.5 mg to about 40 mg of oxycodone hydrochloride and an amount of naloxone or a pharmaceutically acceptable salt thereof equivalent to about 1.25 mg to about 20 mg of naloxone hydrochloride.

6. An oral immediate release pharmaceutical composition of paragraph 5,
   wherein the formulation comprises an amount of oxycodone or a pharmaceutically acceptable salt thereof equivalent to about 2.5 mg to about 20 mg of oxycodone hydrochloride and an amount of naloxone or a pharmaceutically acceptable salt thereof equivalent to about 1.25 mg to about 10 mg of naloxone hydrochloride.

7. An oral immediate release pharmaceutical composition of paragraph 6, wherein the formulation comprises about 2.5 mg to about 20 mg of oxycodone hydrochloride and about 1.25 mg to about 10 mg of naloxone hydrochloride.

8. An oral immediate release pharmaceutical composition of claim 7,
wherein the composition comprises oxycodone hydrochloride and naloxone hydrochloride as the sole pharmaceutically active agents.

9. An oral immediate release pharmaceutical composition of any of paragraphs 1, 2, 3, 4, 5, 6, 7 or 8,
wherein the formulation releases in vitro, when measured using the Ph. Eur. Paddle Method at 100 rpm in 0.1 N hydrochloric acid at 37° C. and using UV detection at 230 nm, >75% of oxycodone or a pharmaceutically acceptable salt thereof by weight and >75% of naloxone or a pharmaceutically acceptable salt thereof by weight at 45 min.

10. An oral immediate release pharmaceutical composition of paragraph 9,
wherein the formulation releases in vitro, when measured using the Ph. Eur. Paddle Method at 100 rpm in 0.1 N hydrochloric acid at 37° C. and using UV detection at 230 nm, >80% of oxycodone or a pharmaceutically acceptable salt thereof by weight and >80% of naloxone or a pharmaceutically acceptable salt thereof by weight at 45 min.

11. An oral immediate release pharmaceutical composition of paragraphs 9 or 10,
wherein the formulation releases in vitro, when measured using the Ph. Eur. Paddle Method at 100 rpm in 0.1 N hydrochloric acid at 37° C. and using UV detection at 230 nm, >80% of oxycodone or a pharmaceutically acceptable salt thereof by weight and >80% of naloxone or a pharmaceutically acceptable salt thereof by weight at 15 min.

12. An oral immediate release pharmaceutical composition of paragraph 11,
wherein the formulation releases in vitro, when measured using the Ph. Eur. Paddle Method at 100 rpm in 0.1 N hydrochloric acid at 37° C. and using UV detection at 230 nm, >90% of oxycodone or a pharmaceutically acceptable salt thereof by weight and >90% of naloxone or a pharmaceutically acceptable salt thereof by weight at 15 min.

13. An oral immediate release pharmaceutical composition of paragraph 12,
wherein the formulation releases in vitro, when measured using the Ph. Eur. Paddle Method at 100 rpm in 0.1 N hydrochloric acid at 37° C. and using UV detection at 230 nm, >95% of oxycodone or a pharmaceutically acceptable salt thereof by weight and >95% of naloxone or a pharmaceutically acceptable salt thereof by weight at 15 min.

14. An oral immediate release pharmaceutical composition of any of paragraphs 1, 2, 3, 4, 5, 6, 7, 8, 9, 10, 11, 12 or 13,
wherein the composition is in the form of a tablet, of a capsule, of multiparticulates, of pellets, or of a liquid.

15. An oral immediate release pharmaceutical composition of any of paragraphs 1, 2, 3, 4, 5, 6, 7, 8, 9, 10, 11, 12, 13 or 14,
wherein the formulation comprises at least a diluents and optionally a disintegrant as pharmaceutically acceptable excipients.

16. An oral immediate release pharmaceutical composition of any of paragraphs 1, 2, 3, 4, 5, 6, 7, 8, 9, 10, 11, 13 or 14,
wherein the formulation comprises at least a disintegrant and optionally a diluents as pharmaceutically acceptable excipients.

17. An oral immediate release pharmaceutical composition of any of paragraphs 1, 2, 3, 4, 5, 6, 7, 8, 9, 10, 11, 12, 13, 14, 15 or 16,
wherein the formulation comprises about 2.5 mg to about 20 mg of oxycodone hydrochloride and about 1.25 mg to about 10 mg of naloxone hydrochloride in about a 2:1 ratio (oxycodone hydrochloride:naloxone hydrochloride) by weight, wherein the composition comprises oxycodone hydrochloride and naloxone hydrochloride as the sole pharmaceutically active agents, wherein the composition is in solid form, optionally in the from of a tablet, wherein the formulation comprises at least a disintegrant and optionally a diluent as pharmaceutically acceptable excipients and wherein the formulation releases in vitro, when measured using the Ph. Eur. Paddle Method at 100 rpm in 0.1 N hydrochloric acid at 37° C. and using UV detection at 230 nm, >80% of oxycodone hydrochloride by weight and >80% of naloxone hydrochloride by weight at 45 min.

18. An oral immediate release pharmaceutical composition of paragraph 17,
wherein the formulation releases in vitro, when measured using the Ph. Eur. Paddle Method at 100 rpm in 0.1 N hydrochloric acid at 37° C. and using UV detection at 230 nm, >95% of oxycodone hydrochloride by weight and >95% of naloxone hydrochloride by weight at 15 min.

19. An oral immediate release pharmaceutical composition comprising oxycodone or a pharmaceutically acceptable salt thereof and naloxone or a pharmaceutically acceptable salt thereof, wherein the formulation releases in vitro, when measured using the Ph. Eur. Paddle Method at 100 rpm in 0.1 N hydrochloric acid at 37° C. and using UV detection at 230 nm, >90% of oxycodone or a pharmaceutically acceptable salt thereof by weight and >90% of naloxone or a pharmaceutically acceptable salt thereof by weight at 15 min.

20. An oral immediate release pharmaceutical composition according to paragraph 19, wherein the formulation releases in vitro, when measured using the Ph. Eur. Paddle Method at 100 rpm in 0.1 N hydrochloric acid at 37° C. and using UV detection at 230 nm, >95% of oxycodone or a pharmaceutically acceptable salt thereof by weight and >95% of naloxone or a pharmaceutically acceptable salt thereof by weight at 15 min.

21. An oral immediate release pharmaceutical composition according to paragraphs 19 or 20, wherein the pharmaceutical composition comprises an amounts of oxycodone or a pharmaceutically acceptable salt thereof equivalent to about 1 mg to 160 mg of oxycodone hydrochloride and an amount of naloxone or a pharmaceutically acceptable salt thereof equivalent to about 0.5 mg to about 80 mg of naloxone hydrochloride.

22. An oral immediate release pharmaceutical composition according to paragraphs 19, 20 or 21, wherein the pharmaceutical composition comprises oxycodone or a pharmaceutically acceptable salt thereof and naloxone or a pharmaceutically acceptable salt thereof in about a 2:1 ratio (oxycodone or a pharmaceutically acceptable salt thereof, naloxone or a pharmaceutically acceptable salt thereof) by weight.

23. An oral immediate release pharmaceutical composition according to paragraphs 19, 20, 21 or 22, wherein the pharmaceutical composition is in solid form.

24. An oral immediate release pharmaceutical composition according to claim 19, 20, 21, 22 or 23, wherein the pharmaceutical composition additionally comprises at least a disintegrant.

25. An oral immediate release pharmaceutical composition according to paragraphs 19, 20, 21, 22, 23 or 24, wherein the pharmaceutical composition comprises oxycodone hydrochloride and naloxone hydrochloride as the sole pharmaceutically active agents.

26. An oral immediate release pharmaceutical composition of any of paragraphs 1, 2, 3, 4, 5, 6, 7, 8, 9, 10, 11, 12, 13, 14, 15, 16, 17, 18, 19, 20, 21, 22, 23, 24, 25 or 26 for use in titrating patients suffering from pain.

27. An oral immediate release pharmaceutical composition of any of paragraphs 1, 2, 3, 4, 5, 6, 7, 8, 9, 10, 11, 12, 13, 14, 15, 16, 17, 18, 19, 20, 21, 22, 23, 24, 25 or 26 for treating breakthrough pain in patients suffering from pain.

28. Use of an oral immediate release pharmaceutical composition of any of paragraphs 1 2, 3, 4, 5, 6, 7, 8, 9, 10, 11, 12, 13, 14, 15, 16, 17, 18, 19, 20, 21, 22, 23, 24, 25 or 26 in the manufacture of a medicament for titrating patients suffering from pain.

29. Use of an oral immediate release pharmaceutical composition of any of paragraphs 1, 2, 3, 4, 5, 6, 7, 8, 9, 10, 11, 12, 13, 14, 15, 16, 17, 18, 19, 20, 21, 22, 23, 24, 25 or 26 in the manufacture of a medicament treating breakthrough pain in patients suffering from pain.

30. Method of titrating a patient suffering from pain by administering an oral immediate release pharmaceutical composition of any of paragraphs 1, 2, 3, 4, 5, 6, 7, 8, 9, 10, 11, 12, 13, 14, 15, 16, 17, 18, 19, 20, 21, 22, 23, 24, 25 or 26.

31. Method of treating breakthrough pain in a patient suffering from pain by administering an oral immediate release pharmaceutical composition of any of paragraphs 1, 2, 3, 4, 5, 6, 7, 8, 9, 10, 11, 12, 13, 14, 15, 16, 17, 18, 19, 20, 21, 22, 23, 24, 25 or 26.

EXAMPLES

Example 1

Preparation of Immediate Release Pharmaceutical Compositions Comprising Oxycodone Hydrochloride and Naloxone Hydrochloride Immediate release pharmaceutical compositions comprising 20 mg oxycodone hydrochloride/10 mg naloxone hydrochloride (IR-OXN 20/10), 10 mg oxycodone hydrochloride/5 mg naloxone hydrochloride (IR-OXN10/5), 5 mg oxycodone hydrochloride/2.5 mg naloxone hydrochloride (IR-OXN5/2.5) and 2.5 mg oxycodone hydrochloride/1.25 mg naloxone hydrochloride (IR-OXN2.5/1.25) were manufactured as described below. Their composition is detailed in Table 1.

TABLE 1

Quantitative composition of IR-OXN Tablets

| Tablet Core | IR-OXN2.5/1.25 mg/tablet | IR-OXN5/2.5 mg/tablet | IR-OXN10/5 mg/tablet | IR-OXN20/10 mg/tablet | Function | Reference to Standard |
|---|---|---|---|---|---|---|
| Active constituents | | | | | | |
| Oxycodone hydrochloride anhydrous[1] | 2.50 | 5.00 | 10.00 | 20.00 | Active ingredient | Ph. Eur. |
| Oxycodone base equivalent | 2.25 | 4.50 | 9.00 | 18.00 | | |
| Naloxone hydrochloride dihydrate[2] | 1.36 | 2.73 | 5.45 | 10.90 | Active ingredient | Ph. Eur. |
| Naloxone hydrochloride anhydrous[2] | 1.25 | 2.50 | 5.00 | 10.00 | | |
| Naloxone base equivalent | 1.125 | 2.25 | 4.50 | 9.00 | | |
| Other Constituents | | | | | | |
| StarLac ® Comprising of Lactose monohydrate 85% Maize starch 15% | 121 | 118 | 112 | 99.0 | Disintegrant/ Diluent | Ph. Eur. |
| Microcrystalline cellulose PH102 | 20.0 | 18.9 | 17.8 | 15.8 | Diluent | Ph. Eur. |
| Croscarmellose sodium | 3.00 | 3.00 | 3.00 | 3.00 | Disintegrant | Ph. Eur. |

TABLE 1-continued

Quantitative composition of IR-OXN Tablets

| Tablet Core | Constituent | | | | Function | Reference to Standard |
|---|---|---|---|---|---|---|
| | IR-OXN2.5/1.25 mg/tablet | IR-OXN5/2.5 mg/tablet | IR-OXN10/5 mg/tablet | IR-OXN20/10 mg/tablet | | |
| Sodium stearyl fumarate | 2.25 | 2.25 | 2.25 | 2.25 | Lubricant | Ph. Eur. |
| Total core | 150 | 150 | 150 | 150 | | |
| Film Coat | | | | | | |
| Opadry ® II° 85F34131 | 4.00 | — | — | — | Coating | supplier specification |
| Opadry ® II° 85F36609 | — | 4.00 | — | — | Coating | supplier specification |
| Opadry ® II° 85F21814 | — | — | 4.00 | — | Coating | supplier specification |
| Opadry ® II° 85F32648 | — | — | — | 4.00 | Coating | supplier specification |
| Purified water* | — | — | — | — | Solvent | Ph. Eur. |
| Total tablet weight | 154 | 154 | 154 | 154 | | |

[1]calculated based on assay
[2]calculated based on assay and moisture content
*evaporated during processing
°quantitative composition: see Tables 2-5

TABLE 2

Quantitative Composition of the Film Coat for IR-OXN2.5/1.25

| Opadry II Pink 85F34131 | % (w/w) | Reference to Standard |
|---|---|---|
| Polyvinyl alcohol part hydrolized | 40.0 | Ph. Eur. |
| Titanium dioxide (E171) | 23.88 | Ph. Eur. |
| Macrogol 3350 | 20.20 | Ph. Eur. |
| Talc | 14.80 | Ph. Eur. |
| Carmine (E120) | 1.12 | EC directive 95/45EC |

TABLE 3

Quantitative Composition of the Film Coat for IR-OXN5/2.5

| Opadry II Brown 85F36609 | % (w/w) | Reference to Standard |
|---|---|---|
| Polyvinyl alcohol part hydrolized | 40.0 | Ph. Eur. |
| Titanium dioxide (E171) | 15.11 | Ph. Eur. |
| Macrogol 3350 | 20.20 | Ph. Eur. |
| Talc | 14.80 | Ph. Eur. |
| Iron oxide yellow (E172) | 7.51 | EC directive 95/45EC |
| Iron oxide black (E172) | 2.35 | EC directive 95/45EC |
| Iron oxide red (E172) | 0.03 | EC directive 95/45EC |

TABLE 4

Quantitative Composition of the Film Coat for IR-OXN10/5

| Opadry II Green 85F21814 | % (w/w) | Reference to Standard |
|---|---|---|
| Polyvinyl alcohol part hydrolized | 40.0 | Ph. Eur. |
| Titanium dioxide (E171) | 12.57 | Ph. Eur. |
| Macrogol 3350 | 20.2 | Ph. Eur. |
| Talc | 14.8 | Ph. Eur. |
| Iron oxide yellow (E172) | 9.00 | EC directive 95/45EC |
| FD&C blue #2 indigo carmine aluminium lake (E132) | 3.43 | EC directive 95/45EC |

TABLE 5

Quantitative Composition of the Film Coat for IR-OXN20/10

| Opadry II Yellow 85F32648 | % (w/w) | Reference to Standard |
|---|---|---|
| Polyvinyl alcohol part hydrolized | 40.0 | Ph. Eur. |
| Titanium dioxide (E171) | 8.00 | Ph. Eur. |
| Macrogol 3350 | 20.2 | Ph. Eur. |
| Talc | 14.8 | Ph. Eur. |
| Iron oxide yellow (E172) | 17.0 | EC directive 95/45EC |

The constituents of Tables 1 to 5 were processed as depicted in the flow chart of FIG. 1.

In detail, microcrystalline cellulose, croscarmellose sodium and the active ingredients were screened through a 500 μm sieve to remove any agglomerates, added to the blender with the StarLac® and blended until a uniform blend was achieved. Sieving of the StarLac® was not required as it is free flowing. The lubricant, sodium stearyl fumarate, was screened through a 500 μm sieve, added to the blend and further blended. The blend was then compressed into tablets by direct compression. To ensure acceptable blend uniformity a milled grade of naloxone hydrochloride was utilized to obtain a comparable particle size range to oxycodone hydrochloride and the other excipients.

A coloured, cosmetic film coat was applied to provide differentiation between the different strengths of the product. The conditions for film coating were optimised to consistently produce coated tablets of the appropriate aesthetic quality.

The IR-OXN 20/10, IR-OXN10/5, IR-OXN512.5 and IR-OXN2.5/1.25 tablets were then tested by the Ph. Eur. Paddle test.

In all cases, at 15 min more than 95% of oxycodone hydrochloride and naloxone hydrochloride were released.

Example 2

Single Dose Study to Compare the Dose Proportionality of IR-OXN 20/10, IR-OXN10/5, IR-OXN5/2.5 and IR-OXN2.5/1.25 Tablets in Healthy Subjects

1. Objective

The objective was to assess dose proportionality of oxycodone and naloxone (or surrogate naloxone-3-glucuronide) from the IR OXN tablets at strengths of 2.5/1.25 mg, 5/2.5 mg, 10/5 mg and 20/10 mg.

2. Test Population

It was planned to randomise a total of 21 healthy adult, male and female subjects to receive study medication with the aim that 18 subjects completed the study and provided valid pharmacokinetic data. A total of 21 subjects were actually enrolled and randomized and 20 subjects completed the study.

Inclusion Criteria

Subjects who were to be included in the study were those who met all of the following criteria:
1. Male or female subjects aged 18 to 55 inclusive.
2. Female subjects who were sexually active or became sexually active during the study had to be willing to use highly effective methods of contraception throughout the study. A highly effective method of birth control was defined as one which results in a low failure rate (i.e. less than 1% per year) when used consistently and correctly such as sterilisation, implants, injectables, combined oral contraceptives, some intrauterine devices, or vasectomised partner.
3. Female subjects less than one year post-menopausal had to have a negative serum pregnancy test and be non-lactating.
4. Female subjects who had been post-menopausal for >1 year and had elevated serum follicle-stimulating hormone (FSH) or were treated with hormone replacement therapy (HRT).
5. Male subjects had to be willing to use contraception with their partners throughout the study and for 30 days after completion of the study and agreed to inform the Investigator if their partner became pregnant during this time
6. Body weight ranging from 55 to 100 kg and a body mass index (BMI)≥18 and ≤29.
7. Healthy and free of significant abnormal findings as determined by medical history, physical examination, vital signs, laboratory tests and electrocardiogram (ECG).
8. Willing to eat all the food supplied throughout the study.
9. The subject's primary care physician had confirmed within the previous 12 months that there was nothing in the subject's medical history that would have precluded their enrolment into a clinical study.

Exclusion Criteria

Subjects who were to be excluded from the study were those who met any of the following criteria:
1. Any history of drug or alcohol abuse.
2. Any history of conditions that might have interfered with drug absorption, distribution, metabolism or excretion.
3. Use of opioid or opioid antagonist-containing medication in the previous 30 days.
4. Any history of frequent nausea or vomiting regardless of aetiology.
5. Any history of seizures or symptomatic head trauma.
6. Participation in a clinical drug study during the 90 days preceding the initial dose in this study.
7. Any significant illness during the 4 weeks preceding entry into this study.
8. Use of any medication including vitamins, herbal and/or mineral supplements during the 7 days preceding the initial dose or during the course of this study (with the exception of the continued use of HRT and contraceptives).
9. Refusal to abstain from food for 8 hours preceding and 4 hours following study drug administration and to abstain from caffeine or xanthine containing beverages entirely during each confinement.
10. Weekly alcohol intake exceeding the equivalent of 14 units/week for females and 21 units/week for males.
11. Consumption of alcoholic beverages within 48 hours before study drug administration, and refusal to abstain from alcohol for at least 48 hours after study drug administration.
12. History of smoking within 45 days of study drug administration and refusal to abstain from smoking during the study.
13. Blood or blood products donated within 30 days prior to study drug administration or any time during the study, except as required by the protocol.
14. Positive results of urine drug screen, alcohol test, hepatitis B surface antigen (HBsAg), Hepatitis C antibody, or human immunodeficiency virus (HIV) tests.
15. Known sensitivity to oxycodone, naloxone, naltrexone or related compounds.
16. Refusal to allow their primary care physician to be informed.

The demographic data of the subject population are shown in Table 6.

The study population comprised 14 male and seven female subjects with a mean age of 31 years (range: 21 to 53 years). Twenty subjects were Caucasian and one subject was black.

TABLE 6

Summary of Demography and Baseline Characteristics: Safety Population

| Demographic | Statistic | Female (N = 7) | Male (N = 14) | Total (N = 21) |
|---|---|---|---|---|
| Age (years) | n | 7 | 14 | 21 |
| | Mean (SD) | 29.7 (11.13) | 31.7 (9.67) | 31.0 (9.95) |
| | Median | 25 | 26.5 | 26 |
| | Min, Max | 22, 53 | 21, 50 | 21, 53 |
| Race, n (%) | Asian | 0 | 0 | 0 |
| | Black | 0 | 1 (7.1%) | 1 (4.8%) |
| | Caucasian | 7 (100%) | 13 (92.9%) | 20 (95.2%) |
| | Other | 0 | 0 | 0 |

TABLE 6-continued

Summary of Demography and Baseline Characteristics: Safety Population

| Demographic | Statistic | Female (N = 7) | Male (N = 14) | Total (N = 21) |
|---|---|---|---|---|
| Gender, n (%) | Female | | | 7 (33.3%) |
| | Male | | | 14 (66.7%) |
| Weight (kg) | n | 7 | 14 | 21 |
| | Mean (SD) | 65.29 (8.480) | 83.29 (10.455) | 77.29 (12.972) |
| | Median | 61 | 83.5 | 76 |
| | Min, Max | 57, 76 | 67, 98.5 | 57, 98.5 |
| Height (cm) | n | 7 | 14 | 21 |
| | Mean (SD) | 166.1 (6.15) | 178.5 (6.72) | 174.4 (8.74) |
| | Median | 166 | 179.5 | 175 |
| | Min, Max | 155, 175 | 164, 190 | 155, 190 |
| BMI (kg/m$^2$) | n | 7 | 14 | 21 |
| | Mean (SD) | 23.67 (2.999) | 26.08 (2.367) | 25.28 (2.773) |
| | Median | 22.9 | 26.7 | 25.4 |
| | Min, Max | 19.7, 27.6 | 22.1, 29.4 | 19.7, 29.4 |

3. Study Design

The study was an open-label, single-dose, 4-treatment, 4-period, randomised crossover study in healthy male and female subjects conducted at a single study centre. Each subject received single doses of IR OXN tablet at strengths of 2.5/1.25 mg, 5/2.5 mg, 10/5 mg and 20/10 mg. Subjects received each of the four treatments according to a random allocation schedule (RAS), with at least a 7-day washout period between each dosing.

Subjects attended a screening visit within 21 days of the first dosing day of Study Period 1. Eligible subjects then checked into the study unit on the day before dosing in each study period. Subjects were administered the appropriate study drug in a fasted state the following morning.

Pharmacokinetic blood samples were taken for 36 hours after administration of study drug in each study period, and subjects were discharged after the 36-hour blood sample.

During each study period, vital signs (pulse, blood pressure, and respiration rate) were monitored pre-dose and then at 1, 2, 4, 6, 8, 12, 24, and 36 hours after dosing. Oral temperature was monitored pre-dose, and at 24 and 36 hours after dosing. Adverse events were recorded throughout the study. Subjects attended a post-study visit 7 to 10 days after their last dose of study medication in the case of completion/discontinuation from the study.

Figure 2:
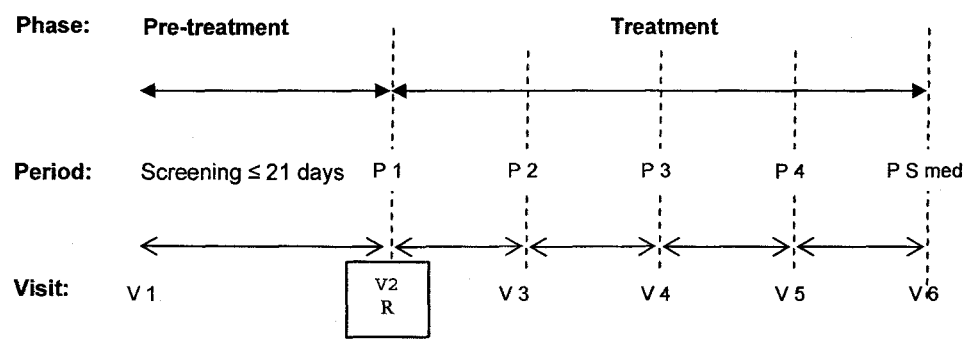
FIG. 2 depicts the treatment schedule of the clinical trial described in Experiment 2.

The study design is set forth in FIG. 2. The abbreviations in FIG. 2 are as follows:

R=Randomisation

P1, P2, P3, P4=Periods 1-4 each consisted of a single dose of study drug according to a RAS followed by blood sampling and safety assessments up to 36 hours post-dose. There was a minimum 7-day washout between doses of study drug in each study period.

PS med=post-study medical 7-10 days after last dose of study drug in the case of completion/discontinuation from the study.

V1 to V6=visits

4. Pharmacokinetic Sample Collection

Beginning on Days 1, 8, 15 and 22, serial blood collections (6 mL each) were obtained at the following times:

Pre-dose, and at 0.25, 0.5, 0.75, 1, 1.25, 1.5, 2, 2.5, 3, 3.5, 4, 5, 6, 8, 10, 12, 16, 24, 28, 32, and 36 hours post-dose (22 blood samples per dosing period).

The acceptable time window from the nominal blood sampling times was ±5 minutes.

Approximately 528 mL blood (22 samples of 6 mL on four occasions) was taken from each subject for pharmacokinetic measurements.

5. Treatments Administered

The treatment was administered orally, in a fasted state, as follows:

A: One IR OXN tablet 2.5/1.25 mg
B: One IR OXN tablet 5/2.5 mg
C: One IR OXN tablet 10/5 mg
D: One IR OXN tablet 20/10 mg Naltrexone HCl was administered orally with all treatments (A to D) to reduce opioid-related adverse events. Naltrexone HCl tablet 50 mg (Nalorex® tablets, Bristol-Myers Squibb Pharmaceuticals Ltd). One naltrexone tablet was administered at −13 h, −1 h, and +11 h relative to study drug dosing, in each study period.

6. Pharmacokinetic Parameters

The following pharmacokinetic parameters were calculated from the plasma concentrations of oxycodone, noroxycodone, oxymorphone, noroxymorphone, naloxone, 6β-naloxol, naloxone-3-glucuronide and 6β-naloxol-3-glucuronide:

Area under the plasma concentration-time curve measured from the time of dosing to the last measurable concentration (AUCt)

Area under the plasma concentration-time curve measured from the time of dosing and extrapolated to infinity (AUCinf)

Maximum observed plasma concentration (Cmax)
Time of maximum observed plasma concentration (tmax)
Terminal phase rate constant (LambdaZ)
Terminal phase half-life (t1/2Z)

AUC values for oxycodone, noroxycodone, oxymorphone, noroxymorphone and naloxone-3-glucuronide were reported in ng·h/mL, and Cmax values in ng/mL. For naloxone, 6β-naloxol and 6β-naloxol-3-glucuronide, the AUC values were reported in pg·h/mL and Cmax values in pg/mL.

AUCt values were calculated using the linear trapezoidal method. Where possible, LambdaZ was estimated using those points determined to be in the terminal log-linear phase.

t1/2Z was determined from the ratio of ln 2 to LambdaZ. The areas under the plasma concentration-time curve between the last measured point and infinity were calculated from the ratio of the final observed plasma concentration (Clast) to LambdaZ. This was then added to the AUCt to yield AUCINF.

All pharmacokinetic calculations were performed with WinNonlin Enterprise Edition, version 4.1.

Particularly with the lower doses, the plasma concentrations of naloxone were extremely low and a full pharmacokinetic characterisation was not possible. In the results and discussion sections below, greater emphasis is placed on its primary metabolite, naloxone-3-glucuronide.

The primary objective of the study was to determine dose proportionality of oxycodone and naloxone (or surrogate naloxone-3-glucuronide) from the IR OXN tablet at strengths of 2.1/1.25 mg, 5/2.5 mg, 10/5 mg and 20/10 mg.

Dose-adjusted relative systemic bioavailabilies were calculated from the ratios of AUCt and, where possible, AUCINF values. The comparisons of interest for oxycodone, naloxone and their metabolites were:

OXN IR tablet 5/2.5 mg vs. OXN IR tablet 2.5/1.25 mg
OXN IR tablet 10/5 mg vs. OXN IR tablet 2.5/1.25 mg
OXN IR tablet 20/10 mg vs. OXN IR tablet 2.5/1.25 mg The maximum observed plasma concentration ($C_{max}$) and times that Cmax occurred (tmax) were obtained directly from the reported plasma concentration-time data. Dose-adjusted Cmax ratios were calculated making the comparisons outlined above.

7. Results

Figure 3:
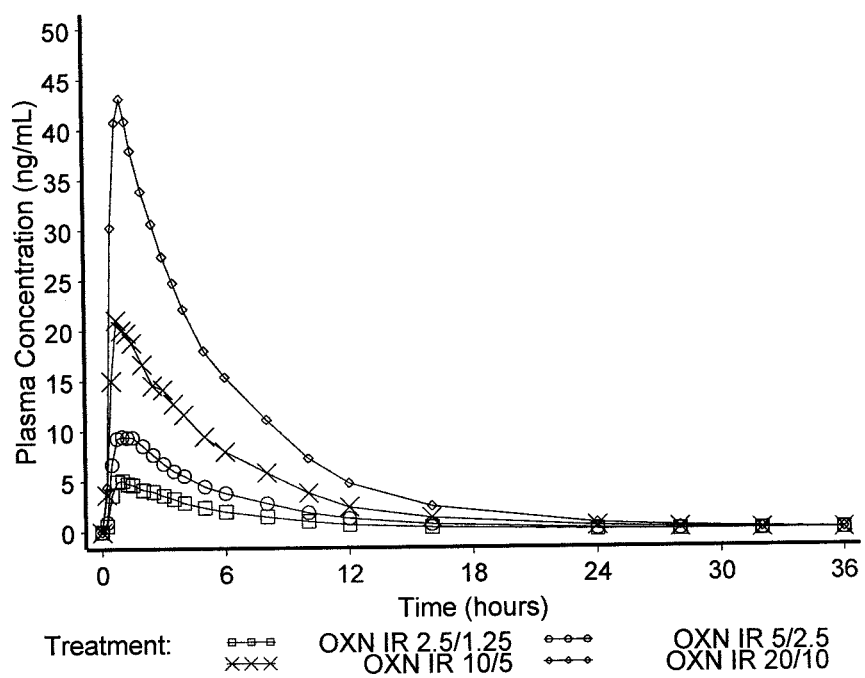
FIG. 3 depicts the mean blood plasma concentration of oxycodone as determined for IR OXN 2.5/1.25, IR OXN 5/2.5, IR OXN 10/5 and IR OXN 20/10 in Experiment 2 for 21 subjects.
Figure 4:
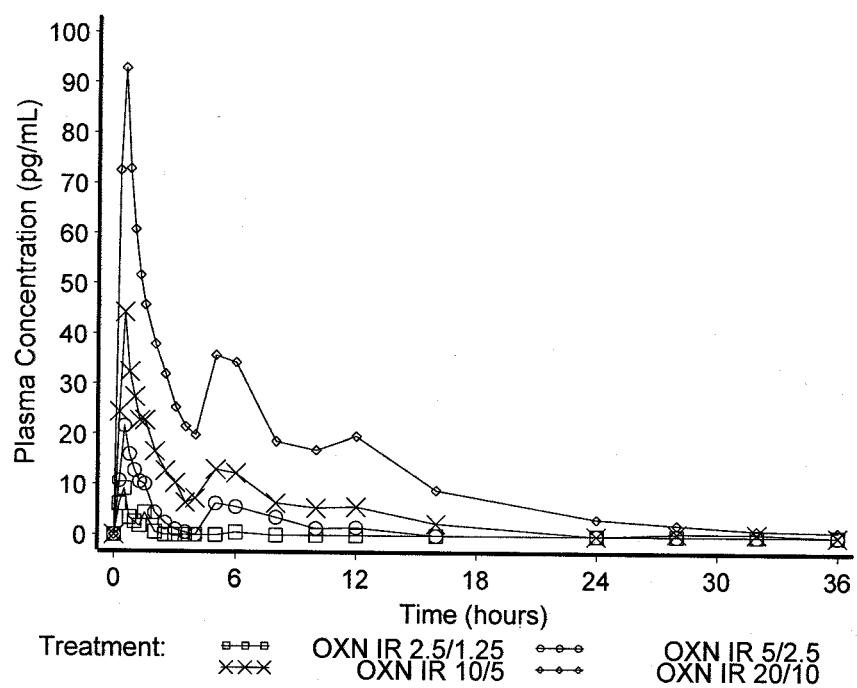
FIG. 4 depicts the mean blood plasma concentration of naloxone as determined for IR OXN 2.5/1.25, IR OXN 5/2.5, IR OXN 10/5 and IR OXN 20/10 in Experiment 2 for 21 subjects.
Figure 5:
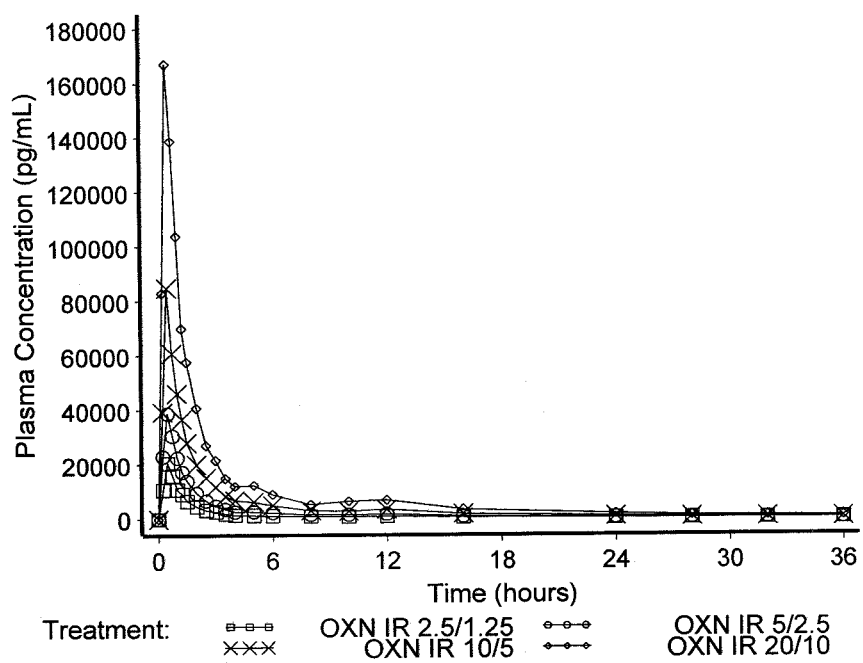
FIG. 5 depicts the mean blood plasma concentration of naloxone-3-glucuronide as determined for IR OXN 2.5/1.25, IR OXN 5/2.5, IR OXN 10/5 and IR OXN 20/10 in Experiment 2 for 21 subjects.

The results for the pharmacokinetic parameters of oxycodone, naloxone and naloxone-3-glucuronide are shown in FIGS. 3 to 5 respectively for the analysed 21 subjects.

Oxycodone

The summary statistics for oxycodone are shown in Table 7.

TABLE 7

Summary Statistics for Oxycodone Pharmacokinetic Parameters

| PK Parameters | Statistics | Study Treatment | | | |
| --- | --- | --- | --- | --- | --- |
| | | OXN IR 2.5/1.25 mg | OXN IR 5/2.5 mg | OXN IR 10/5 mg | OXN IR 20/10 mg |
| AUCt (ng · h/mL) | n | 21 | 20 | 20 | 20 |
| | Geometric Mean | 28.7 | 57.2 | 120.0 | 236.2 |
| | Geometric SE | 1.06 | 1.06 | 1.06 | 1.05 |
| | Exponentiated LS Mean | 28.7 | 57.3 | 118.8 | 234.4 |
| AUCINF (ng · h/mL) | n | 21 | 20 | 18 | 20 |
| | Geometric Mean | 29.8 | 58.3 | 122.7 | 237.2 |
| | Geometric SE | 1.06 | 1.06 | 1.06 | 1.05 |
| | Exponentiated LS Mean | 29.8 | 58.4 | 119.8 | 235.3 |
| Cmax (ng/mL) | n | 21 | 20 | 20 | 20 |
| | Geometric Mean | 6.19 | 11.83 | 23.28 | 49.30 |
| | Geometric SE | 1.051 | 1.058 | 1.076 | 1.081 |
| | Exponentiated LS Mean | 6.18 | 11.81 | 23.63 | 49.80 |
| tmax (h) | n | 21 | 20 | 20 | 20 |
| | Median | 1 | 1 | 0.75 | 1 |
| | Range | 0.5, 3 | 0.5, 2 | 0.25, 4 | 0.5, 3 |
| t½Z (h) | n | 21 | 20 | 18 | 20 |
| | Mean | 4.00 | 3.96 | 3.99 | 4.04 |
| | SE | 0.212 | 0.167 | 0.165 | 0.137 |
| | LS Mean | 4.00 | 3.95 | 3.98 | 4.01 |
| LambdaZ (h⁻¹) | n | 21 | 20 | 18 | 20 |
| | Mean | 0.184 | 0.181 | 0.180 | 0.175 |
| | SE | 0.0102 | 0.0076 | 0.0087 | 0.0059 |
| | LS Mean | 0.184 | 0.181 | 0.181 | 0.177 |

Similar values were recorded for all the IR OXN tablet strengths for the tmax and t1/2Z parameters.

Each of the IR OXN tablet strengths provided an equivalent dose-adjusted bioavailability of oxycodone to IR OXN tablet 2.5/1.25 mg in terms of AUCt, AUCINF and Cmax, with the 90% confidence intervals for each of the comparison ratios falling within the 80-125% limits of acceptability for bioequivalence. Results of the statistical analysis of oxycodone pharmacokinetic parameters are presented in Table 8.

TABLE 8

Statistical Analysis of Dose Proportionality of Treatments for Oxycodone Pharmacokinetic Parameters

| Treatment comparisons | AUCt Test/Ref[a] | 90% CI[b] | AUCINF Test/Ref[a] | 90% CI[b] | Cmax Test/Ref[a] | 90% CI[b] |
|---|---|---|---|---|---|---|
| OXN IR 5/2.5 vs OXN IR 2.5/1.25 | 100.0 | 95.0, 105.2 | 98.2 | 93.4, 103.2 | 95.5 | 87.6, 104.0 |
| OXN IR 10/5 vs OXN IR 2.5/1.25 | 103.6 | 98.4, 109.0 | 100.6 | 95.5, 106.0 | 95.5 | 87.7, 104.1 |
| OXN IR 20/10 vs OXN IR 2.5/1.25 | 102.2 | 97.1, 107.6 | 98.8 | 94.0, 103.9 | 100.7 | 92.4, 109.7 |

CI = confidence interval
[a]Estimate from mixed-effects linear model. Natural log parameter estimates calculated by transforming the log-scale estimates back to the linear scale, that is estimates of ratios.
[b]90% confidence intervals obtained by transforming the confidence intervals on the log scale to the ratio scale.
Ratios are dose-adjusted Naloxone-3-glucuronide The pharmacokinetic parameters of naloxone-3-glucuronide were analysed as a surrogate for naloxone.

The summary statistics for naloxone-3-glucuronide are shown in Table 9.

TABLE 9

Summary Statistics for Naloxone-3-glucuronide Pharmacokinetic Parameters

| PK Parameters | Statistics | Study Treatment | | | |
|---|---|---|---|---|---|
| | | OXN IR 2.5/1.25 mg | OXN IR 5/2.5 mg | OXN IR 10/5 mg | OXN IR 20/10 mg |
| AUCt (ng · h/mL) | n | 21 | 20 | 20 | 20 |
| | Geometric Mean | 38.6 | 79.4 | 162.5 | 321.9 |
| | Geometric SE | 1.06 | 1.05 | 1.05 | 1.06 |
| | Exponentiated LS Mean | 38.6 | 79.8 | 160.6 | 319.6 |
| AUCINF (ng · h/mL) | n | 12 | 11 | 10 | 10 |
| | Geometric Mean | 40.5 | 90.7 | 169.7 | 336.4 |
| | Geometric SE | 1.07 | 1.06 | 1.07 | 1.11 |
| | Exponentiated LS Mean | 40.7 | 86.3 | 167.8 | 322.6 |
| Cmax (ng/mL) | n | 21 | 20 | 20 | 20 |
| | Geometric Mean | 21.10 | 46.27 | 89.11 | 177.24 |
| | Geometric SE | 1.096 | 1.082 | 1.086 | 1.100 |
| | Exponentiated LS Mean | 21.12 | 46.51 | 87.46 | 175.98 |
| tmax (h) | n | 21 | 20 | 20 | 20 |
| | Median | 0.5 | 0.5 | 0.5 | 0.5 |
| | Range | 0.25, 0.75 | 0.25, 1 | 0.25, 2.5 | 0.25, 3 |
| t½Z (h) | n | 12 | 11 | 10 | 10 |
| | Mean | 10.04 | 8.88 | 11.51 | 15.68 |
| | SE | 1.246 | 1.586 | 2.215 | 3.695 |
| | LS Mean | 9.80 | 8.58 | 12.09 | 15.72 |
| LambdaZ (h$^{-1}$) | n | 12 | 11 | 10 | 10 |
| | Mean | 0.080 | 0.096 | 0.082 | 0.072 |
| | SE | 0.0091 | 0.0109 | 0.0156 | 0.0152 |
| | LS Mean | 0.083 | 0.096 | 0.076 | 0.070 |

Similar values were recorded for all the IR OXN tablet strengths for tmax. The mean t1/2Z values ranged from 8.88 hours for the IR OXN 5/2.5 mg tablet strength to 15.68 hours for the IR OXN 20/10 mg tablet strength.

Each of the IR OXN tablet strengths provided an equivalent dose-adjusted bioavailability of naloxone-3-glucuronide to IR OXN tablet 2.5/1.25 mg in terms of AUCt, AUCINF and Cmax, with the 90% confidence intervals for each of the comparison ratios falling within the 80-125% limits of acceptability for bioequivalence, except for the upper 90% confidence interval for the ratio of Cmax for IR OXN 5/2.5 mg vs. IR OXN 2.5/1.25 mg, which was 131.9%. Results of the statistical analysis of naloxone-3-glucuronide pharmacokinetic parameters are presented in Table 10.

TABLE 10

Statistical Analysis of Dose Proportionality of Treatments for Naloxone-3-Gucuronide Pharmacokinetic Parameters

| Treatment comparisons | AUCt | | AUCINF | | Cmax | |
|---|---|---|---|---|---|---|
| | Test/Ref[a] | 90% CI[b] | Test/Ref[a] | 90% CI[b] | Test/Ref[a] | 90% CI[b] |
| OXN IR 5/2.5 vs OXN IR 2.5/1.25 | 103.4 | 94.7, 112.8 | 106.2 | 91.6, 123.0 | 110.1 | 92.0, 131.9 |
| OXN IR 10/5 vs OXN IR 2.5/1.25 | 104.0 | 95.3, 113.5 | 103.2 | 88.2, 120.8 | 103.5 | 86.5, 124.0 |
| OXN IR 20/10 vs OXN IR 2.5/1.25 | 103.4 | 94.8, 112.9 | 99.2 | 85.8, 114.7 | 104.2 | 87.0, 124.8 |

CI = confidence interval
[a]Estimate from mixed-effects linear model. Natural log parameter estimates calculated by transforming the log-scale estimates back to the linear scale, that is estimates of ratios.
[b]90% confidence intervals obtained by transforming the confidence intervals on the log scale to the ratio scale.
Ratios are dose-adjusted 8. Conclusions Dose-adjusted bioequivalence was achieved for each of the OXN IR tablet strengths relative to IR OXN tablet 2.5/1.25 mg for the major analytes of oxycodone and naloxone-3-glucuronide. Dose proportionality has been confirmed for the IR OXN tablet strengths ranging from 2.5/1.25 mg to 20/10 mg. The plasma concentrations of naloxone were extremely low, particularly with the lower doses, confirming the results of previous studies and supporting the analysis of the surrogate naloxone-3-glucuronide.

Example 3

Single Dose Study to Compare Bioavailability of IR-OXN 20/10 Tablets with Oxycodone/Naloxone Prolonged Release Tablet 20/10 mg (Targin®) in Healthy Subjects 1. Objective The objectives of this study were to assess the pharmacokinetics, bioavailability and safety of OXN IR tablet 20/10 mg, OXN PR tablet 20/10 mg, and oxycodone IR capsule 20 mg when administered in a fasted state, to healthy subjects.

2. Test Population

It was planned to randomise a total of 21 healthy adult, male and female subjects to receive study medication with the aim that 18 subjects completed the study and provided valid pharmacokinetic data. A total of 22 subjects were actually enrolled and randomised and 21 subjects completed the study. One subject discontinued before study medication (ie, OXN or oxycodone) administration.

Inclusion Criteria

Subjects who were to be included in the study were those who met all of the following criteria:

1. Male or female subjects aged 18 to 55 inclusive.
2. Female subjects who were sexually active or became sexually active during the study had to be willing to use highly effective methods of contraception throughout the study. A highly effective method of birth control was defined as one which results in a low failure rate (i.e. less than 1% per year) when used consistently and correctly such as sterilisation, implants, injectables, combined oral contraceptives, some intrauterine devices, or vasectomised partner.
3. Female subjects less than one year post-menopausal had to have a negative serum pregnancy test and be non-lactating.
4. Female subjects who had been post-menopausal for >1 year and had elevated serum follicle-stimulating hormone (FSH) or were treated with hormone replacement therapy (HRT).
5. Body weight ranging from 55 to 100 kg and a body mass index (BMI)≥18 and ≤29.
6. Healthy and free of significant abnormal findings as determined by medical history, physical examination, vital signs, laboratory tests and electrocardiogram (ECG).
7. Willing to eat all the food supplied throughout the study.
8. The subject's primary care physician had confirmed within the previous 12 months that the subject was suitable for taking part in clinical studies.

Exclusion Criteria

Subjects who were to be excluded from the study were those who met any of the following criteria:

1. Any history of drug or alcohol abuse.
2. Any history of conditions that might have interfered with drug absorption, distribution, metabolism or excretion.
3. Use of opioid or opioid antagonist-containing medication in the previous 30 days.
4. Any history of frequent nausea or vomiting regardless of aetiology.
5. Any history of seizures or symptomatic head trauma.

6. Participation in a clinical drug study during the 90 days preceding the initial dose in this study.

7. Any significant illness during the 4 weeks preceding entry into this study.

8. Use of any medication including vitamins, herbal and/or mineral supplements during the 7 days preceding the initial dose or during the course of this study (with the exception of the continued use of HRT and contraceptives).

9. Refusal to abstain from food for 8 hours preceding and 4 hours following study drug administration and to abstain from caffeine or xanthine containing beverages entirely during each confinement.

10. Weekly alcohol intake exceeding the equivalent of 14 units/week for females and 21 units/week for males.

11. Consumption of alcoholic beverages within 48 hours before study drug administration, and refusal to abstain from alcohol for at least 48 hours after study drug administration.

12. History of smoking within 45 days of study drug administration and refusal to abstain from smoking during the study.

13. Blood or blood products donated within 30 days prior to study drug administration or any time during the study, except as required by this protocol.

14. Positive results of urine drug screen, alcohol test, hepatitis B surface antigen (HBsAg), Hepatitis C antibody, or human immunodeficiency virus (HIV) tests.

15. Known sensitivity to oxycodone, naloxone, naltrexone or related compounds.

16. Refusal to allow their primary care physician to be informed.

The demographic data of the subject population are shown in Table 11. The study population comprised 11 male and 10 female subjects with a mean age of 33 years (range: 20 to 52 years). All subjects were Caucasian.

TABLE 11

Summary of Demography and Baseline Characteristics

| Demographic | Statistic | Female (N = 10) | Male (N = 11) | Total (N = 21) |
|---|---|---|---|---|
| Age (years) | n | 10 | 11 | 21 |
| | Mean (SD) | 32.3 (8.67) | 34.5 (10.48) | 33.4 (9.48) |
| | Median | 29 | 36 | 35 |
| | Min, Max | 22, 44 | 20, 52 | 20, 52 |
| Race, n (%) | Asian | 0 | 0 | 0 |
| | Black | 0 | 0 | 0 |
| | Caucasian | 10 (100%) | 11 (100%) | 21 (100%) |
| | Other | 0 | 0 | 0 |
| Gender, n (%) | Female | | | 10 (47.6%) |
| | Male | | | 11 (52.4%) |
| Weight (kg) | n | 10 | 11 | 21 |
| | Mean (SD) | 65.23 (6.691) | 78.42 (12.195) | 72.14 (11.835) |
| | Median | 63.25 | 78.3 | 71.7 |
| | Min, Max | 56.9, 75 | 58, 97.3 | 56.9, 97.3 |
| Height (cm) | n | 10 | 11 | 21 |
| | Mean (SD) | 165.1 (4.82) | 180.1 (6.07) | 173.0 (9.37) |
| | Median | 165 | 181 | 173 |
| | Min, Max | 156, 173 | 168, 191 | 156, 191 |
| BMI (kg/m$^2$) | n | 10 | 11 | 21 |
| | Mean (SD) | 23.94 (2.289) | 24.07 (2.771) | 24.01 (2.490) |
| | Median | 23.5 | 24.2 | 23.9 |
| | Min, Max | 21.4, 28.7 | 18.5, 28 | 18.5, 28.7 |

3. Study Design

The study was an open-label, single-dose, 3-treatment, 3-period, randomised crossover. Each subject received single oral doses of IR OXN tablet 20/10 mg, oxycodone IR capsule 20 mg and OXN PR tablet 20/10 mg (Targin®). Subjects received each of the three treatments according to a random allocation schedule (RAS), with at least a 7-day washout period between each dosing.

Subjects attended a screening visit within 21 days of the first dosing day of Study Period 1. Eligible subjects then checked into the study unit on the day before dosing in each study period. Subjects were administered the appropriate study drug in a fasted state the following morning.

Pharmacokinetic blood samples were taken for 36 hours after administration of study drug in each study period, and subjects were discharged after the 36-hour blood sample.

During each study period, vital signs (pulse, blood pressure, and respiration rate) were monitored pre-dose and then at 1, 2, 4, 6, 8, 12, 24, and 36 hours after dosing. Oral temperature was monitored pre-dose, and at 24 and 36 hours after dosing. Adverse events were recorded throughout the study.

Subjects attended a post-study visit 4 to 7 days after their last dose of study medication in the case of completion/discontinuation from the study.

Figure 6:
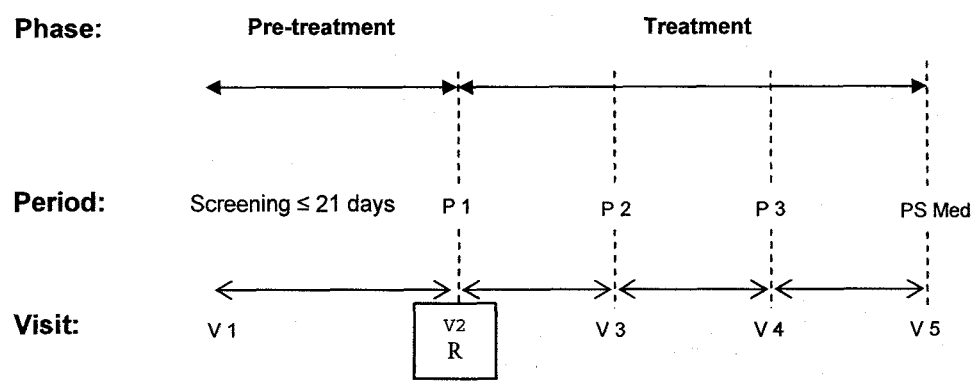
FIG. 6 depicts the treatment schedule of the clinical trial described in Experiment 3.

The study design is set forth in FIG. 6. The abbreviations in FIG. 6 are as follows:
R=Randomisation.
P1, P2, P3=Periods 1 to 3 each consisted of a single dose of study drug followed by blood sampling and safety assessments up to 36 h. There was a 7-day washout between doses of study drug in each study period. Naltrexone was also administered at −13 h, −1 h and +11 h relative to study drug dosing in each study period.
PS med=Post-study medical 4 to 7 days after last study drug dose in the case of completion or discontinuation from the study. Subjects who received naltrexone only prior to discontinuation from the study underwent a post-study medical prior to discharge from the unit.
V1 to V5=Visits

4. Pharmacokinetic Sample Collection

Beginning on Days 1, 8, and 15, serial blood collections (6 ml each) were obtained at the following times:
Treatments A and B:
Pre-dose, and at 0.25, 0.5, 0.75, 1, 1.25, 1.5, 2, 2.5, 3, 3.5, 4, 5, 6, 8, 10, 12, 16, 24, 28, 32, and 36 hours post-dose (22 blood samples per dosing period).
Treatment C:
Pre-dose, and at 0.5, 1, 1.5, 2, 2.5, 3, 3.5, 4, 5, 6, 8, 10, 12, 16, 24, 28, 32, and 36 hours post dose (19 blood samples per dosing period).

If a subject experienced vomiting within 12 hours after dosing with OXN PR tablet 20/10 or within 6 hours after dosing with OXN IR tablet 20/10 or oxycodone IR capsule 20 mg, no further pharmacokinetic blood sampling was undertaken for that subject for the rest of the study period.

The acceptable time window from the nominal blood sampling times was +5 minutes.

Approximately 378 ml blood (22 samples of 6 ml on two occasions and 19 samples of 6 ml on one occasion) was taken from each subject for pharmacokinetic measurements.

5. Treatments Administered

The treatments administered in this study are presented below:
Test Treatments:
IR OXN tablet 20/10 mg. The treatment was administered orally, in a fasted state, as follows:
Treatment A: One OXN IR tablet 20/10 mg
Reference Treatments:
IR Oxycodone capsule 20 mg (OxyNorm®, Napp Pharmaceuticals Ltd, UK). The treatment was administered orally, in a fasted state, as follows:
Treatment B: One oxycodone IR capsule 20 mg
OXN PR tablet 20/10 mg (Targin®). Manufactured by Bard Pharmaceuticals Ltd, UK. The treatment was administered orally, in a fasted state, as follows:
Treatment C: One OXN PR tablet 20/10 mg Study drug dosing occurred under the cover of naltrexone to reduce the risk of opioid-related adverse events in each study period. Naltrexone hydrochloride tablets 50 mg (Nalorex® tablets, Bristol-Myers Squibb Pharmaceuticals Ltd), were administered orally as follows:

One naltrexone tablet 50 mg, swallowed whole with 100 ml water, at −13 h (Days −1, 7, and 14), and at −1 h and 11 h (Days 1, 8, and 15) relative to study drug dosing (3 doses in total).

6. Pharmacokinetic Parameters

Plasma concentration data and pharmacokinetic parameters were listed for subjects in the enrolled population.

Plasma concentration data for each analyte were summarized descriptively by time-point and treatment for subjects in the enrolled population. Individual and mean plasma concentrations for each analyte were also plotted over time for each treatment.

Pharmacokinetic parameters (AUCt, AUCINF, Cmax, tmax, LambdaZ and t1/2Z) for each analyte were summarised descriptively by treatment for all subjects in the full analysis population for pharmacokinetic parameters. To have a valid pharmacokinetic parameter, a subject must not have experienced vomiting within 12 hours after dosing with OXN PR tablet 20/10 or within 6 hours after dosing with OXN IR tablet 20/10 or oxycodone IR capsule 20 mg.

Log-transformed data for the analytes oxycodone, noroxycodone, oxymorphone, noroxymorphone, naloxone, 6β-naloxol, naloxone-3-glucuronide and 6β-naloxol-3-glucuronide and the pharmacokinetic parameters AUCt, AUCINF and Cmax were analysed using a mixed effect linear model 18, with fixed terms for treatment and period and a random effect for subject.

Treatment ratios/differences and their associated 90% confidence intervals were calculated from the least square means.

The treatments to be compared were as follows:
IR OXN 20/10 vs oxycodone IR 20 mg
IR OXN 20/10 vs OXN PR 20/10

Metabolite: parent drug ratios were calculated for each treatment using AUCt and, where possible, AUCINF values.

All pharmacokinetic calculations were conducted using WinNonlin Enterprise Edition, version 4.1.

7. Results

Figure 7:
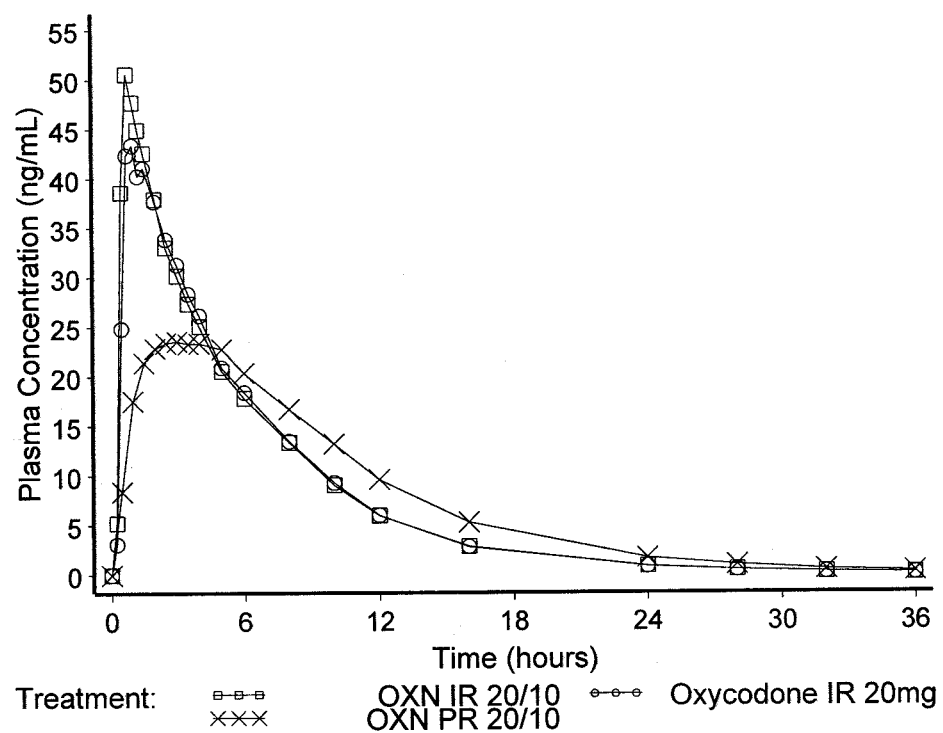
FIG. 7 depicts the mean blood plasma concentration of oxycodone as determined for IR OXN 20/10, IR Oxycodone 20 mg and PR Oxycodone 20/10 (Targin®) in Experiment 3 for 21 subjects.
Figure 8:
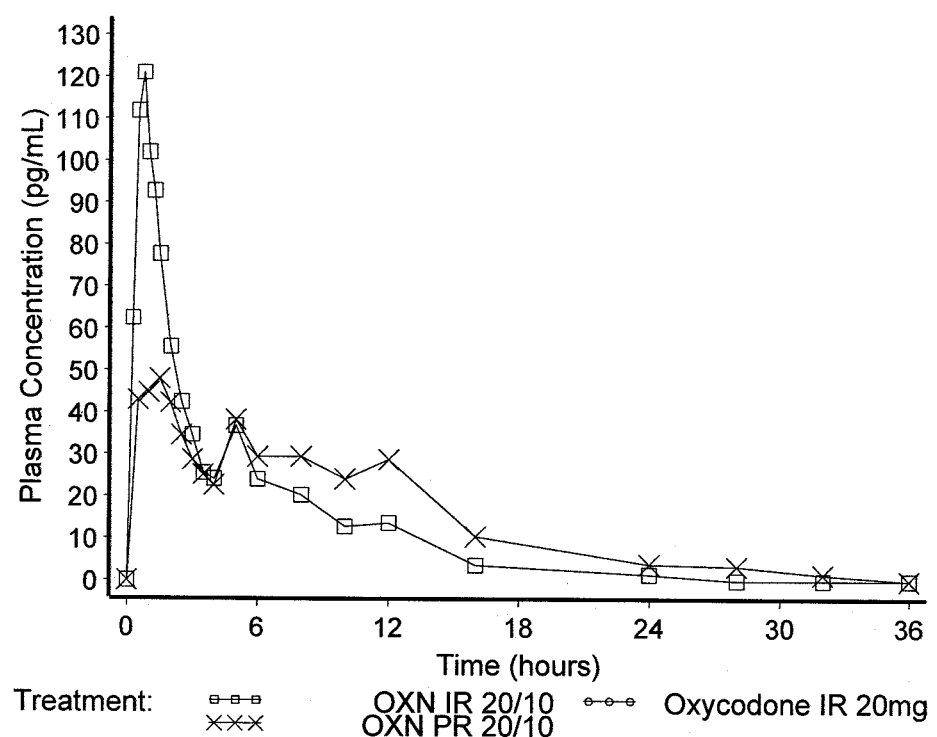
FIG. 8 depicts the mean blood plasma concentration of naloxone as determined for IR OXN 20/10, IR Oxycodone 20 mg and PR Oxycodone 20/10 (Targin®) in Experiment 3 for 21 subjects.
Figure 9:
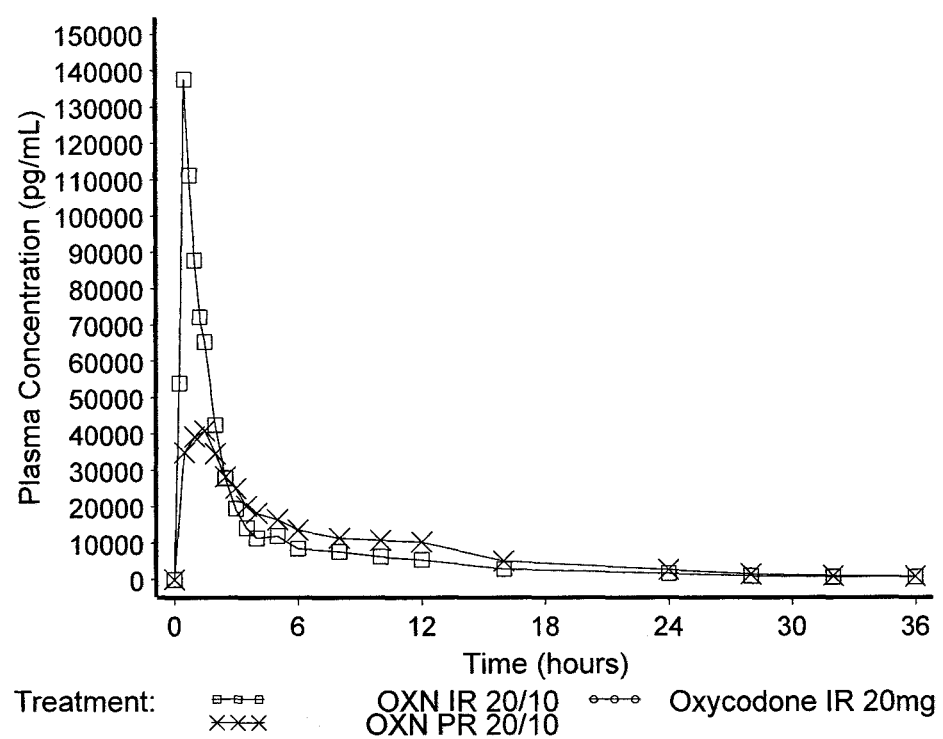
FIG. 9 depicts the mean blood plasma concentration of naloxone-3-glucuronide as determined for IR OXN 20/10, IR Oxycodone 20 mg and PR Oxycodone 20/10 (Torgin®) in Experiment 3 for 21 subjects.

The results for the pharmacokinetic parameters of oxycodone, naloxone and naloxone-3-glucuronide are shown in FIGS. 7 to 9 respectively for the analysed subjects.

Oxycodone

The summary statistics for oxycodone are shown in Table 12.

TABLE 12

Summary Statistics for Oxycodone Pharmacokinetic Parameters

| PK Parameters | Statistics | OXN IR 20/10 | Oxycodone IR 20 mg | OXN PR 20/10 |
|---|---|---|---|---|
| AUCt (ng · h/ml) | n | 21 | 20 | 18 |
| | Geometric Mean | 269.7 | 267.2 | 269.8 |
| | Geometric SE | 1.06 | 1.06 | 1.05 |
| | Exponentiated LS Mean | 268.8 | 270.9 | 277.3 |
| AUCINF (ng · h/ml) | n | 21 | 20 | 17 |
| | Geometric Mean | 270.9 | 268.4 | 275.5 |
| | Geometric SE | 1.06 | 1.06 | 1.05 |
| | Exponentiated LS Mean | 270.0 | 272.1 | 280.3 |
| Cmax (ng/ml) | n | 21 | 20 | 18 |
| | Geometric Mean | 56.02 | 55.16 | 25.25 |
| | Geometric SE | 1.074 | 1.071 | 1.037 |
| | Exponentiated LS Mean | 55.78 | 55.75 | 25.43 |
| tmax (h) | n | 21 | 20 | 18 |
| | Median | 0.75 | 1 | 2.5 |
| | Range | 0.5, 1.5 | 0.5, 3 | 1, 4 |
| t½Z (h) | n | 21 | 20 | 17 |
| | Mean | 4.20 | 4.15 | 4.30 |
| | SE | 0.133 | 0.127 | 0.194 |
| | LS Mean | 4.19 | 4.13 | 4.35 |
| LambdaZ ($h^{-1}$) | n | 21 | 20 | 17 |
| | Mean | 0.168 | 0.169 | 0.166 |
| | SE | 0.0051 | 0.0045 | 0.0072 |
| | LS Mean | 0.168 | 0.170 | 0.164 |

Compared with OXN PR tablet 20/10, IR OXN IR 20/10 had a mean oral availability of oxycodone of 96.3% with 90% confidence intervals that met the AUC criteria for bioequivalence. When comparing an immediate release and prolonged release formulation, the Cmax for OXN IR tablet 20/10 was significantly higher than for OXN PR tablet 20/10.

Compared with the oxycodone IR capsule, IR OXN 20/10 had a mean oral availability of oxycodone of 99.2%, and a mean Cmax ratio of 100%. The bioequivalence assessments for these comparisons all had 90% confidence intervals that met the criteria for bioequivalence.

The mean half-life values for oxycodone were similar across all treatments, ranging from 4.2 to 4.3 hours.

IR OXN 20/10 and oxycodone IR capsule 20 mg had similar median tmax values. OXN PR 20/10 had a later tmax than the other treatments.

Results of the statistical analysis of oxycodone pharmacokinetic parameters are presented in Table 13.

TABLE 13

Summary of Ratios for Oxycodone Pharmacokinetic Parameters

| PK Parameters | Treatment Comparison | Test/ Reference[a] | 90% Confidence Interval[b] Lower | Upper |
|---|---|---|---|---|
| AUCt | OXN IR 20/10 vs. OXN PR 20/10 | 96.9 | 92.0 | 102.2 |
| | OXN IR 20/10 vs. oxycodone IR 20 mg | 99.2 | 94.4 | 104.3 |
| AUCINF | OXN IR 20/10 vs. OXN PR 20/10 | 96.3 | 91.3 | 101.6 |
| | OXN IR 20/10 vs. oxycodone IR 20 mg | 99.2 | 94.4 | 104.3 |
| Cmax | OXN IR 20/10 vs. OXN PR 20/10 | 219.3 | 193.9 | 248.0 |
| | OXN IR 20/10 vs. oxycodone IR 20 mg | 100.0 | 88.9 | 112.6 |

[a]Estimate from mixed-effects linear model. Natural log parameter estimates calculated by transforming the log-scale estimates back to the linear scale, that is estimates of ratios.
[b]90% confidence intervals obtained by transforming the confidence intervals on the log scale to the ratio scale.

Naloxone-3-glucuronide

The summary statistics for naloxone-3-glucuronide are shown in Table 14.

TABLE 14

Summary Statistics for Naloxone-3-glucuronide Pharmacokinetic Parameters

| PK Parameters | Statistics | OXN IR 20/10 | OXN PR 20/10 |
|---|---|---|---|
| AUCt (ng · h/ml) | n | 21 | 18 |
| | Geometric Mean | 297.0 | 288.0 |
| | Geometric SE | 1.05 | 1.06 |
| | Exponentiated LS Mean | 297.5 | 286.6 |
| AUCINF (ng · h/ml) | n | 9 | 11 |
| | Geometric Mean | 301.3 | 311.0 |
| | Geometric SE | 1.05 | 1.08 |
| | Exponentiated LS Mean | 288.7 | 319.3 |
| Cmax (ng/ml) | n | 21 | 18 |
| | Geometric Mean | 143.58 | 47.22 |
| | Geometric SE | 1.070 | 1.055 |
| | Exponentiated LS Mean | 144.40 | 46.17 |
| tmax (h) | n | 21 | 18 |
| | Median | 0.5 | 1 |
| | Range | 0.25, 1.5 | 0.5, 2 |
| t½Z (h) | n | 9 | 11 |
| | Mean | 8.73 | 9.08 |
| | SE | 1.359 | 1.307 |
| | LS Mean | 6.78 | 10.05 |
| LambdaZ ($h^{-1}$) | n | 9 | 11 |
| | Mean | 0.092 | 0.087 |
| | SE | 0.0111 | 0.0080 |
| | LS Mean | 0.099 | 0.086 |

Compared with OXN PR tablet 20/10, IR OXN 20/10 had a mean oral availability of naloxone-3-glucuronide of 90.4% with 90% confidence intervals that met the AUC criteria for bioequivalence. When comparing an immediate release and prolonged release formulation, the Cmax for IR OXN 20/10 was significantly higher than for OXN PR tablet 20/10.

The mean half-life values were similar for the IR OXN (8.7 hours) and OXN PR (9.1 hours) tablets.

The tmax value for OXN PR tablet 20/10 was later than for IR OXN 20/10.

Results of the statistical analysis of naloxone-3-glucuronide pharmacokinetic parameters are presented in Table 15.

TABLE 15

Summary of Ratios for Naloxone-3-glucuronide Pharmacokinetic Parameters

| PK Parameters | Treatment Comparison | Test/Reference[a] | 90% Confidence Interval[b] Lower | Upper |
|---|---|---|---|---|
| AUCt | OXN IR 20/10 vs. OXN PR 20/10 | 103.8 | 99.0 | 108.9 |
| AUCINF | OXN IR 20/10 vs. OXN PR 20/10 | 90.4 | 80.3 | 101.7 |
| Cmax | OXN IR 20/10 vs. OXN PR 20/10 | 312.7 | 276.4 | 353.9 |

[a]Estimate from mixed-effects linear model. Natural log parameter estimates calculated by transforming the log-scale estimates back to the linear scale, that is estimates of ratios.
[b]90% confidence intervals obtained by transforming the confidence intervals on the log scale to the ratio scale.

8. Conclusions

The results for the pharmacokinetic parameters revealed the good equivalent bioavailability of oxycodone and naloxone (or surrogate naloxone-3-glucuronide) from IR OXN 20/10 mg and OXN PR tablet 20/10 mg, and the bioequivalence of IR OXN 20/10 mg and oxycodone IR capsule 20 mg with respect to oxycodone. Naloxone, as expected, had a very low bioavailability, confirming the results of previous studies and supporting the analysis of the surrogate naloxone-3-glucuronide.

Experiment 4

Storage Stability of IR-OXN 20/10, IR-OXN10/5, IR-OXN5/2.5 and IR-OXN2.5/1.25 Tablets Samples of IR-OXN 20/10, IR-OXN10/5, IR-OXN5/2.5 and IR-OXN2.5/1.25 tablets were stored in PVC/PVdC aluminium foil blister packs at 25° C./60% RH and 40° C./75% RH.

Stability data is provided for batches of IR-OXN 20/10, IR-OXN10/5, IR-OXN5/2.5 and IR-OXN2.5/1.25 tablets after 3 months storage at 25° C./60% RH and 40° C./75% RH.

The data depicted below confirm the stability of oxycodone hydrochloride/naloxone hydrochloride immediate release tablets with respect to physical characteristics and dissolution.

Storage of IR-OXN 2.5/1.25 at 25° C./60% RH

| Analysis | INITIAL | 3 months |
|---|---|---|
| Average Weight | | |
| Mean (mg) | 153.53 | 155.21 |
| Hardness | | |
| Mean (kp) | 5.17 | 4.10 |
| Naloxone HCl | | |
| Naloxone hydrochloride (mg/tab) | 1.20 | 1.21 |
| Oxycodone HCl | | |
| Oxycodone hydrochloride (mg/tab) | 2.44 | 2.43 |
| Dissolution Mean | | |
| Naloxone | | |
| 15 mins | 96 | 98 |
| 45 mins | 98 | 99 |
| Oxycodone | | |
| 15 mins | 97 | 99 |
| 45 mins | 98 | 98 |

Storage of IR-OXN 2.5/1.25 at 40° C./75% RH

| Analysis | INITIAL | 1 month | 3 months |
|---|---|---|---|
| Average Weight | | | |
| Mean (mg) | 153.53 | 155.03 | 156.05 |
| Hardness | | | |
| Mean (kp) | 5.17 | 3.42 | 2.98 |
| Naloxone HCl | | | |
| Naloxone hydrochloride (mg/tab) | 1.20 | 1.20 | 1.16 |
| Oxycodone HCl | | | |
| Oxycodone hydrochloride (mg/tab) | 2.44 | 2.42 | 2.38 |
| Dissolution Mean | | | |
| (oxycodone) | | | |
| 15 min | 97 | 97 | 95 |
| 45 min | 98 | 98 | 95 |
| (naloxone) | | | |
| 15 min | 97 | 97 | 94 |
| 45 min | 98 | 98 | 94 |

Storage of IR-OXN 5/2.5 at 25° C./60% RH

| Analysis | INITIAL | 3 months |
|---|---|---|
| Average Weight | | |
| Mean (mg) | 152.54 | 154.20 |
| Hardness | | |
| mean (kp) | 4.82 | 3.50 |
| Naloxone HCl | | |
| Naloxone hydrochloride (mg/tab) | 2.37 | 2.40 |
| Oxycodone HCl | | |
| Oxycodone hydrochloride (mg/tab) | 4.86 | 4.91 |
| Dissolution Mean | | |
| Oxcodone | | |
| 15 mins | 97 | 100 |
| 45 mins | 98 | 100 |
| Naloxone | | |
| 15 mins | 95 | 86 |
| 45 mins | 96 | 97 |

Total related substances after initial storage wee about 0.3%. This changed to a maximum of 0.5% after storage for 12 months.

Storage of IR-OXN 5/2.5 at 40° C./75% RH

| Analysis | INITIAL | 1 month | 3 months |
|---|---|---|---|
| Average Weight | | | |
| Oxycodone hydrochloride (mg) | 152.54 | 156.31 | 153.94 |
| Hardness | | | |
| Oxycodone hydrochloride (kp) | 4.82 | 2.28 | 2.32 |
| Naloxone HCl | | | |
| Naloxone hydrochloride (mg/tab) | 2.37 | 2.39 | 2.34 |
| Oxycodone HCl | | | |
| Oxycodone hydrochloride (mg/tab) | 4.86 | 4.94 | 4.84 |
| Dissolution Mean | | | |
| Oxycodone | | | |
| 15 mins | 97 | 97 | 100 |
| 45 mins | 98 | 97 | 100 |
| Naloxone | | | |
| 15 mins | 95 | 94 | 96 |
| 45 mins | 96 | 94 | 96 |

Total related substances after initial storage wee about 0.3%. This changed to a maximum of 2.3% after storage for 6 months.

Storage of IR-OXN 10/5 at 25° C./60% RH

| Analysis | INITIAL | 3 months |
|---|---|---|
| Average Weight | | |
| mean (mg) | 155.16 | 158.02 |
| Hardness | | |
| mean (kp) | 4.38 | 3.68 |
| Naloxone HCl | | |
| Naloxone hydrochloride (mg/tab) | 4.93 | 5.00 |
| Oxycodone HCl | | |
| Oxycodone hydrochloride (mg/tab) | 10.11 | 10.30 |
| Dissolution Mean | | |
| Oxycodone | | |
| 15 mins | 102 | 104 |
| 45 mins | 103 | 104 |
| Naloxone | | |
| 15 mins | 100 | 100 |
| 45 mins | 101 | 100 |

Total related substances after initial storage wee about 0.3%. This remained constant over a storage period of 12 months.

Storage of IR-OXN 10/5 at 40° C./75% RH

| Analysis | INITIAL | 1 month | 3 months |
|---|---|---|---|
| Average Weight | | | |
| mean (mg) | 155.16 | 157.58 | 157.47 |
| Hardness | | | |
| Mean (kp) | 4.38 | 2.43 | 2.34 |
| Naloxone HCl | | | |
| Naloxone hydrochloride (mg/tab) | 4.93 | 4.89 | 4.84 |
| Oxycodone HCl | | | |
| Oxycodone hydrochloride (mg/tab) | 10.11 | 10.15 | 10.03 |
| Dissolution mean | | | |
| Oxycodone | | | |
| 15 mins | 102 | 102 | 103 |
| 45 mins | 103 | 102 | 103 |
| Naloxone | | | |
| 15 mins | 100 | 98 | 99 |
| 45 mins | 101 | 99 | 99 |

Total related substances after initial storage wee about 0.3%. This changed to a maximum of 1.7% after storage for 6 months.

Storage of IR-OXN 20/10 at 25° C./60% RH

| Analysis | INITIAL | 3 months |
|---|---|---|
| Average Weight | | |
| Mean (mg) | 156.65 | 156.78 |
| Hardness | | |
| Mean (kp) | 4.82 | 4.19 |
| Naloxone HCl | | |
| Naloxone hydrochloride (mg/tab) | 9.61 | 9.69 |
| Oxycodone HCl | | |
| Oxycodone hydrochloride (mg/tab) | 19.72 | 19.72 |
| Dissolution Mean | | |
| Oxycodone | | |
| 15 mins | 99 | 100 |
| 45 mins | 100 | 100 |
| Naloxone | | |
| 15 mins | 97 | 99 |
| 45 mins | 98 | 99 |

Total related substances after initial storage wee about 0.3%. This changed to a maximum of 0.4% after storage for 12 months.

Storage of IR-OXN 20/10 at 40° C./75% RH

| Analysis | INITIAL | 1 month | 3 months |
|---|---|---|---|
| Average Weight | | | |
| Mean (mg) | 156.65 | 157.19 | 158.31 |
| Hardness | | | |
| Mean (kp) | 4.82 | 3.84 | 3.21 |
| Naloxone HCl | | | |
| Naloxone hydrochloride (mg/tab) | 9.61 | 9.66 | 9.67 |
| Oxycodone HCl | | | |
| Oxycodone hydrochloride (mg/tab) | 19.72 | 19.72 | 19.75 |
| Dissolution (mean) | | | |
| Oxycodone | | | |
| 15 mins | 99 | 97 | 100 |
| 45 mins | 100 | 98 | 97 |
| Naloxone | | | |
| 15 mins | 97 | 99 | 95 |
| 45 mins | 98 | 96 | 95 |

Total related substances after initial storage wee about 0.3%. This changed to a maximum of 0.7% after storage for 6 months.

The invention claimed is:

1. An oral immediate release pharmaceutical composition comprising:
   an amount of oxycodone or a pharmaceutically acceptable salt thereof equivalent to about 5.0 mg to about 40 mg of oxycodone hydrochloride; and
   an amount of naloxone or a pharmaceutically acceptable salt thereof equivalent to about 2.5 mg to about 20 mg of naloxone hydrochloride,
   wherein the oxycodone or pharmaceutically acceptable salt thereof and the naloxone or pharmaceutically acceptable salt thereof are present in the composition in about a 2:1 ratio (oxycodone or a pharmaceutically acceptable salt thereof: naloxone or a pharmaceutically acceptable salt thereof) by weight,
   wherein the composition releases in vitro, when measured using the Ph. Eur. Paddle Method at 100 rpm in 0.1 N hydrochloric acid at 37° C. and using UV detection at 230 nm, ≥75% of the oxycodone or pharmaceutically acceptable salt thereof by weight and ≥75% of the naloxone or pharmaceutically acceptable salt thereof by weight at 45 min.

2. The oral immediate release pharmaceutical composition of claim 1, wherein the composition comprises oxycodone hydrochloride and naloxone hydrochloride.

3. The oral immediate release pharmaceutical composition of claim 2, wherein the composition comprises oxycodone hydrochloride and naloxone hydrochloride as the sole pharmaceutically active agents.

4. The oral immediate release pharmaceutical composition of claim 1, wherein the composition comprises:
   an amount of oxycodone or a pharmaceutically acceptable salt thereof equivalent to about 5.0 mg to about 20 mg of oxycodone hydrochloride; and
   an amount of naloxone or a pharmaceutically acceptable salt thereof equivalent to about mg to about 10 mg of naloxone hydrochloride.

5. The oral immediate release pharmaceutical composition of claim 4, wherein the composition comprises:
   about 5.0 mg to about 20 mg of oxycodone hydrochloride; and
   about 2.5 mg to about 10 mg of naloxone hydrochloride.

6. The oral immediate release pharmaceutical composition of claim 5, wherein the composition comprises oxycodone hydrochloride and naloxone hydrochloride as the sole pharmaceutically active agents.

7. The oral immediate release pharmaceutical composition of claim 1, wherein the composition releases in vitro, when measured using the Ph. Eur. Paddle Method at 100 rpm in 0.1 N hydrochloric acid at 37° C. and using UV detection at 230 nm, ≥80% of the oxycodone or pharmaceutically acceptable salt thereof by weight and ≥80% of the naloxone or pharmaceutically acceptable salt thereof by weight at 45 min.

8. The oral immediate release pharmaceutical composition of claim 7, wherein the composition releases in vitro, when measured using the Ph. Eur. Paddle Method at 100 rpm in 0.1 N hydrochloric acid at 37° C. and using UV detection at 230 nm, ≥80% of the oxycodone or pharmaceutically acceptable salt thereof by weight and ≥80% of the naloxone or pharmaceutically acceptable salt thereof by weight at 15 min.

9. The oral immediate release pharmaceutical composition of claim 8, wherein the composition releases in vitro, when measured using the Ph. Eur. Paddle Method at 100 rpm in 0.1 N hydrochloric acid at 37° C. and using UV detection at 230 nm, ≥90% of the oxycodone or pharmaceutically acceptable salt thereof by weight and ≥90% of the naloxone or pharmaceutically acceptable salt thereof by weight at 15 min.

10. The oral immediate release pharmaceutical composition of claim 9, wherein the composition releases in vitro, when measured using the Ph. Eur. Paddle Method at 100 rpm in 0.1 N hydrochloric acid at 37° C. and using UV detection at 230 nm, ≥95% of the oxycodone or pharmaceutically acceptable salt thereof by weight and ≥95% of the naloxone or pharmaceutically acceptable salt thereof by weight at 15 min.

11. The oral immediate release pharmaceutical composition of claim 1, wherein the composition is in the form of a tablet, of a capsule, of multiparticulates, of pellets, or of a liquid.

12. The oral immediate release pharmaceutical composition of claim 1, wherein the composition comprises a diluent.

13. The oral immediate release pharmaceutical composition of claim 1, wherein the composition comprises a disintegrant.

14. The oral immediate release pharmaceutical composition of claim 1,
   wherein the composition comprises about 5.0 mg to about 20 mg of oxycodone hydrochloride and about 2.5 mg to about 10 mg of naloxone hydrochloride in about a 2:1 ratio (oxycodone hydrochloride:naloxone hydrochloride) by weight,
   wherein the composition comprises oxycodone hydrochloride and naloxone hydrochloride as the sole pharmaceutically active agents,
   wherein the composition is in solid form,
   wherein the composition comprises a disintegrant, and
   wherein the composition releases in vitro, when measured using the Ph. Eur. Paddle Method at 100 rpm in 0.1 N hydrochloric acid at 37° C. and using UV detection at 230 nm, ≥80% of the oxycodone hydrochloride by weight and ≥80% of the naloxone hydrochloride by weight at 45 min.

15. The oral immediate release pharmaceutical composition of claim 14, wherein the composition releases in vitro, when measured using the Ph. Eur. Paddle Method at 100 rpm in 0.1 N hydrochloric acid at 37° C. and using UV detection at 230 nm, ≥95% of the oxycodone hydrochloride by weight and ≥95% of the naloxone hydrochloride by weight at 15 min.

16. The oral immediate release pharmaceutical composition of claim 1, wherein the composition comprises oxycodone or a pharmaceutically acceptable salt thereof and naloxone or a pharmaceutically acceptable salt thereof as the sole pharmaceutically active agents.

17. The oral immediate release pharmaceutical composition of claim 1, wherein the composition further comprises starch and lactose.

18. The oral immediate release pharmaceutical composition of claim 1, wherein the composition comprises:
   5 mg of oxycodone hydrochloride and 2.5 mg naloxone hydrochloride;
   10 mg of oxycodone hydrochloride and 5 mg naloxone hydrochloride; or
   20 mg of oxycodone hydrochloride and 10 mg naloxone hydrochloride.

19. An oral immediate release pharmaceutical composition comprising:
   an amount of oxycodone or a pharmaceutically acceptable salt thereof equivalent to about 2.5 mg to about 40 mg of oxycodone hydrochloride; and
   an amount of naloxone or a pharmaceutically acceptable salt thereof equivalent to about 2.5 mg to about 20 mg of naloxone hydrochloride,
   wherein the composition releases in vitro, when measured using the Ph. Eur. Paddle Method at 100 rpm in 0.1 N hydrochloric acid at 37° C. and using UV detection at 230 nm, ≥90% of the oxycodone or pharmaceutically acceptable salt thereof by weight and ≥90% of the naloxone or pharmaceutically acceptable salt thereof by weight at 15 min.

20. The oral immediate release pharmaceutical composition according to claim 19, wherein the composition releases in vitro, when measured using the Ph. Eur. Paddle Method at 100 rpm in 0.1 N hydrochloric acid at 37° C. and using UV detection at 230 nm, ≥95% of the oxycodone or pharmaceutically acceptable salt thereof by weight and ≥95% of the naloxone or pharmaceutically acceptable salt thereof by weight at 15 min.

21. The oral immediate release pharmaceutical composition according to claim 19, wherein the pharmaceutical composition comprises:
   an amount of oxycodone or a pharmaceutically acceptable salt thereof equivalent to about 2.5 mg to about 20 mg of oxycodone hydrochloride; and
   an amount of naloxone or a pharmaceutically acceptable salt thereof equivalent to about 2.5 mg to about 10 mg of naloxone hydrochloride.

22. The oral immediate release pharmaceutical composition according to claim 19, wherein the oxycodone or pharmaceutically acceptable salt thereof and the naloxone or pharmaceutically acceptable salt thereof are present in about a 2:1 ratio (oxycodone or a pharmaceutically acceptable salt thereof: naloxone or a pharmaceutically acceptable salt thereof) by weight.

23. The oral immediate release pharmaceutical composition according to claim 19, wherein the pharmaceutical composition is in solid form.

24. The oral immediate release pharmaceutical composition according to claim 19, wherein the pharmaceutical composition additionally comprises a disintegrant.

25. The oral immediate release pharmaceutical composition according to claim 19, wherein the pharmaceutical composition comprises oxycodone hydrochloride and naloxone hydrochloride as the sole pharmaceutically active agents.

26. The oral immediate release pharmaceutical composition of claim 19, wherein the composition comprises oxycodone or a pharmaceutically acceptable salt thereof and naloxone or a pharmaceutically acceptable salt thereof as the sole pharmaceutically active agents.

27. The oral immediate release pharmaceutical composition of claim 19, wherein the composition further comprises starch and lactose.

28. The oral immediate release pharmaceutical composition of claim 19, wherein the composition comprises:
   about 2.5 mg to about 20 mg of oxycodone hydrochloride; and
   about 2.5 mg to about 10 mg of naloxone hydrochloride.

29. The oral immediate release pharmaceutical composition of claim 19, wherein the composition comprises:
   5 mg of oxycodone hydrochloride and 2.5 mg naloxone hydrochloride;
   10 mg of oxycodone hydrochloride and 5 mg naloxone hydrochloride; or
   20 mg of oxycodone hydrochloride and 10 mg naloxone hydrochloride.

30. A method of titrating a patient in need thereof and suffering from pain by administering an oral immediate release pharmaceutical composition of claim 1 or claim 19.

31. A method of treating breakthrough pain in a patient in need thereof and suffering from pain by administering an oral immediate release pharmaceutical composition of claim 1 or claim 19.

* * * * *